United States Patent
Diaz et al.

(10) Patent No.: US 8,093,244 B2
(45) Date of Patent: Jan. 10, 2012

(54) HETEROARYL UREA DERIVATIVES USEFUL FOR INHIBITING CHK1

(75) Inventors: Frank Diaz, Florence, AL (US); Francine S. Farouz, San Diego, CA (US); Ryan Coatsworth Holcomb, Salt Lake City, UT (US); Edward A. Kesicki, Bothell, WA (US); Kimba Lee Fischer, Longmont, CO (US); Adam Wade Cook, Broomfield, CO (US)

(73) Assignee: ICOS Corporation, Indianapolis, IN (US)

( * ) Notice: Subject to any disclaimer, the term of this patent is extended or adjusted under 35 U.S.C. 154(b) by 658 days.

(21) Appl. No.: 11/908,416

(22) PCT Filed: Mar. 29, 2006

(86) PCT No.: PCT/US2006/011584
§ 371 (c)(1),
(2), (4) Date: Nov. 19, 2008

(87) PCT Pub. No.: WO2006/105262
PCT Pub. Date: Oct. 5, 2006

(65) Prior Publication Data
US 2009/0143357 A1    Jun. 4, 2009

Related U.S. Application Data

(60) Provisional application No. 60/666,026, filed on Mar. 29, 2005.

(51) Int. Cl.
*A61P 35/00* (2006.01)
*A61K 31/497* (2006.01)
*A61K 31/5355* (2006.01)
*A61K 31/541* (2006.01)
*C07D 403/12* (2006.01)
*C07D 413/12* (2006.01)
*C07D 417/12* (2006.01)

(52) U.S. Cl. ...................................... 514/235.8; 544/120
(58) Field of Classification Search ............... 514/235.8; 544/120
See application file for complete search history.

(56) References Cited

U.S. PATENT DOCUMENTS

2004/0014765 A1    1/2004    Boyle et al.
2004/0259885 A1    12/2004   Li et al.

FOREIGN PATENT DOCUMENTS

WO    WO02/070494 A    9/2002
WO    WO2006/012308   2/2006

*Primary Examiner* — Brenda Coleman
(74) *Attorney, Agent, or Firm* — Danica Hostettler; Tina Tucker

(57) ABSTRACT

Substituted urea compounds useful in the treatment of diseases and conditions related to DNA damage or lesions in DNA replication are disclosed. Methods of making the compounds, and their use as therapeutic agents, for example, in treating cancer and other diseases characterized by defects in DNA replication, chromosome segregation, or cell division, also are disclosed.

3 Claims, No Drawings

HETEROARYL UREA DERIVATIVES USEFUL FOR INHIBITING CHK1

This application is a 35 U.S.C. 371 National Stage Filing of PCT/US2006/011584 filed Mar. 29, 2006, which claims priority to U.S. Provisional Application No. 60/666,026, filed Mar. 29, 2005.

FIELD OF THE INVENTION

The present invention relates to compounds useful for inhibiting enzymes that maintain and repair the integrity of genetic material. More particularly, the present invention relates to a series of aryl- and heteroaryl-substituted urea compounds, methods of making the compounds, and their use as therapeutic agents, for example, in treating cancer and other diseases characterized by defects in deoxyribonucleic acid (DNA) replication, chromosome segregation, or cell division.

BACKGROUND OF THE INVENTION

A large variety of diseases, conditions, and disorders (hereinafter "indications") are characterized as involving aberrantly proliferating cells. As used herein, "aberrantly proliferating cells" (or "aberrant cell proliferation") means cell proliferation that deviates from the normal, proper, or expected course. For example, aberrant cell proliferation includes inappropriate proliferation of cells wherein DNA or other cellular components have become damaged or defective. Aberrant cell proliferation also characterizes clinical indications caused by, mediated by, or resulting in inappropriately high levels of cell division, inappropriately low levels of cell death (e.g., apoptosis), or both. Such indications can be characterized, for example, by single or multiple local abnormal proliferations of cells, groups of cells or tissue(s), and include cancerous (benign or malignant) and noncancerous indications.

By definition, all cancers (benign and malignant) involve some form of aberrant cell proliferation. Some noncancerous indications also involve aberrant cell proliferation. Examples of noncancerous indications involving aberrant cell proliferation include rheumatoid arthritis, psoriasis, vitiligo, Wegener's granulomatosis, and systemic lupus.

One approach to treating indications involving aberrantly proliferating cells involves the use of DNA damaging agents. These agents are designed to kill aberrantly proliferating cells by disrupting vital cellular processes such as DNA metabolism, DNA synthesis, DNA transcription, and microtubule spindle formation. They also can operate, for example, by introducing lesions into DNA that perturb chromosomal structural integrity. DNA damaging agents are designed and administered in ways that attempt to induce maximum damage and consequent cell death in aberrantly proliferating cells with a minimum damage to normal, healthy cells.

A large variety of DNA damaging agents has been developed to date, including chemotherapeutics and radiation, and others are in development. Unfortunately, the effectiveness of DNA damaging agents in treating conditions involving aberrant cell proliferation has been less than desired, particularly in the treatment of cancer. The selectivity of such agents for aberrantly proliferating cells over healthy cells (sometimes referred to as the therapeutic index) often is marginal.

Moreover, all cells have sensing and repair mechanisms that can work at cross purposes to DNA damaging agents. Such sensing mechanisms, called cell cycle checkpoints, help to maintain the order of the various cell replication stages and to ensure that each step is executed with high fidelity (Hartwell et al., *Science*, 246:629-634 (1989); Weinert et al., *Genes Dev.*, 8:652 (1994)). When cells detect DNA damage, including damage purposefully induced by DNA damaging agents, certain signaling pathways activate cell cycle checkpoints and the cell replication cycle temporarily ceases ("arrests"). This arrest allows cells time to repair their DNA, often to a degree sufficient to allow them to continue to survive and proliferate. In the case of aberrantly proliferating cells, this repair is unwanted, as it may undermine efforts to induce DNA damage sufficient to kill such cells.

For example, the chemotherapeutic agent called GEMZAR™ (gemcitabine, or 2',2'-difluoro-2'-deoxycytidine) damages DNA by incorporating itself into DNA during synthesis. Left unrepaired, damaged DNA generally is rendered incapable of sustaining life. In many targeted cells, however, cell cycle checkpoints detect the improperly made (or otherwise damaged) DNA. The activated cell cycle checkpoints trigger cell cycle arrest for a time sufficient to allow damaged DNA to be repaired. This is one way in which aberrantly proliferating cells are theorized to resist the cell-killing effect of DNA-damaging agents such as chemotherapeutics, radiation, and other therapies.

Other DNA-damaging agents cause tumor cells to arrest in S-phase. Tumor cells have been observed to resist certain chemotherapeutics simply by arresting in S phase while the chemotherapeutic agent is being administered. Then, as soon as the drug is removed, DNA damage is repaired, cell cycle arrest ceases, and the cells progress through the remainder of the cell cycle (Shi et al., *Cancer Res.* 61:1065-1072, 2001). Other therapeutics cause cell cycle arrest at other checkpoints, including G1 and G2. Inhibition of various DNA damage checkpoints therefore is expected to assist in preventing cells from repairing therapeutically induced DNA damage and to sensitize targeted cells to DNA damaging agents. Such sensitization is in turn expected to increase the therapeutic index of these therapies.

The cell cycle is structurally and functionally the same in its basic process and mode of regulation across all eukaryotic species. The mitotic (somatic) cell cycle consists of four phases: the G1 (gap) phase, the S (synthesis) phase, the G2 (gap) phase, and the M (mitosis) phase. The G1, S, and G2 phases are collectively referred to as interphase of the cell cycle. During the G1 phase, biosynthetic activities of the cell progress at a high rate. The S phase begins when DNA synthesis starts, and ends when the DNA content of the nucleus of the cell has been replicated and two identical sets of chromosomes are formed.

The cell then enters the G2 phase, which continues until mitosis starts. In mitosis, the chromosomes pair and separate, two new nuclei form, and cytokinesis occurs in which the cell splits into two daughter cells each receiving one nucleus containing one of the two sets of chromosomes. Cytokinesis terminates the M phase and marks the beginning of interphase of the next cell cycle. The sequence in which dell cycle events proceed is tightly regulated, such that the initiation of one cell cycle event is dependent on the completion of the prior cell cycle event. This allows fidelity in the duplication and segregation of genetic material from one generation of somatic cells to the next.

It has been reported that cell cycle checkpoints comprise at least three distinct classes of polypeptides, which act sequentially in response to cell cycle signals or defects in chromosomal mechanisms (Carr, *Science*, 271:314-315, 1996). The first class is a family of proteins that detect or sense DNA damage or abnormalities in the cell cycle. These sensors include Ataxia-telangiectasia Mutated protein (Atm) and Ataxia-Telangiectasia Rad-related protein (Atr). The second class of polypeptides amplify and transmit the signal detected by the detector and is exemplified by Rad53 (Alen et al. *Genes Dev.* 8:2416-2488, 1994) and Chk1. A third class of polypeptides includes cell cycle effectors, such as p53, that mediate a cellular response, for example, arrest of mitosis and apoptosis.

Much of the current understanding of the function of cell cycle checkpoints has been derived from the study of tumor derived cell lines. In many cases, tumor cells have lost key cell cycle check points (Hartwell et al., *Science* 266:1821-28, 1994). It has been reported that a key step in the evolution of cells to a neoplastic state is the acquisition of mutations that inactivate cell cycle checkpoint pathways, such as those involving p53 (Weinberg, *Cell* 81:323-330, 1995; Levine, *Cell* 88:3234-331, 1997). Loss of these cell cycle checkpoints results in the replication of tumor cells despite DNA damage.

Noncancerous tissue, which has intact cell cycle checkpoints, typically is insulated from temporary disruption of a single checkpoint pathway. Tumor cells, however, have defects in pathways controlling cell cycle progression such that the perturbation of additional checkpoints renders them particularly sensitive to DNA damaging agents. For example, tumor cells that contain mutant p53 are defective both in the G1 DNA damage checkpoint and in the ability to maintain the G2 DNA damage checkpoint (Bunz et al., *Science*, 282:1497-501, 1998). Checkpoint inhibitors that target initiation of the G2 checkpoint or the S phase checkpoint are expected to further cripple the ability of these tumor cells to repair DNA damage and, therefore, are candidates to enhance the therapeutic index of both radiation and systemic chemotherapy (Gesner, Abstract at SRI Conference: Protein Phosphorylation and Drug Discovery World Summit, March 2003).

In the presence of DNA damage or any impediment to DNA replication, the checkpoint proteins Atm and Atr initiate a signal transduction pathway leading to cell cycle arrest. Atm has been shown to play a role in a DNA damage checkpoint in response to ionizing radiation (IR). Atr is stimulated by agents that cause double strand DNA breaks, single strand DNA breaks, and agents that block DNA radiation.

Chk1 is a protein kinase that lies downstream from Atm and/or Atr in the DNA damage checkpoint signal transduction pathway (Sanchez et al., *Science*, 277:1497-1501, 1997; U.S. Pat. No. 6,218,109). In mammalian cells, Chk1 is phosphorylated in response to agents that cause DNA damage including ionizing radiation (IR), ultraviolet (UV) light, and hydroxyurea (Sanchez et al., supra; Lui et al., *Genes Dev.*, 14:1448-1459, 2000). This phosphorylation which activates Chk1 in mammalian cells is dependent on Atm (Chen et al., *Oncogene*, 18:249-256, 1999) and Atr (Lui et al., supra). Furthermore, Chk1 has been shown to phosphorylate both wee1 (O'Connell et al., *EMBO J.*, 16:545-554, 1997) and Pds1 (Sanchez et al., *Science*, 286:1166-1171, 1999), gene products known to be important in cell cycle control.

These studies demonstrate that mammalian Chk1 plays a role in the Atm dependent DNA damage checkpoint leading to arrest at S phase. A role for Chk1 in the S phase mammalian cells has recently been elucidated (Feijoo et al., *J. Cell Biol.*, 154:913-923, 2001; Zhao et al., *PNAS U.S.A*, 99:14795-800, 2002; Xiao et al., *J Biol Chem.*, 278(24):21767-21773, 2003; Sorensen et al., *Cancer Cell*, 3(3):247-58, 2003) highlighting the role of Chk1 in monitoring the integrity of DNA synthesis. Chk1 invokes an S-phase arrest by phosphorylating Cdc25A, which regulates cyclinA/cdk2 activity (Xiao et al., supra and Sorensen et al., supra). Chk1 also invokes a G2 arrest by phosphorylating and inactivating Cdc25C, the dual specificity phosphatase that normally dephosphorylates cyclin-B/cdc2 (also known as Cdk1) as cells progress from G2 into mitosis (Fernery et al., *Science*, 277:1495-7, 1997; Sanchez et al., supra; Matsuoka et al., *Science*, 282:1893-1897, 1998; and Blasina et al., *Curr. Biol.*, 9:1-10, 1999). In both cases, regulation of Cdk activity induces a cell cycle arrest to prevent cells from entering mitosis in the presence of DNA damage or unreplicated DNA.

Additional classes of cell cycle checkpoint inhibitors operate at either the G1 or G2/M phase. UCN-01, or 7-hydroxystaurosporine, originally was isolated as a nonspecific kinase inhibitor having its primary effect on protein kinase C, but recently has been found to inhibit the activity of Chk1 and abrogate the G2 cell cycle checkpoint (Shi et al., supra). Thus, because UCN-01 is a nonselective Chk1 inhibitor, it is toxic to cells at high doses. At low doses, it nonspecifically inhibits many cellular kinases and also inhibits the G1 checkpoint (Tenzer et al., *Curr. Med. Chem. AntiCancer Agents*, 3:35-46, 2003).

UCN-01 has been used in conjunction with cancer therapies, such as radiation, the anticancer agent camptothecin (Tenzer et al., supra), and gemcitabine (Shi et al., supra), with limited success. In addition, UCN-01 has been used to potentiate the effects of temozolomide (TMZ) induced DNA mismatch repair (MMR) in glioblastoma cells (Hirose et al., *Cancer Res.*, 61:5843-5849, 2001). In the clinic, UCN-01 is not an effective chemotherapeutic as expected, possibly due to a failure in treatment scheduling and a lack of identification of particular key molecular targets (Grant et al., *Drug Resistance Updates*, 6:15-26, 2003). Thus, Mack et al. report cell cycle-dependent potentiation of cisplatin by UCN-01 in a cultured nonsmall-cell lung carcinoma cell line, but do not identify with specificity the key cell cycle checkpoint(s) targeted by UCN-01. (Mack et al., *Cancer Chemother. Pharmacol.*, 51(4):337-348, 2003).

Several other strategies exist for sensitizing tumor cells to treatment with cell cycle affecting chemotherapeutics. For example, administration of 2-aminopurine abrogates multiple cell cycle checkpoint mechanisms, such as mimosine-induced G1 arrest or hydroxyurea-induced S phase arrest, allowing the cell to progress into and through mitosis (Andreassen et al., *Proc Natl Acad Sci U.S.A.*, 86:2272-2276, 1992). Caffeine, a methylxanthine, has also been used to enhance cytotoxicity of DNA-damaging agents, such as cisplatin and ionizing radiation, by mediating progression through the G2 checkpoint and thereby inducing cell death. (Bracey et al., *Clin. Cancer Res.*, 3:1371-1381, 1997). However, the dose of caffeine used to accomplish the cell cycle abrogation exceeds clinically acceptable levels and is not a viable therapeutic option. Additionally, antisense nucleotides to Chk1 kinase have been used to increase sensitivity to the topoisomerase inhibitor BNP1350 (Yin et al., *Biochem. Biophys. Res. Commun.*, 295:435-44, 2002), but demonstrate problems typically associated with antisense treatment and gene therapy.

Chk1 inhibitors have been disclosed, including aryl- and heteroaryl-substituted urea compounds described in U.S. patent application Ser. No. 10/087,715 and U.S. Provisional Patent Application Nos. 60/583,080, 60/585,292, and 60/602, 968; diaryl urea compounds described in U.S. Patent Publication No. 2004/0014765, U.S. Patent Publication No. US2003/199511, U.S. Patent Publication No. 2004/0014765, and WO 03/101444; methylxanthines and related compounds described in Fan et al., *Cancer Res.* 55:1649-54. 1995; ureidothiphenes described in WO 03/029241 and WO 03/028731; N-pyrrolopyridinyl carboxamides described in WO 03/028724; antisense Chk1 oligonucleotides described in WO 01/57206 and U.S. Pat. No. 6,211,164; Chk1 receptor antagonists described in WO 00/16781; heteroaromatic carboxamide derivatives described in WO 03/037886; aminothiophenes described in WO 03/029242; (indazolyl)benzimidazoles described in WO 03/004488; benzimidazole quinolinones described in U.S. Patent Publication No. 20040092535 and WO 04/018419; heterocyclic-hydroxyimino-fluorenes described in WO 02/16326; scytoneman derivatives, such as scytonemin, described in U.S. Pat. No. 6,495,586; heteroarylbenzamides described in WO 01/53274; indazoles described in WO 01/53268; indolacarbazoles described in Tenzer et al., supra; chromane derivatives described in WO 02/070515; paullones described in Schultz et al., J. Med. Chem., Vol:2909-2919, 1999; indenopyrazoles described in WO 99/17769; flavones described in Sedlacek et al., Int J. Oncol., 9:1143-1168, 1996; peptide derivatives of peptide loop of serine threonine kinases described in WO 98/53050; oxindoles described in WO 03/051838; diazepinoindolones described in WO 2004/063198; pyrimidines described in WO 2004/048343; urea compounds described in WO 2004/014876; and pyrrolocarbazoles, benzofuroisoindoles, and azacyclopentafluorenes described in WO 2003/091255.

However, a need remains in the art for effective and selective inhibitors of Chk1. The present invention addresses this and other needs.

SUMMARY OF THE INVENTION

The present invention relates to potent and selective inhibitors of the checkpoint kinase Chk1 that exhibit unexpected properties in biochemical and/or cell-based assays. The present Chk1 inhibitors are useful in treating indications involving aberrant cell proliferation, and as chemosensitizing and radiosensitizing agents in the treatment of indications related to DNA damage or lesions in DNA replication.

Therefore, one aspect of the present invention is to provide compounds of structural formula (I). Among other things, the compounds are useful in a method of inhibiting Chk1 comprising a step of administering an effective amount of a compound of structural formula (I) to an individual in need thereof.

Compounds of formula (I) have a structural formula:

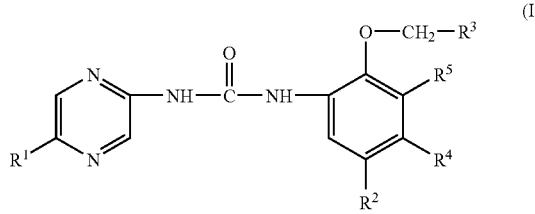
(I)

wherein $R^1$ is halo, $C_{1-3}$alkyl, CN, or $CF_3$;
$R^2$ is hydrogen, $C_{1-3}$alkyl, CN, $OC_{1-3}$alkyl, halo, or $N(R^b)_2$, wherein $R^b$, independently, is hydrogen or $C_{1-3}$alkyl;
$R^3$ is a 6- or 7-membered saturated heterocyclic ring containing one ring N—$R^a$ group and either a second ring N—$R^a$ group, a ring oxygen, or a ring sulfur, wherein $R^a$, independently, is hydrogen, $C_{1-3}$alkyl, $CH_2CN$, or $CH_2CH_2CN$, and wherein $R^3$ is optionally substituted with oxo(=O);
$R^4$ is hydrogen, $C_{1-3}$alkyl, $OC_{1-3}$alkyl, $SC_{1-3}$alkyl, $N(R^b)_2$, $NR^bC(=O)C_{1-3}$alkyl, or a 5- or 6-membered saturated heterocyclic ring containing one N—$R^a$ group and optionally ring substituted with one to three $C_{1-3}$alkyl groups;

or $R^2$ and $R^4$ are taken together with the carbons to which they are attached to form a 5- to 7-membered saturated carbocyclic ring;
and $R^5$ is hydrogen or halo,
provided that at least one of $R^2$ and $R^4$ is different from hydrogen, and that when $R^5$ is halo, $R^2$ or $R^4$ is hydrogen,
or pharmaceutically acceptable salts, prodrugs, or solvates thereof.

Another aspect of the present invention is to provide compounds of structural formula (II), which, among other applications, can be used in a method of inhibiting Chk1.

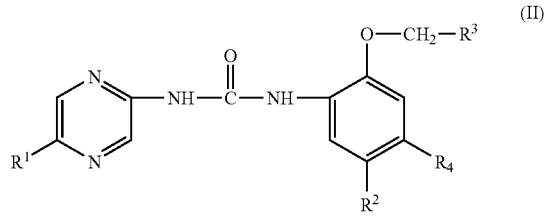
(II)

wherein $R^1$ is halo, $C_{1-3}$alkyl, CN, or $CF_3$;
$R^2$ is hydrogen, $C_{1-3}$alkyl, CN, $OC_{1-3}$alkyl, halo, or $N(R^b)_2$, wherein $R^b$, independently, is hydrogen or $C_{1-3}$alkyl;
$R^3$ is a 6- or 7-membered saturated heterocyclic ring containing one ring N—$R^a$ group and either a second ring N—$R^a$ group, a ring oxygen, or a ring sulfur, wherein $R^a$, independently, is hydrogen, $C_{1-3}$alkyl, or $CH_2CN$, and wherein $R^3$ is optionally substituted with oxo (=O);
$R^4$ is hydrogen, $C_{1-3}$alkyl, $OC_{1-3}$alkyl, or halo;
or $R^2$ and $R^4$ are taken together with the carbons to which they are attached to form a 5- to 7-membered saturated carbocyclic ring,
provided that at least one of $R^2$ and $R^4$ is different from hydrogen,
or pharmaceutically acceptable salts, prodrugs, or solvates thereof.

Another aspect of the present invention is to provide pharmaceutical compositions comprising one or more compound of structural formula (I) or (II), and use of the compositions in a therapeutic treatment of an indication, wherein inhibition of Chk1, in vivo or ex vivo, provides a therapeutic benefit or is of research or diagnostic interest.

Yet another aspect of the present invention is to provide a method of sensitizing cells in a subject undergoing a chemotherapeutic or radiotherapeutic treatment for an indication comprising administration of a compound of structural formula (I) or (II) in combination with a chemotherapeutic agent, a radiotherapeutic agent, or both, to the individual. A nonlimiting indication treated by this method is a cancer.

Another aspect of the present invention is to provide a method of inhibiting or preventing aberrant cell proliferation. In one embodiment, the method comprises contacting a cell population comprising aberrantly proliferating cells with at least one Chk1 activator in an amount and for a time sufficient to substantially synchronize cell cycle arrest among the aberrantly proliferating cells. Upon achieving substantial synchronization of cell cycle arrest in the cell population, the cell population is contacted with at least one Chk1 inhibitor in an amount and for a time sufficient to substantially abrogate the cell cycle arrest.

Another aspect of the present invention is to provide an article of manufacture for human pharmaceutical use comprising:

(a) a pharmaceutical composition comprising a compound of structural formula (I) or (II);

(b) a package insert providing that the composition is useful in the treatment of indications involving aberrant cell proliferation; and (c) a container.

Another aspect of the present invention is to provide:

(a) pharmaceutical composition comprising a compound of structural formula (I) or (II);

(b) a package insert providing that the composition is useful as a chemosensitizer or radiosensitizer in a treatment of an indication related to DNA lesions or DNA replication;

(c) a container.

These and other aspects of the present invention will become apparent from the following detailed description.

DETAILED DESCRIPTION

Compounds of the present invention have a structural formula (I):

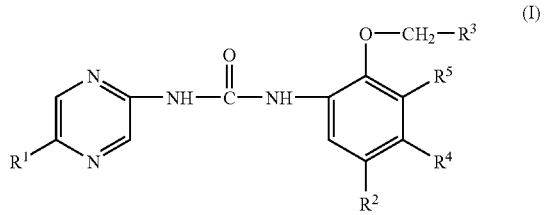

(I)

wherein $R^1$ is halo, $C_{1-3}$alkyl, CN, or $CF_3$;

$R^2$ is hydrogen, $C_{1-3}$alkyl, CN, $OC_{1-3}$alkyl, halo, or $N(R^b)_2$, wherein $R^b$, independently, is hydrogen or $C_{1-3}$alkyl;

$R^3$ is a 6- or 7-membered saturated heterocyclic ring containing one ring N—$R^a$ group and either a second ring N—$R^a$ group, a ring oxygen, or a ring sulfur, wherein $R^a$, independently, is hydrogen, $C_{1-3}$alkyl, $CH_2CN$, or $CH_2CH_2CN$, and wherein $R^3$ is optionally substituted with oxo(=O);

$R^4$ is hydrogen, $C_{1-3}$alkyl, $OC_{1-3}$alkyl, $SC_{1-3}$alkyl, $N(R^b)_2$, $NR^bC(=O)C_{1-3}$alkyl, or a 5- or 6-membered saturated heterocyclic ring containing one N—$R^a$ group and optionally ring substituted with one to three $C_{1-3}$alkyl groups;

or $R^2$ and $R^4$ are taken together with the carbons to which they are attached to form a 5- to 7-membered saturated carbocyclic ring;

and $R^5$ is hydrogen or halo, provided that at least one of $R^2$ and $R^4$ is different from hydrogen, and that when $R^5$ is halo, $R^2$ or $R^4$ is hydrogen, or pharmaceutically acceptable salts, prodrugs, or solvates thereof.

In one preferred embodiment, the compounds have a structural formula (II):

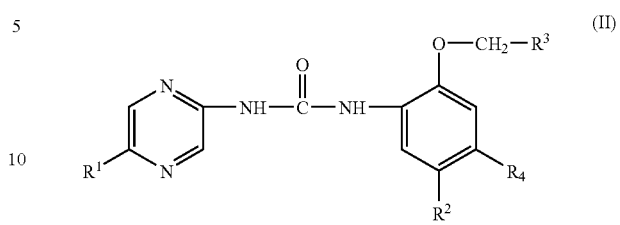

(II)

wherein $R^1$ is halo, $C_{1-3}$alkyl, CN, or $CF_3$;

$R^2$ is hydrogen, $C_{1-3}$alkyl, CN, $OC_{1-3}$alkyl, halo, or $N(R^b)_2$ wherein $R^b$, independently, is hydrogen or $C_{1-3}$alkyl;

$R^3$ is a 6- or 7-membered saturated heterocyclic ring containing one ring N—$R^a$ group and either a second ring N—$R^a$ group, a ring oxygen, or a ring sulfur, wherein $R^a$, independently, is hydrogen, $C_{1-3}$alkyl, or $CH_2CN$, and wherein $R^3$ is optionally substituted with oxo (=O);

$R^4$ is hydrogen, $C_{1-3}$alkyl, $OC_{1-3}$alkyl, or halo;

or $R^2$ and $R^4$ are taken together with the carbons to which they are attached to form a 5- to 7-membered saturated carbocyclic ring, provided that at least one of $R^2$ and $R^4$ is different from hydrogen, or pharmaceutically acceptable salts, prodrugs, or solvates thereof.

In one preferred embodiment of compounds of formulas (I) and (II), $R^1$ is chloro, methyl, CN, or $CF_3$. In another preferred embodiment, $R^2$ is hydrogen, methyl, ethyl, chloro, bromo, dimethylamino, cyano, or methoxy. In more preferred embodiments, $R^2$ is different from hydrogen.

In other preferred embodiments of formulas (I) and (II), $R^4$ is methyl, chloro, fluoro, methoxy, isopropoxy, dimethylamino, —$SCH_3$, —$NHC(=O)CH(CH_3)_2$, —$NHC(=O)CH_3$, pyrrolidinyl, or 3,3-dimethyl-pyrrolidinyl. In more preferred embodiments, $R^4$ is methyl, chloro, or methoxy. In still another preferred embodiment, $R^2$ and $R^4$ are taken together with the carbons to which they are attached to form a five-membered or a six-membered, saturated carbocyclic ring.

In still another preferred embodiment of formulas (I) and (II), when $R^5$ is halo, $R^4$ is hydrogen. In a preferred embodiment, $R^5$ is fluoro. In more preferred embodiments, $R^5$ is hydrogen.

In one embodiment of formulas (I) and (II), when $R^1$ is cyano, $R^2$ is hydrogen and $R^4$ preferably is chloro or methyl. In another embodiment, $R^5$ is fluoro, $R^4$ is hydrogen, and $R^2$ is methyl, chloro, or bromo.

Examples of preferred $R^3$ groups in formulas (I) and (II) include, but are not limited to,

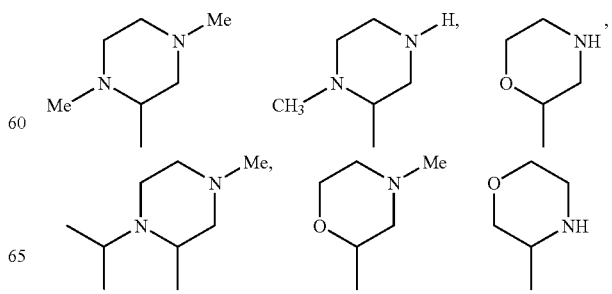

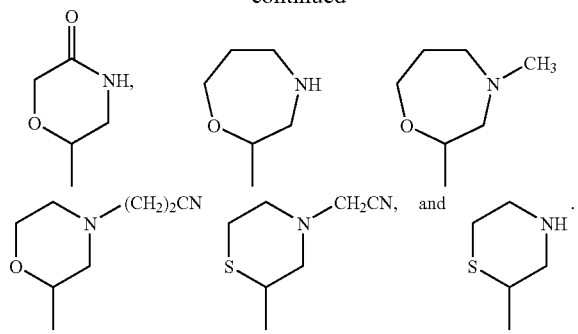

As used herein, the term "$C_{1-3}$alkyl" includes straight chain and branched alkyl groups containing one to three carbon atoms, i.e., methyl, ethyl, n-propyl, and isopropyl.

"Halo" is defined herein as fluoro, chloro, bromo, and iodo.

"Cyano" is defined as —CN.

"Trifluoromethyl" is defined to mean —$CF_3$.

The abbreviation "Me" is methyl, i.e., —$CH_3$.

DNA-damaging agents that activate cell cycle checkpoints generally are referred to herein as "checkpoint activators." DNA-damaging agents that activate the checkpoint designated "Chk1" (pronounced "check-one") are referred to herein as "Chk1 activators." Likewise, inhibitors of such checkpoints are referred to herein as "checkpoint inhibitors" and "Chk1 inhibitors," respectively.

As used herein, Chk1 inhibitors are compounds that are capable of at least partially abrogating at least one cell cycle checkpoint activity of the Chk1 protein. Abrogation of a cell cycle checkpoint is achieved when the cellular checkpoint mechanism is overcome sufficiently to allow the cell to pass from the cell cycle phase in which it is halted to the next phase in the cell cycle or to allow the cell to pass directly to cell death. Abrogation of a cell cycle checkpoint permits cells to carry damaged or imperfect genetic material to subsequent cell cycle phases, thereby inducing or promoting cell death. Cell death can occur by any mechanism, including apoptosis and mitotic catastrophe. The compounds of the invention are Chk1 inhibitors.

Chk1 activator includes any known or after-discovered agent having the ability to activate Chk1 kinase activity, and thus induce at least partial cell cycle arrest. Chk1 activators include agents capable of arresting the cell cycle at any phase of the cell cycle, which phase may be referred to herein as the "target phase" for that activator. Target phases include any of the cell cycle phases except mitosis, i.e., any of the G1, S, and G2 phases. Chk1 activators useful in the invention include DNA damaging agents, such as chemotherapeutic agents and/or radiation. Radiation Chk1 activators include, but are not limited to, ionizing radiation. Ionizing radiation includes electromagnetic or particulate radiation capable of producing ion pairs by interacting with matter. Ionizing radiation includes x and gamma rays, alpha and beta particles, neutrons and charged nuclei. Radioation includes ultraviolet light, visible light, infrared radiation, microwave radiation, and mixtures thereof. Assays such as that described in Example 8 can be used to determine whether an agent is a Chk1 activator.

"Inhibiting aberrant cell proliferation" means retarding the rate at which aberrantly proliferating cells proliferate or eliminating such proliferation altogether. This inhibition can result either from a decreased rate of replication, an increased rate of cell death, or both. Cell death can occur by any mechanism, including apoptosis and mitotic catastrophe.

"Preventing aberrant cell proliferation" means inhibiting aberrant cell proliferation prior to occurrence, or inhibiting the recurrence thereof.

"In vivo" means within a living subject, as within an animal or human. In this context, agents can be used therapeutically in vivo to retard or eliminate the proliferation of aberrantly replicating cells. The agents also can be used in vivo as a prophylactic to prevent aberrant cell proliferation or the manifestation of symptoms associated therewith.

"Ex vivo" means outside a living subject. Examples of ex vivo cell populations include cell cultures and biological samples such as fluid or tissue samples from humans or animals. Such samples can be obtained by methods well known in the art. Exemplary biological fluid samples include blood, cerebrospinal fluid, urine, saliva. Exemplary tissue samples include tumors and biopsies. In this context, the present compounds can be in numerous applications, both therapeutic and experimental.

"Radiosensitizer," as used herein, means a compound, administered to a human or other animal in a therapeutically effective amount to increase the sensitivity of cells to electromagnetic radiation and/or to promote the treatment of diseases treatable with electromagnetic radiation.

"Radiation" as used herein includes, but is not limited to, radiation having wavelengths in the range of $10^{-20}$ to 100 meters.

The term "container" means any receptacle and closure therefor suitable for storing, shipping, dispensing, and/or handling a pharmaceutical product.

The term "package insert" means information accompanying the product that provides a description of how to administer the product, along with the safety and efficacy data required to allow the physician, pharmacist, and patient to make an informed decision regarding use of the product. The package insert generally is regarded as the "label" for a pharmaceutical product.

The present invention includes all possible stereoisomers and geometric isomers of the compounds of structural formula (I) or (II). The present invention includes not only racemic compounds, but optically active isomers as well. When a compound of structural formula (I) or (II) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), 883-888 (1997). Resolution of the final product, an intermediate, or a starting material can be achieved by any suitable method known in the art. Additionally, in situations where tautomers of the compounds of structural formula (I) or (II) are possible, the present invention is intended to include all tautomeric forms of the compounds. As demonstrated below, specific stereoisomers can exhibit an exceptional ability to inhibit Chk1 in combination with chemotherapeutic or radiotherapeutic treatments.

Prodrugs of compounds of structural formula (I) or (II) also can be used as the compound in a method of the present invention. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., *Med. Res. Rev.*, 15, 83 (1995)).

Compounds of the present invention contain one or more functional groups. The functional groups, if desired or necessary, can be modified to provide a prodrug. Suitable prodrugs include, for example, acid derivatives, such as amides and esters. It also is appreciated by those skilled in the art that N-oxides can be used as a prodrug.

Compounds of the invention can exist as salts. Pharmaceutically acceptable salts of the compounds of the invention generally are preferred in the methods of the invention. As used herein, the term "pharmaceutically acceptable salts" refers to salts or zwitterionic forms of the compounds of structural formula (I) or (II). Salts of compounds of formula (I) or (II) can be prepared during the final isolation and purification of the compounds or separately by reacting the compound with an acid having a suitable cation. Suitable pharmaceutically acceptable cations include alkali metal (e.g., sodium or potassium) and alkaline earth metal (e.g., calcium or magnesium) cations. In addition, the pharmaceutically acceptable salts of compounds of structural formula (I) or (II) that contain a basic center are acid addition salts formed with pharmaceutically acceptable acids. Examples of acids which can be employed to form pharmaceutically acceptable salts include inorganic acids such as hydrochloric, hydrobromic, sulfuric, and phosphoric, and organic acids such as oxalic, maleic, succinic, malonic, and citric. Nonlimiting examples of salts of compounds of the invention include, but are not limited to, hydrochloride, hydrobromide, hydroiodide, sulfate, bisulfate, 2-hydroxyethansulfonate, phosphate, hydrogen phosphate, acetate, adipate, alginate, aspartate, benzoate, butyrate, camphorate, camphorsulfonate, citrate, digluconate, glycerolphsphate, hemisulfate, heptanoate, hexanoate, formate, succinate, malonate, fumarate, maleate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, glutamate, bicarbonate, paratoluenesulfonate, undecanoate, lactate, citrate, tartrate, gluconate, benzene sulphonate, and p-toluenesulphonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I) or (II) as well as pharmaceutically acceptable salts, solvates, or prodrugs thereof.

Nonlimiting examples of compounds of the present invention are:

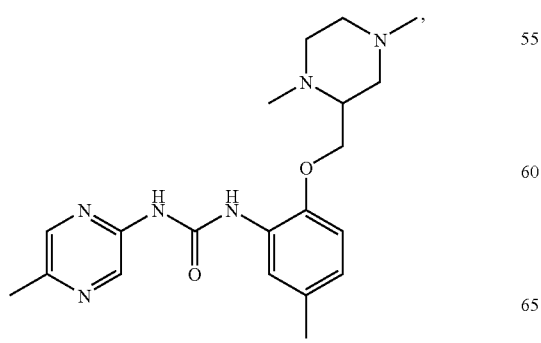

-continued

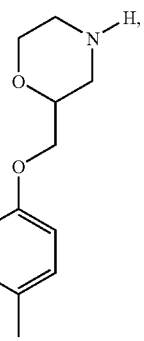

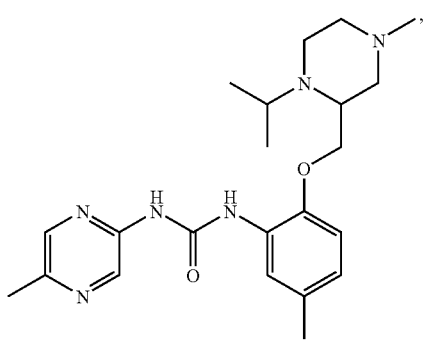

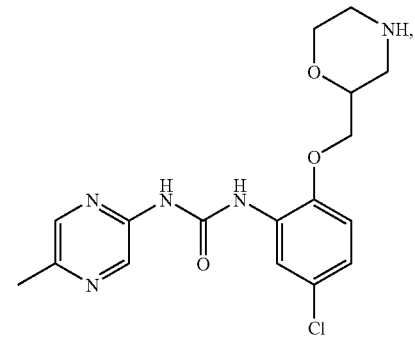

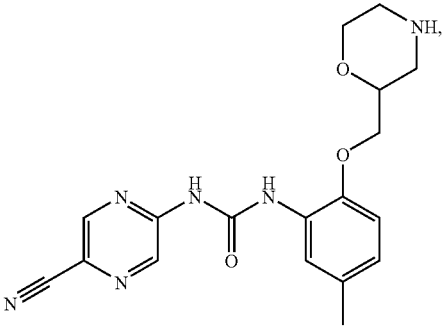

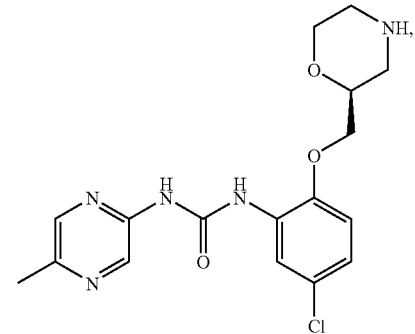

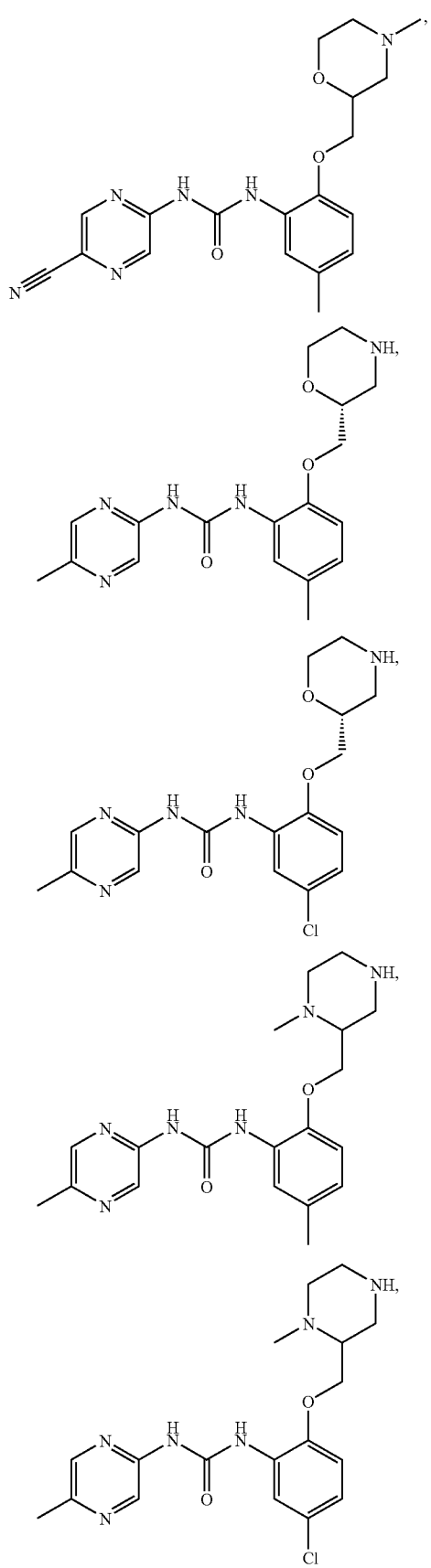
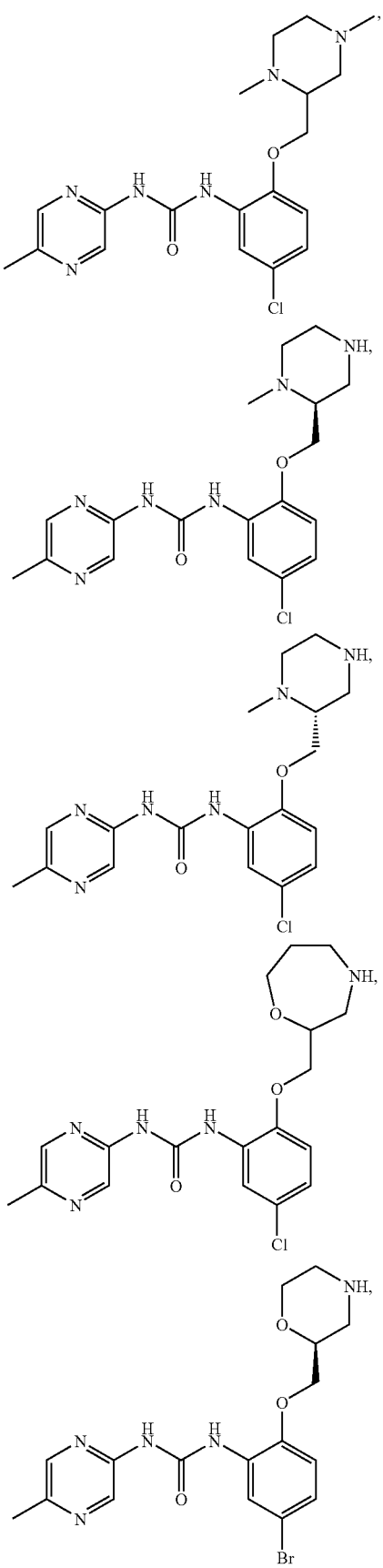

-continued
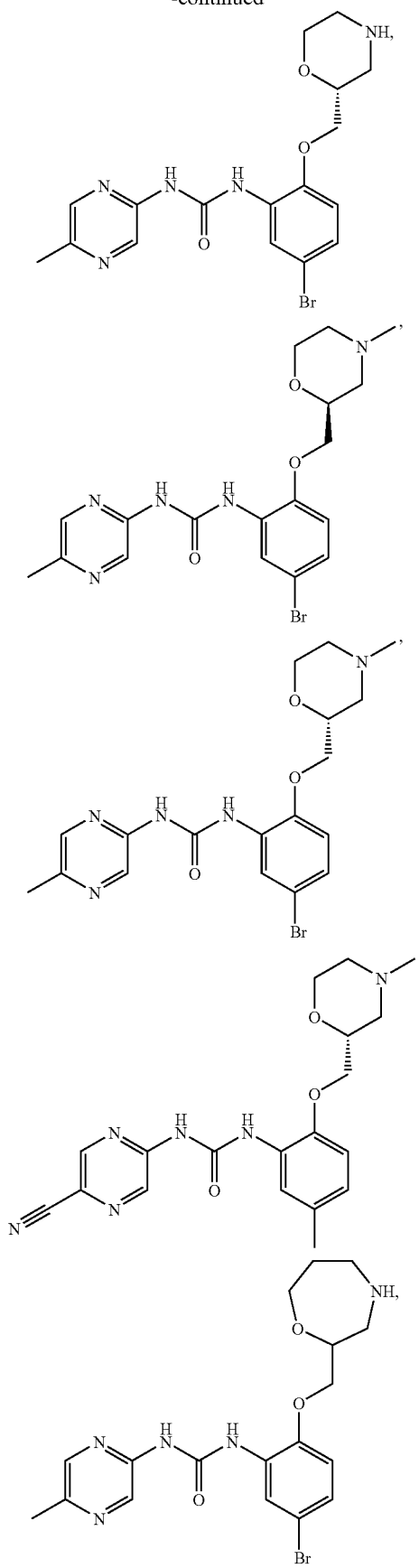
-continued
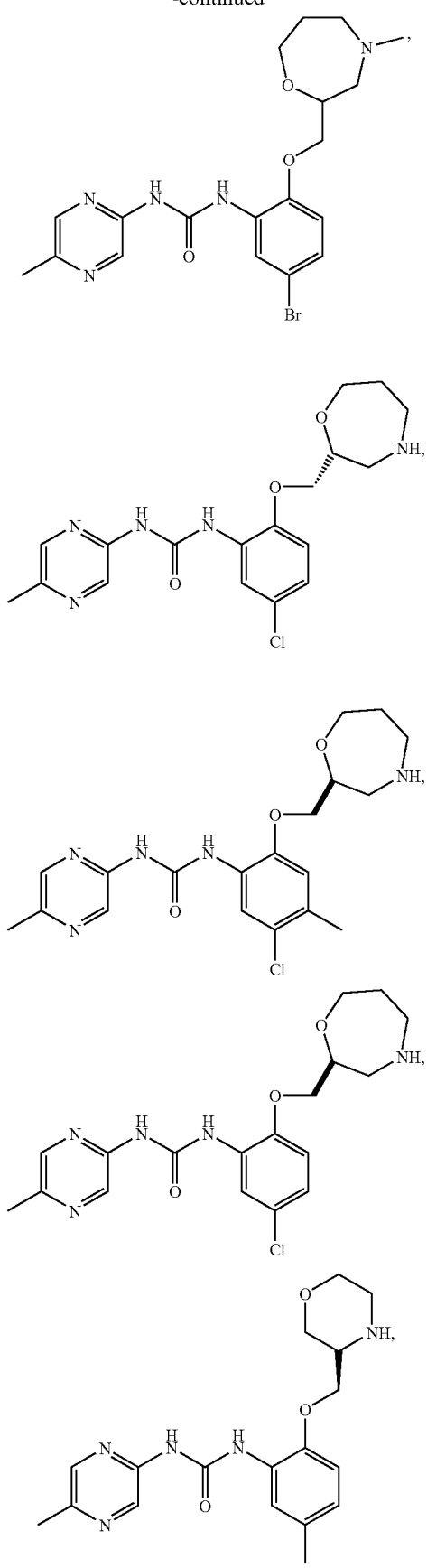

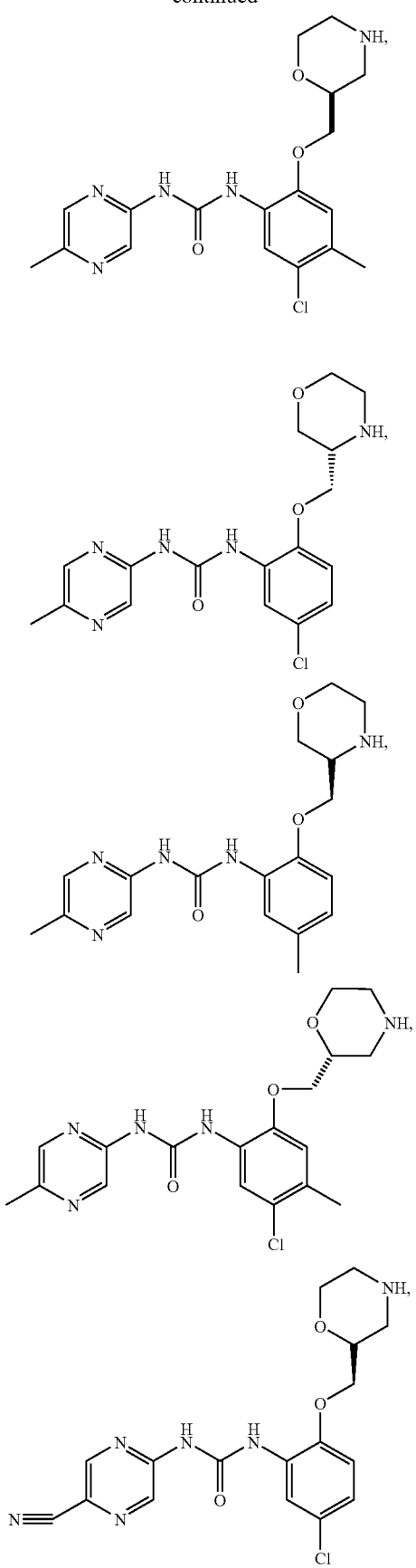
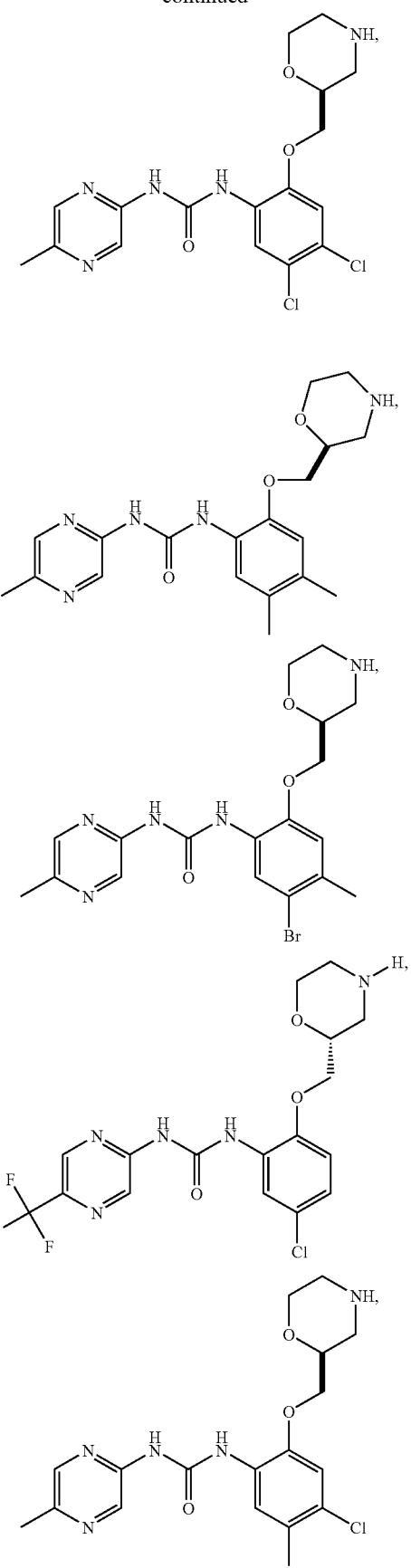

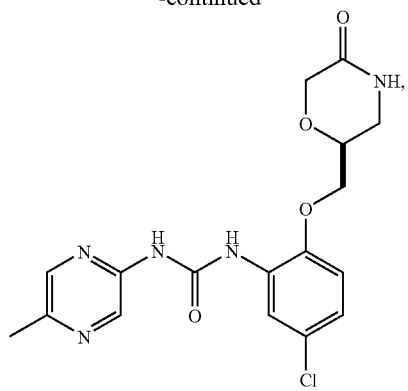
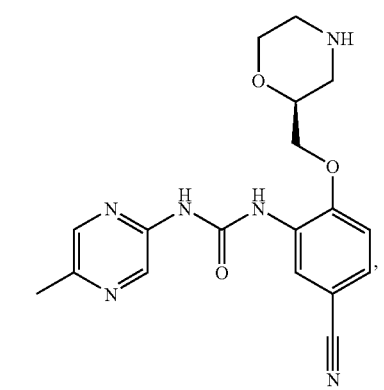
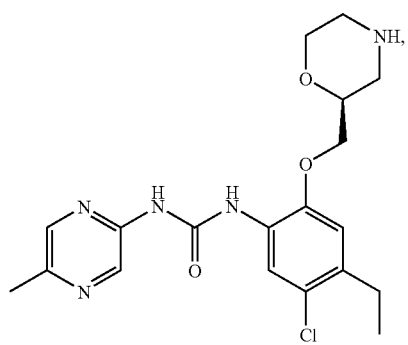
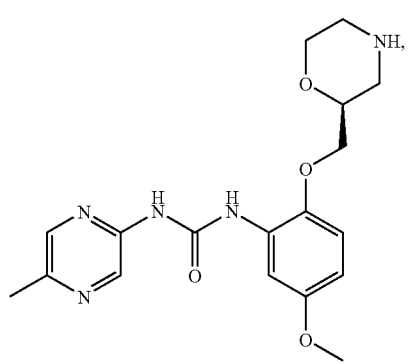
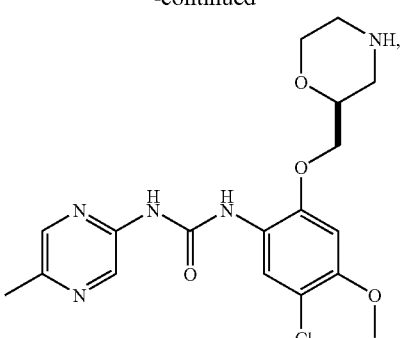
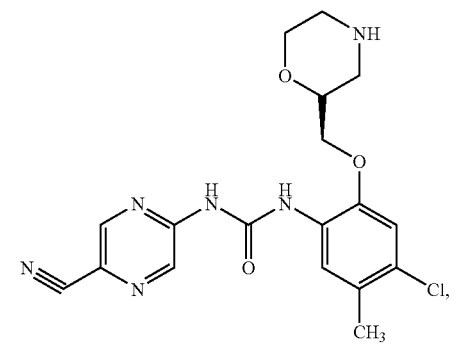
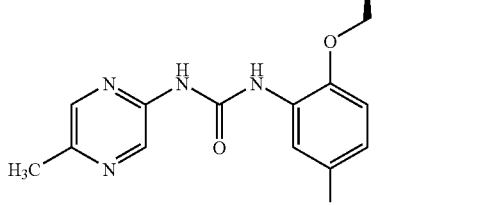
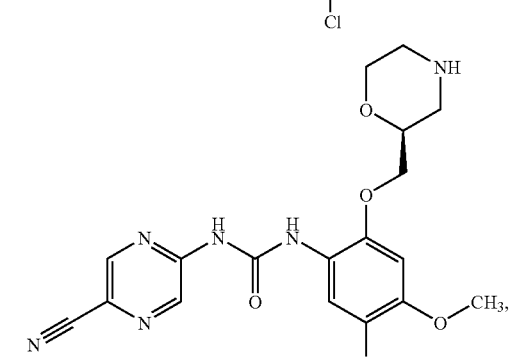
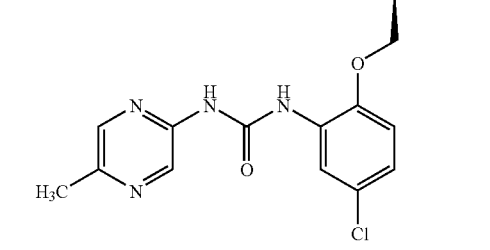

-continued
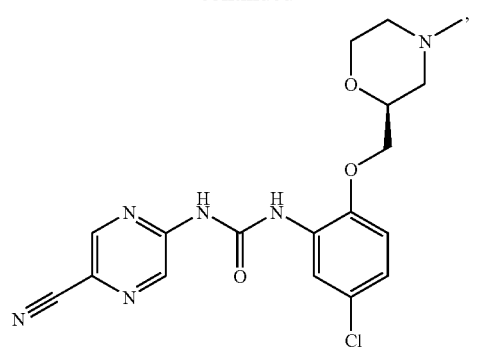
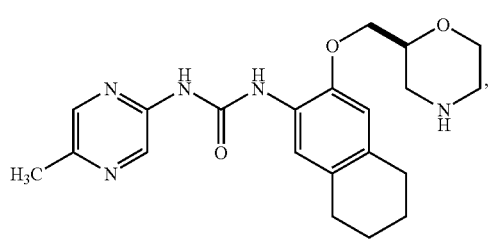
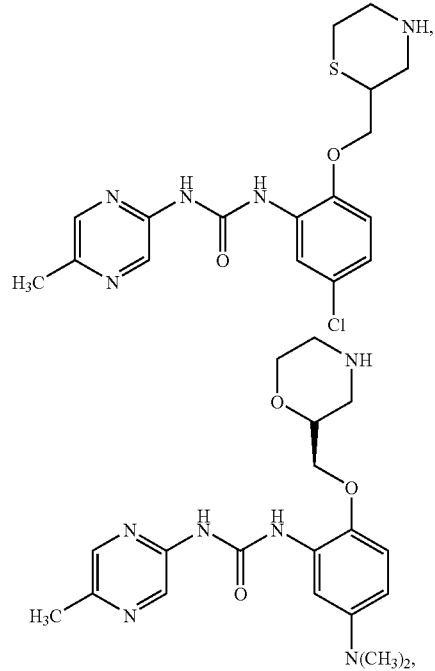
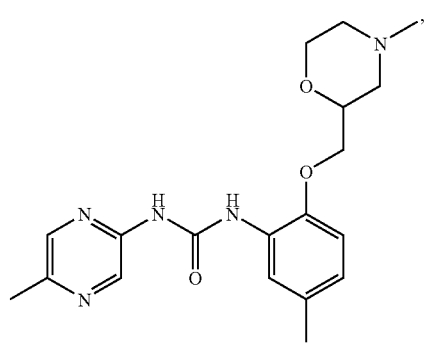
1-[5-methyl-2-(4-methyl-morpholin-2-ylmethoxy)-phenyl]-3-(5-methylpyrazin-2-yl)-urea
(LRMS (ES, positive) m/e–372.4)
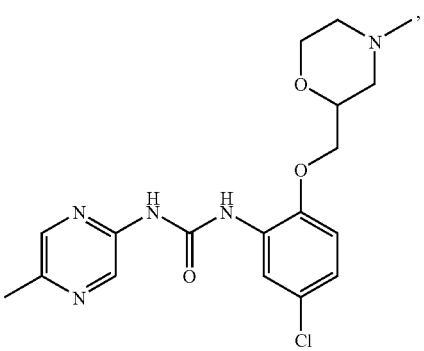
1-[5-chloro-2-(4-methyl-morpholin-2-ylmethoxy)-phenyl]-3-(5-methyl-pyrazin-2-yl)-urea
(LRMS (ES, positive) m/e–392.4)
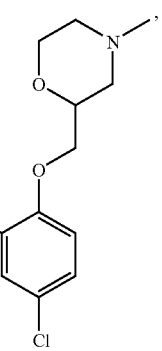
1-(5-cyano-pyrazin-2-yl)-3-[2-(1,4-dimethyl-piperazin-2-ylmethoxy)-5-methyl-phenyl]-urea
(LRMS (ES, positive) m/e–396.4)
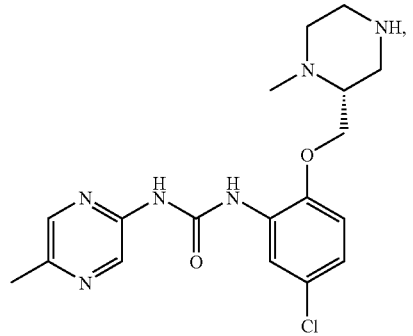

23

1-[5-chloro-2-R-(1-methyl-piperazin-2-ylmethoxy)-phenyl]-3-(5-methyl-pyrazin-2-yl)-urea (LRMS (ES, positive) m/e–391.3)

24

1-[5-chloro-2-(4-methyl-[1,4]oxazepan-2-yl-methoxy)-phenyl]-3-(5-methyl-pyrazin-2-yl)-urea (LRMS (ES, positive) m/e–406.0)

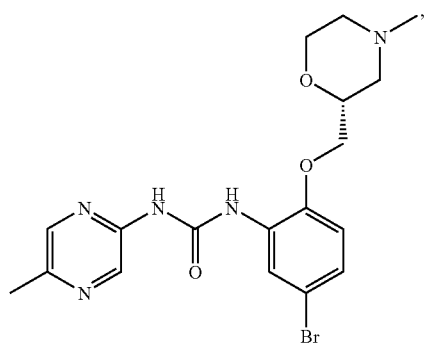

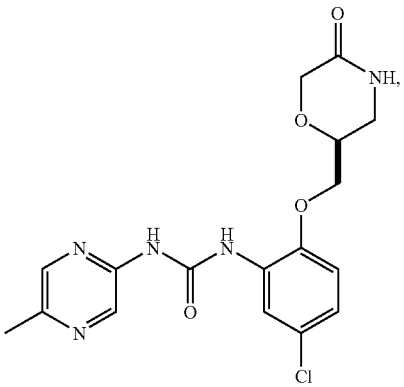

1-[5-bromo-2-R-(4-methyl-morpholin-2-ylmethoxy)-phenyl]-3-(5-methyl-pyrazin-2-yl)-urea (LRMS (ES, positive) m/e–438.0)

1-[5-chloro-2-S-(5-oxo-morpholin-2-ylmethoxy)-phenyl]-3-(5-methyl-pyrazin-2-yl)-urea (LRMS (ES, positive) m/e–392.2)

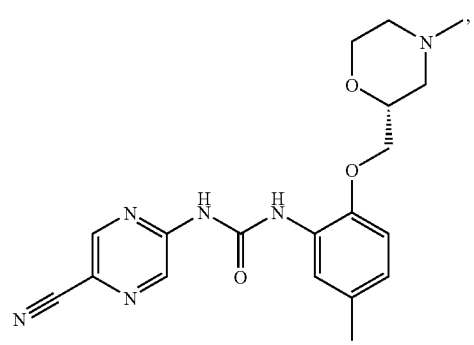

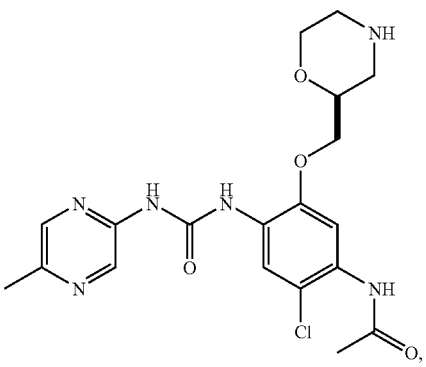

1-(5-cyano-pyrazin-2-yl)-3-[5-methyl-2-R-(4-methyl-morpholin-2-ylmethoxy)-phenyl]-urea (LRMS (ES, positive) m/e–383.0)

N-[2-chloro-4-[3-(5-methyl-pyrazin-2-yl)-ureido]-5-(S-morpholin-2-ylmethoxy)-phenyl]-acetamide (LRMS (ES, positive) m/e–435.0)

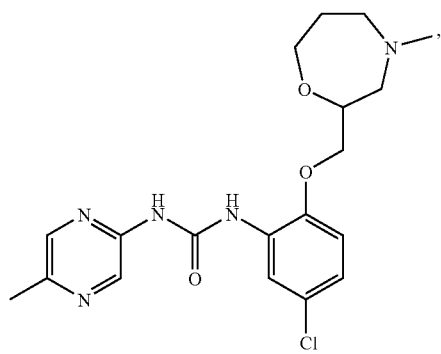

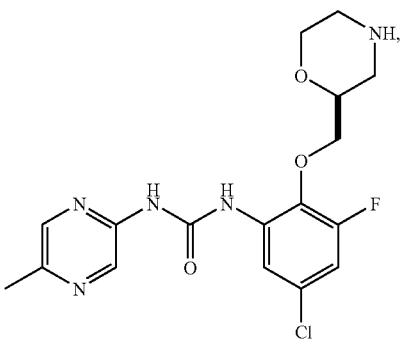

1-[5-chloro-3-fluoro-2-(S-morpholin-2-ylmethoxy)-phenyl]-3-(5-methyl-pyrazin-2-yl)-urea (LRMS (ES, positive) m/e−396.3)

1-[4-chloro-2-(S-morpholin-2-ylmethoxy)-phenyl]-3-(5-methyl-pyrazin-2-yl)-urea (LRMS (ES, positive) m/e−378.3)

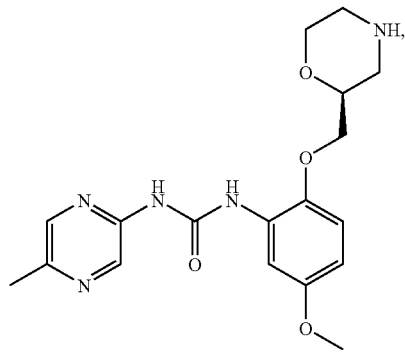

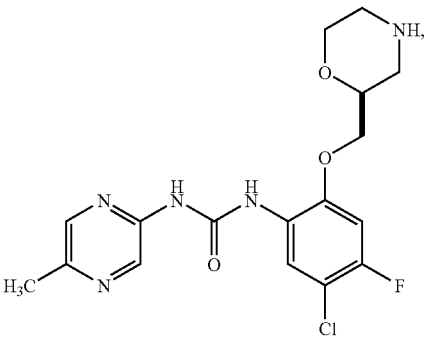

1-[5-methoxy-2-(S-morpholin-2-ylmethoxy)-phenyl]-3-(5-methyl-pyrazin-2-yl)-urea (LRMS (ES, positive) m/e−374.3)

1-[5-chloro-4-fluoro-2-(S-morpholin-2-ylmethoxy)-phenyl]-3-(5-methyl-pyrazin-2-yl)-urea (LRMS (ES, positive) m/e−396.1)

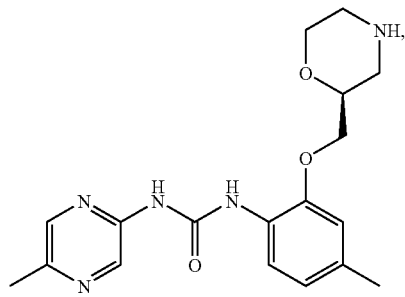

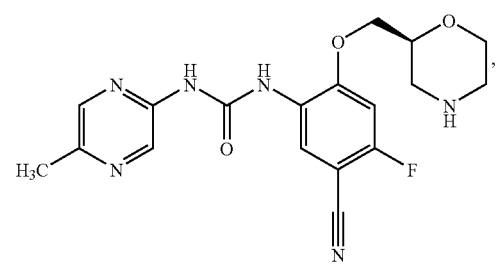

1-[5-methoxy-2-(S-morpholin-2-ylmethoxy)-phenyl]-3-(5-methyl-pyrazin-2-yl)-urea (LRMS (ES, positive) m/e−358.3)

1-[5-cyano-4-methyl-2-(S-morpholin-2-ylmethoxy)-phenyl]-3-(5-methyl-pyrazin-2-yl)-urea (LRMS (ES, positive) m/e−383.3)

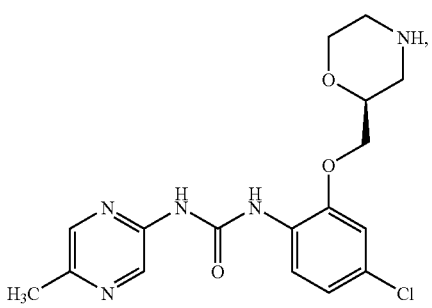

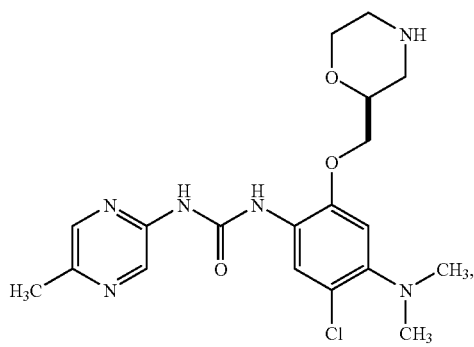

27

1-[5-chloro-4-dimethylamino-2-(S-morpholin-2-ylmethoxy)-phenyl]-3-(5-methyl-pyrazin-2-yl)-urea (LRMS (ES, positive) m/e–421.2)

28

1-[5-chloro-2-(4-cyanomethyl-thiomorpholin-2-yl-methoxy)-phenyl]-3-(5-methyl-pyrazin-2-yl)-urea (LRMS (ES, positive) m/e–433.0)

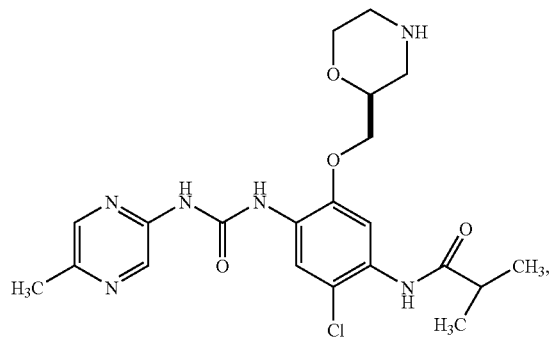

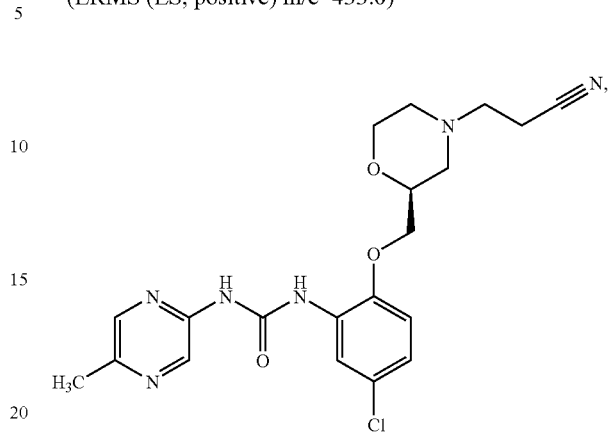

N-[2-chloro-4-[3-(5-methyl-pyrazin-2-yl)-ureido]-5-(S-morpholin-2-ylmethoxy)-phenyl]-isobutyramide (LRMS (ES, positive) m/e–463.2)

1-{5-chloro-2-[4-(2-cyano-ethyl)-S-morpholin-2-ylmethoxy]-phenyl}-3-(5-methyl-pyrazin-2-yl)-urea (LRMS (ES, positive) m/e–431.0)

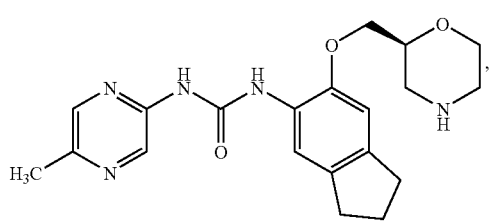

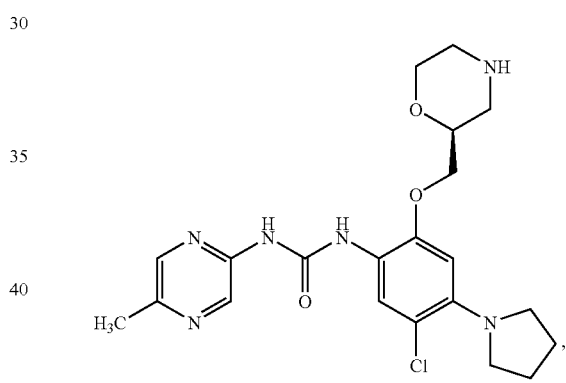

1-(5-methyl-pyrazin-2-yl)-3-[6-(S-morpholin-2-ylmethoxy)-indan-5-yl]-urea (LRMS (ES, positive) m/e–384.3)

1-[5-chloro-2-(S-morpholin-2-ylmethoxy)-4-pyrrolidin-1-yl-phenyl]-3-(5-methyl-pyrazin-2-yl)-urea (LRMS (ES, positive) m/e–447.2)

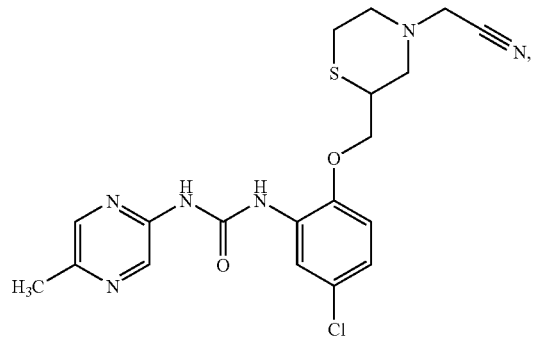

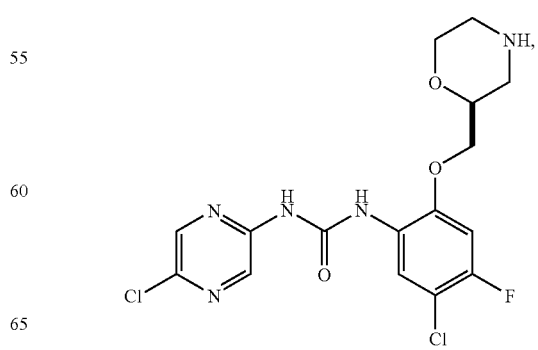

-continued

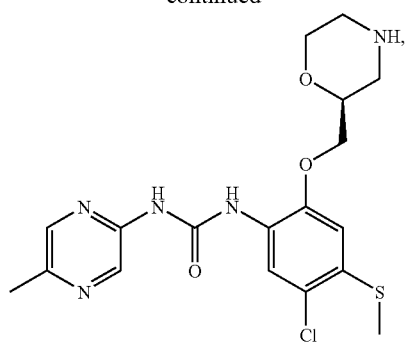

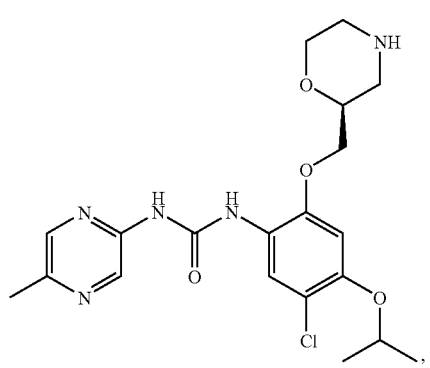

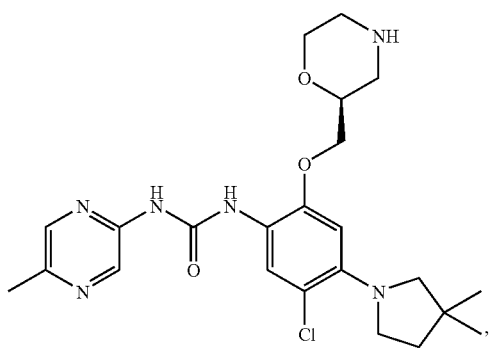

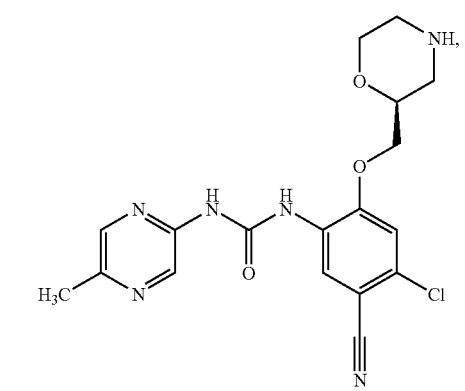

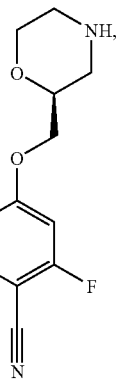

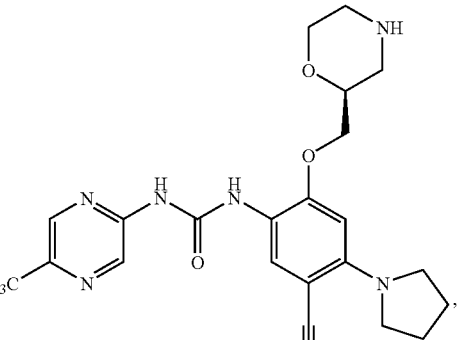

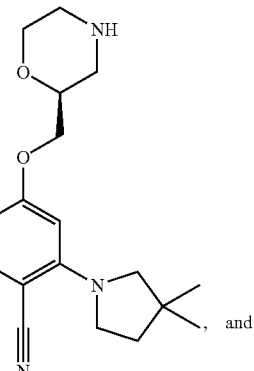

, and

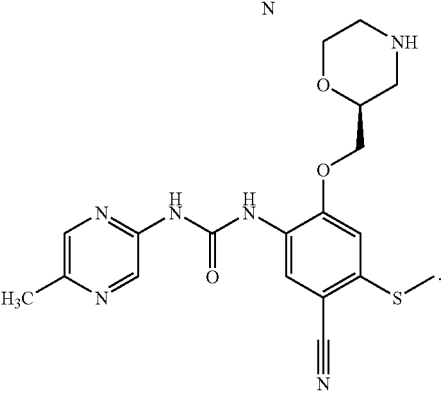

or salts, solvates (e.g., hydrates), or prodrugs thereof.

The compounds of the present invention can be therapeutically administered as the neat chemical, but it is preferable to administer the compounds as a pharmaceutical composition or formulation. Thus, the present invention provides a pharmaceutical composition comprising a compound of the formula (I) or (II) together with a pharmaceutically acceptable diluent or carrier therefor. Also provided is a process of preparing a pharmaceutical composition comprising admixing a compound of formula (I) or (II) with a pharmaceutically acceptable diluent or carrier therefor.

Accordingly, the present invention further provides pharmaceutical formulations comprising a compound of structural formula (I) or (II), or a pharmaceutically acceptable salt, prodrug, or solvate thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

Compounds of the invention exhibit unexpectedly high potency. Potency typically is expressed as the concentration of a compound required to achieve a certain result. The greater the potency, the less compound required to perform its intended function. In vitro potency typically is expressed in terms of $IC_{50}$ values and measured using a dose-response assay. $IC_{50}$ values can be measured by contacting a sensitive assay system with a compound of interest over a range of concentrations, including concentrations at which no or minimal effect is observed, through higher concentrations at which partial effect is observed, to saturating concentrations at which a maximum effect is observed. Theoretically, such assays of the dose-response effect of inhibitor compounds can be described as a sigmoidal curve expressing a degree of inhibition as a function of concentration when plotted on a log scale. The curve also theoretically passes through a point at which the concentration is sufficient to reduce activity of the checkpoint enzyme to a level that is 50% that of the difference between minimal and maximal enzyme activity observed in the assay. This concentration is defined as the Inhibitory Concentration at 50% inhibition or $IC_{50}$ value.

$IC_{50}$ values can be determined using conventional biochemical (acellular) assay techniques or cell-based assay techniques well known to those of ordinary skill in the art. An example of such an assay is provided in Example 1 below.

Preferably, $IC_{50}$ values are obtained by performing the relevant assay at least twice, with the $IC_{50}$ value expressed as the average (arithmetic mean, or "mean") of the individual values obtained. More preferably, the assay is repeated from 3 to 10 (or more) times, with the $IC_{50}$ value expressed as the mean of the values obtained. Most preferably, the assay is performed a number of times sufficient to generate a statistically reliable mean $IC_{50}$ value, using statistical methods known to those of ordinary skill in the art.

Compounds of the invention exhibit unexpectedly low $IC_{50}$ values, corresponding to unexpectedly high in vitro potency. Compounds of the invention, when assayed as described in Example 1 below, exhibit $IC_{50}$ values of less than about 200 nM, in some embodiments less than about 150 nM, in other embodiments less than about 100 nM, in others less than about 50 nM, in others less than about 10 nM, and in others less than about 5 nM. In other embodiments, the compounds of the invention exhibit $IC_{50}$ values from about 0.1 nM to about 5 nM.

Compounds of the invention exhibit selectivity for inhibiting Chk1 over other protein kinases. Selectivity may be advantageous in reducing adverse side effects and/or increasing therapeutic index.

"Selectivity" is expressed herein as "fold selectivity." In general, fold selectivity, as used herein, is the $IC_{50}$ of a test compound for a comparison enzyme divided by the $IC_{50}$ of a comparator enzyme. In particular, fold selectivity for a Chk1 inhibitor, as used herein, is the $IC_{50}$ of a Chk1 inhibitor (a test compound) for Chk1 (the comparison enzyme) divided by the $IC_{50}$ for a comparator enzyme. Comparator enzymes against which compounds of the invention may be measured include at least the following protein kinases: Cdc2, Chk2, CTAK, EphA1, EphA2, Erk1, FGFR1, FGFR4, IR, JNK1, c-Kit, p38alpha, p38beta, p38delta, Ros, Rse, Rsk2, TrkA, TrkB, protein kinas A, protein kinas C, pp 60v-src, protein kinase B/Akt-1, p38MapK, p70S6K, calcium calmodulin-dependent kinase II, and ab1 tyrosine kinase.

Assays for determining $IC_{50}$ values for a test compound against a comparator enzyme are described in Example 2 and are well known to those of ordinary skill in the art. Compounds of the invention exhibit at least about 20-fold selectivity over the aforementioned protein kinases tested. In some embodiments, Chk1 inhibitors of the present invention exhibit at least about 50-fold selectivity, in other embodiments at least about 75-fold selectivity, in other embodiments at least about 100-fold selectivity in inhibiting Chk1 over the aforementioned protein kinases tested.

The compounds of the invention exhibit unexpectedly high potency in a cell-based assay. To measure cell-based potency of a Chk1 inhibitor, an assay was developed that allows one to measure the concentration of Chk1 inhibitor required to increase the growth-inhibiting effects of a DNA damaging agent in a cell-based model involving aberrantly proliferating cells. This measure of cell-based potency is expressed herein as an "$EC_{TFS}$" value, where "$EC_{TFS}$" is the Effective Concentration of Chk1 inhibitor that produces a Two-Fold Sensitization of a population of aberrantly proliferating cells to the growth-inhibiting effects of a DNA damaging agent. $EC_{TFS}$ is calculated to be the concentration of Chk1 inhibitor that reduces the amount of DNA damaging agent required for 90% inhibition of cell growth by half. Applicants have found that the compounds of the invention exhibit unexpectedly low $EC_{TFS}$ values, corresponding to unexpectedly high cell-based potency.

Another parameter that may be measured is the fold sensitization achieved at the $LD_{50}$ (the dose of compound alone that inhibits growth of 50% of cells) for the Chk1 inhibitor compound. These two values, $EC_{TFS}$ and fold sensitization at the $LD_{50}$, allow direct ranking of both the potency and toxicity of Chk1 inhibitors with respect to one another.

An example of an assay useful to measure $EC_{TFS}$ values is described in Example 3 below. Briefly, this assay uses HT29 human colon carcinoma cells as the population of aberrantly proliferating cells, gemcitabine as the DNA damaging agent/Chk1 activator, and a compound of the invention as the Chk1 inhibitor. The population of aberrantly proliferating cells is cultured and allowed to grow in a suitable growth medium. Subsequently, the cells are subjected to the DNA damaging agent over a range of concentrations. After a predetermined amount of time, the DNA damaging agent is removed, and the cells are subjected to a Chk1 inhibitor over a range of concentrations and for a predetermined period of time. The plates of cultured cells then are harvested and the relative number of surviving cells is counted. The data is normalized against Chk1 inhibitor alone as control, and then plotted on a log/log graph of DNA damaging agent concentration vs. relative cell survival (100% equaling 1.0). The fold sensitization is derived from the difference between the amount of DNA damaging agent required to achieve 90% growth inhibition with and without Chk1 inhibitor for each concentration of Chk1 inhibitor used. These data then are plotted on a graph of Chk1 inhibitor concentration vs. fold sensitization, from which $EC_{TFS}$ is calculated.

Preferably $EC_{TFS}$ values are obtained by performing the assay at least twice, with the $EC_{TFS}$ value expressed as the mean of the individual values obtained. More preferably, the assay is repeated from 3 to 10 (or more) times, with the $EC_{TFS}$ value expressed as the mean of the values obtained. Most preferably, the assay is performed a number of times necessary to generate a statistically reliable mean $EC_{TFS}$ value, using statistical methods known to those of ordinary skill in the art.

All compounds that were subject to an $EC_{TFS}$ assay exhibited $EC_{TFS}$ values of less than about 1000 nM. In contrast, structurally similar compounds that are previously known exhibit $EC_{TFS}$ values of about 11,000 nM. In some embodiments, compounds of the present invention exhibit $EC_{TFS}$ values of less than about 500 nM, in others less than about 300 nM, in others less than about 200 nM, in others less than about 150 nM, in others less than about 100 nM, in others less than abut 50 nM, in others less than about 30 nM, and in others less than about 20 nM, or less than about 10 nM, or in other embodiments less than about 5 nM.

Compounds and pharmaceutical compositions suitable for use in the present invention include those wherein the active ingredient is administered in an effective amount to achieve its intended purpose. More specifically, a "therapeutically effective amount" means an amount sufficient to treat an individual suffering an indication, or to alleviate the existing symptoms of the indication. Determination of a therapeutically effective amount is well within the capability of those skilled in the art, especially in light of the detailed disclosure provided herein.

In addition to the Chk1 inhibitor, pharmaceutical compositions of the invention can be formulated to include biologically active agents, such as cytokines, lymphokines, growth factors, other hematopoietic factors, or mixtures thereof, to reduce adverse side effects that can arise from, or be associated with, administration of the pharmaceutical composition alone. Alternatively, such biologically active agents may be included in the pharmaceutical composition of the invention to promote a desired therapeutic effect. Adjuvant biologically active agents useful in pharmaceutical compositions of the invention include, but are not limited to, M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNF, G-CSF, Meg-CSF, GM-CSF, thrombopoietin, stem cell factor, erythropoietin, angiopoietins, including Ang-1, Ang-2, Ang-4, Ang-Y, and/or the human angiopoietin-like polypeptide, vascular endothelial growth factor (VEGF), angiogenin, bone morphogenic protein-1 (BMP-1), BMP-2, BMP-3, BMP-4, BMP-5, BMP-6, BMP-7, BMP-8, BMP-9, BMP-10, BMP-11, BMP-12, BMP-13, BMP-14, BMP-15, BMP receptor IA, BMP receptor IB, brain derived neurotrophic factor, ciliary neutrophic factor, ciliary neutrophic factor receptor cytokine-induced neutrophil chemotactic factor 1, cytokine-induced neutrophil chemotactic factor 2, cytokine-induced neutrophil chemotactic factor 2, endothelial cell growth factor, endothelin 1, epidermal growth factor, epithelial-derived neutrophil attractant, fibroblast growth factor (FGF) 4, FGF 5, FGF 6, FGF 7, FGF 8, FGF 8b, FGF 8c, FGF 9, FGF 10, FGF acidic, FGF basic, glial cell line-derived neutrophic factor receptor 1, glial cell line-derived neutrophic factor receptor 2, growth related protein, growth related protein, growth related protein, growth related protein, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor, platelet derived growth factor receptor, pre-B cell growth stimulating factor, stem cell factor, stem cell factor receptor, transforming growth factor (TGF), TGF, TGF 1, TGF 1.2, TGF 2, TGF 3, TGF 5, latent TGF 1, TGF, binding protein I, TGF binding protein II, TGF binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

The compounds of structural formulae (I) and (II) also can be conjugated or linked to auxiliary moieties that promote a beneficial property (or mitigate an undesirable property) of the compounds in a method of therapeutic use. Such conjugates can enhance delivery of the compounds to a particular anatomical site or region of interest (e.g., a tumor), enable sustained therapeutic concentrations of the compounds in target cells, alter pharmacokinetic and pharmacodynamic properties of the compounds, and/or improve the therapeutic index or safety profile of the compounds. Suitable auxiliary moieties include, for example, amino acids, oligopeptides, or polypeptides, e.g., antibodies such as monoclonal antibodies and other engineered antibodies; and natural or synthetic ligands to receptors in target cells or tissues. Other suitable auxiliaries include fatty acid or lipid moieties that promote biodistribution and/or uptake of the compound by target cells (see, e.g., Bradley et al., *Clin. Cancer Res.* 7:3229, 2001).

Formulations of the present invention can be administered in a standard manner for the treatment of the indicated diseases, such as orally, parenterally, transmucosally (e.g., sublingually or via buccal administration), topically, transdermally, rectally, via inhalation (e.g., nasal or deep lung inhalation). Parenteral administration includes, but is not limited to intravenous, intraarterial, intraperitoneal, subcutaneous, intramuscular, intrathecal, and intraarticular. Parenteral administration also can be accomplished using a high pressure technique, like POWDERJECT™ (Powderject Pharmaceuticals, Plc, Oxford, England).

For oral administration and for buccal administration, the composition can be in the form of tablets or lozenges formulated in conventional manner. For example, tablets and capsules can contain conventional excipients such as binding agents (for example, syrup, acacia, gelatin, sorbitol, tragacanth, mucilage of starch, or polyvinylpyrrolidone), fillers (for example, lactose, sugar, microcrystalline cellulose, maize-starch, calcium phosphate, or sorbitol), lubricants (for example, magnesium stearate, stearic acid, talc, polyethylene glycol or silica), disintegrants (for example, potato starch or sodium starch glycolate), or wetting agents (for example, sodium lauryl sulfate). The tablets can be coated according to methods well known in the art.

Alternatively, compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, for example suspending agents, such as sorbitol syrup, methyl cellulose, glucose/sugar syrup, gelatin, hydroxyethylcellulose, hydroxypropylmethylcellulose, carboxymethylcellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane.

Topical and transdermal formulations comprise conventional aqueous or nonaqueous vehicles, such as eye drops, creams, ointments, lotions, and pastes, or are in the form of a medicated plaster, patch, or membrane.

Additionally, compositions of the present invention can be formulated for administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

A composition of the present invention also can be formulated as a depot preparation. Such long acting formulations can be administered by implantation (for example, subcutaneously or intramuscularly) or by intramuscular injection. Accordingly, the compounds of the invention can be formulated with suitable polymeric materials (e.g., water-soluble polymers) hydrophobic materials (e.g., an emulsion in an acceptable oil), ion exchange resins, or sparingly soluble derivatives (e.g., a sparingly soluble salt).

For veterinary use, a compound of formula (I) or (II), or a pharmaceutically acceptable salt, prodrug, or solvate thereof, is administered as a suitably acceptable formulation in accordance with normal veterinary practice. The veterinarian can readily determine the dosing regimen and route of administration that is most appropriate for a particular animal. Animals treatable by the present compounds and methods include, but are not limited to, pets, livestock, show animals, and zoo specimens.

Synthetic Methods

The compounds of the present invention can be prepared by the following synthetic schemes. First, the alkoxyarylamines used to prepare the Chk1 inhibitors described herein can be prepared by different general synthetic schemes. For example, General Scheme 1 summarizes the reaction of a nitrophenol with an activated form of an alcohol, formed in situ or prepared and isolated independently, to provide a nitrophenyl ether product. Reduction of the ether under standard conditions provides an arylamine that is used to produce a compound of the invention.

General Scheme 1

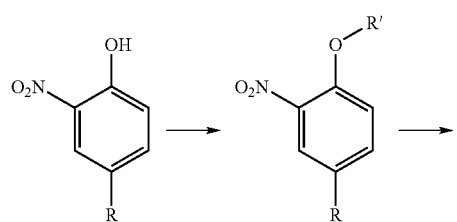

-continued

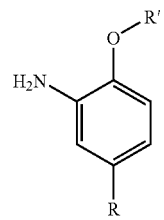

Alternatively, reaction of a halo nitrobenzene with an alcohol in the presence of a strong base, such as sodium hydride or potassium bis(trimethylsilyl)amide, also affords nitroaryl ethers, as illustrated in General Scheme 2. These ethers then are reduced as indicated in General Scheme 1.

General Scheme 2

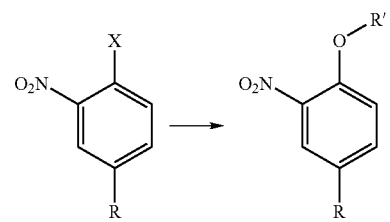

Conversion of an arylamine to a urea can be achieved by one of several synthetic schemes. For example, an arylamine can be reacted with a pyrazine carbamate to yield a urea as illustrated in General Scheme 3.

General Scheme 3

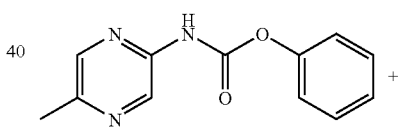

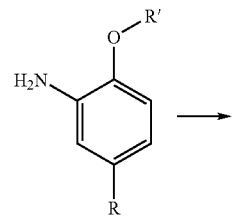

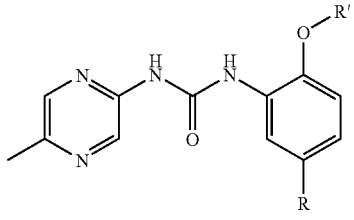

Alternatively, as outlined in General Scheme 4, heat induced decomposition of an acyl azide produces a reactive aryl isocyanate which then is allowed to react with an arylamine to yield the desired urea.

General Scheme 4

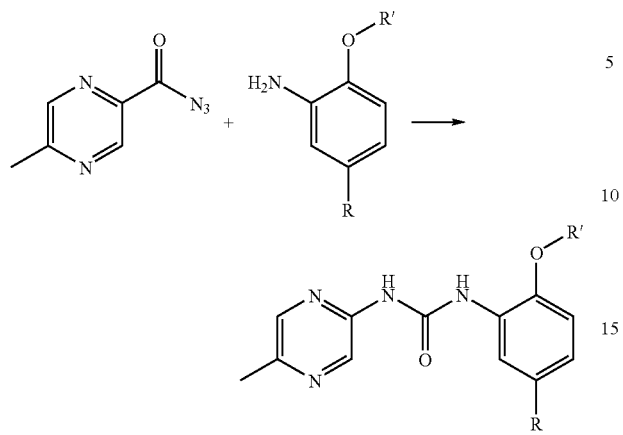

Another approach, illustrated in General Scheme 5, utilizes phosgene or a phosgene equivalent to couple two arylamines and provide a urea.

General Scheme 5

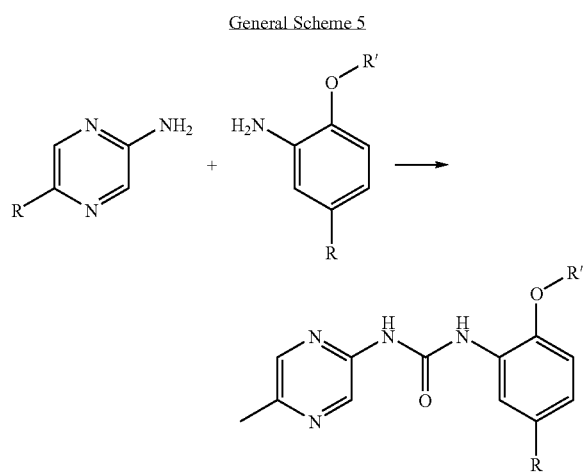

Abbreviations used in the syntheses described herein are: h (h), min (min), pound per square inch (psi), saturated (sat'd), water ($H_2O$), deionized (DI), isopropyl alcohol (iPrOH), platinum on carbon (Pt/C), nitrogen ($N_2$), hydrogen ($H_2$), palladium on carbon (Pd/C), platinum oxide ($Pt_2O$), magnesium sulfate ($MgSO_4$), hydrochloric acid (HCl), diisopropyl azodicarboxylate (DIAD), methylene chloride ($CH_2Cl_2$), chloroform ($CHCl_3$), methanol (MeOH), ammonium hydroxide ($NH_4OH$), tetrahydrofuran (THF), N-methylpyrrolidone (NMP), acetic acid (AcOH), NaOH (NaOH), EtOAc (EtOAc), ethanol (EtOH), dimethyl sulfoxide (DMSO), deuterated dimethyl sulfoxide ($d_6$-DMSO), sodium carbonate ($Na_2CO_3$), deuterated chloroform ($CDCl_3$), sodium bicarbonate ($NaHCO_3$), sodium hydride (NaH), TEA (TEA), cesium carbonate ($Cs_2CO_3$), carbon dioxide ($CO_2$), palladium hydroxide ($Pd(OH)_2$), sulfuric acid ($H_2SO_4$), nitric acid ($HNO_3$), sodium chloride (NaCl), sodium sulfate ($Na_2SO_4$), and dimethylformamide (DMF).

Preparation of Compounds

The following compounds of the present invention were prepared using the general schemes disclosed above. Additional compounds of the invention can be prepared using the above general schemes, and the following specific syntheses, by a judicious selection of starting materials.

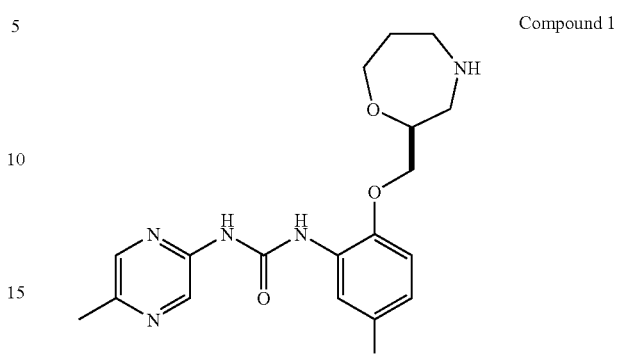

Compound 1

1-[5-Chloro-2-S-([1,4]oxazepan-2-ylmethoxy)-phenyl]-3-(5-methyl-pyrazin-2-yl)-urea Step 1: 2-Amino-5-methylpyrazine. Aminomalononitrile p-toluenesulfonate salt (20.0 g, 79 mmol) and pyruvaldehyde 1-oxime (6.88 g, 79 mmol) were combined in a flask. iPrOH (140 mL) was added, and the resulting yellow slurry was allowed to stir at room temperature for 18 h, during which time a yellow precipitate accumulated. The mixture was filtered and the precipitate was washed with iPrOH (2×50 mL) and DI $H_2O$ (20 mL), then lyophilized to give 2-amino-3-cyano-5-methylpyrazine N-oxide (10.7 g).

The pyrazine N-oxide was suspended in MeOH (22 mL) and AcOH (5 mL). To this, 5% Pt/C (1.6 g) and Darco KB-B (8 g) were carefully added. The mixture was allowed to absorb $H_2$ at 60 psi for 18 h. The reaction was quenched with 25% NaOH (34 mL) and purged with $N_2$ for 30 min. The mixture was filtered through a bed of wet celite and washed with MeOH (4×100 mL). The filtrate was concentrated in vacuo to a quarter volume. The filtrate was diluted with EtOAc (150 mL) and washed with 5% NaOH (30 mL) and back extracted with EtOAc (2×70 mL). The organic layers were combined and washed with sat'd NaCl (20 mL), filtered, and concentrated in vacuo to give an orange sticky solid (5.16 g).

Step 2: (5-Methylpyrazin-2-yl)carbamic acid phenyl ester. 2-Amino-5-methylpyrazine (5.16 g, 47 mmol) was dissolved in $CH_2Cl_2$ (52 mL), stirred and cooled to 0° C. under $N_2$. To this, pyridine (4.8 mL, 59 mmol) was added followed by phenyl chloroformate (6.2 mL, 59 mmol), dropwise, over 15 min, causing a precipitate to form. The mixture was stirred at 0° C. for 1 h. Then the reaction was quenched with 0.25 M HCl (40 mL) and anhydrous ether (50 mL), and stirred at 0° C., for 30 min. The precipitate was isolated by filtration, washed with DI $H_2O$ (20 mL) and ether (2×25 mL), and dried under vacuum to give the product (7.4 g) as a white fluffy powder.

Step 3: (S)-2-Hydroxymethyl-[1,4]oxazepane-4-carboxylic acid tert-butyl ester. To a 250 mL round bottom flask were added (S)-(+)-benzyl glycidyl ether, (1.31 g, 7.9 mmol), 3-benzylamino-propan-1-ol (1.3 g, 7.9 mmol) and 10 mL EtOH. The mixture was heated to 40° C. for 15 h. The reaction was cooled and concentrated in vacuo and the resulting oily product was used without further purification. The diol was placed in a 250 mL round bottom flask and dissolved in 75 mL dry pyridine. The solution was cooled to 0° C. and toluene sulfonyl chloride (5.27 g, 27.7 mmol) was added in one portion. The mixture was stirred for 6 h, carefully maintaining the reaction temperature at 0° C. The cold reaction was quenched with 50 mL sat'd aqueous NaHCO₃ solution. An additional 20 mL of water was added and the mixture was extracted three times with 100 mL portions of EtOAc. The combined organics were dried over Na₂SO₄ and concentrated in vacuo. The alcohol then was purified by column chromatography using a 25-50% gradient of EtOAc and hexanes as the eluent. This yielded 1.39 g of tosyl alcohol as a yellow oil.

The alcohol was dissolved in 50 mL DMF and cooled to 0° C. To the cold, stirred mixture was carefully added 95% wt. NaH (0.29 g, 11.5 mmol). The reaction was stirred at 0° C. for 15 min, then allowed to slowly warm to room temperature and stirred 6 h. The reaction was carefully quenched with 50 mL of water and extracted three times with 50 mL portions of EtOAc. The combined organics were dried over Na₂SO₄ and concentrated under vacuum. The crude product was taken up in EtOH and placed in a Parr hydrogenation apparatus. Also added to the solution were 10% wt. Pd/C (0.426 g, 0.30 mmol) and 2M HCl (2.1 mL). The hydrogenation was run at 50 psi for 2 days at which point the reaction was deemed to be done by LCMS analysis. The solution was neutralized with sat'd aqueous NaHCO₃ solution and extracted using a 3:1 mixture of CHCl₃:iPrOH. The combined organics were concentrated under vacuum and the crude product was taken on to the next step.

The crude amino alcohol was dissolved in 100 mL dry CH₂Cl₂. To this solution were added TEA (1.59 mL, 11.5 mmol) and di-tert-butyl dicarbonate (5.74 g, 5.74 mmol). The solution was stirred at room temperature for 18 h, then quenched with sat'd aqueous NaHCO₃ solution and extracted three times using 50 mL portions of CH₂Cl₂. The combined organics were dried over Na₂SO₄ and concentrated in vacuo. The product was purified by column chromatography using a 25-50% gradient of EtOAc/hexanes. This yielded 0.240 g of the oxazapane alcohol as a yellow oil.

Step 4: (S)-2-(4-Chloro-2-nitro-phenoxymethyl)-[1,4]oxazepane-4-carboxylic acid tert-butyl ester. To a 50 mL round bottom were added oxazapane alcohol (0.240 g, 1.03 mmol), TEA (0.21 mL, 1.545 mmol), and 10 mL dry CH₂Cl₂. The solution was cooled to 0° C. and methane sulfonyl chloride (0.10 mL) was added dropwise. The mixture was stirred for 1.5 h at 0° C. and then quenched, cold, with water. The layers were separated and the aqueous layer was extracted once with 20 mL CH₂Cl₂. The combined organics were dried over Na₂SO₄ and concentrated under vacuum. The crude mesylate then was dissolved in 5 mL dry DMF. To this solution was added Cs₂CO₃ (0.671 g, 2.06 mmol) and 4-chloro-2-nitrophenol (0.215 g, 1.24 mmol). This bright yellow solution then was heated to 100° C. overnight. The reaction was cooled to room temperature, quenched with 50 mL of water, and extracted three times with 50 mL portions of EtOAc. The product was purified by flash chromatography using a 10-35% gradient of EtOAc/hexanes. This sequence of steps yielded 0.120 g of the nitrophenyl oxazapane as a bright yellow oil.

Step 5: 1-[5-Chloro-2-([1,4]oxazepan-2-(S)-ylmethoxy)-phenyl]-3-(5-methyl-pyrazin-2-yl)-urea. In a 25 mL round bottom were placed nitrophenyl oxazapane (0.120 g, 0.31 mmol) and Pt₂O (0.007 g, 0.03 mmol) in 5 mL MeOH. A helium balloon was attached, the flask was evacuated using an aspirator, and backfilled with H₂ three times, then allowed to stir under H₂ for 2 h. The reaction was filtered through celite, washing the celite pad twice with 20 mL portions of MeOH. The solution was concentrated in vacuo. The crude aniline was dissolved in 5 mL of dry DMF. To this solution were added TEA (0.005 mL, 0.34 mmol) and (5-methylpyrazin-2-yl)carbamic acid phenyl ester (0.07 g, 0.31 mmol). This mixture was stirred 18 h at room temperature. The solvent was removed under vacuum and the residue was redissolved in 10 mL EtOAc and washed with sat'd aqueous NaHCO₃ solution. The organics were dried over Na₂SO₄ and concentrated at reduced pressure. The gray/brown residue was covered with 3 mL CH₂Cl₂ and to this was added 1 mL concentrated trifluoroacetic acid. Upon addition of acid all solids dissolved. The reaction was stirred at room temperature for 4 h at which time sat'd aqueous NaHCO₃ solution is added until solution reaches pH 8. The mixture was extracted three times with 10 mL portions of a 3:1 mixture of CHCl₃:iPrOH. The combined organics were then dried over Na₂SO₄ and concentrated under vacuum. The off white solids then were triturated in EtOAc and filtered through a medium fritted filter, washing with 50 mL of EtOAc. The white solid was thoroughly dried under vacuum. This sequence yielded 0.020 g of the desired urea as a fine white powder. ¹H-NMR (300 MHz, d₆-DMSO) δ 10.83 (br s, 1H), 8.39 (dd, 1H), 8.18 (s, 1H) 8.04 (br s, 1H), 6.99 (dd, 1H), 6.82 (d, 1H), 4.25-3.98 (m, 2H), 3.90-3.76 (m, 1H), 3.38 (d, 1H), 3.13-3.06 (m, 2H), 3.00 (dd, 1H), 2.54 (s, 3H), 2.06-1.89 (m, 3H). LCMS (ES, positive) m/e 392.3 (M+1).

Compound 2

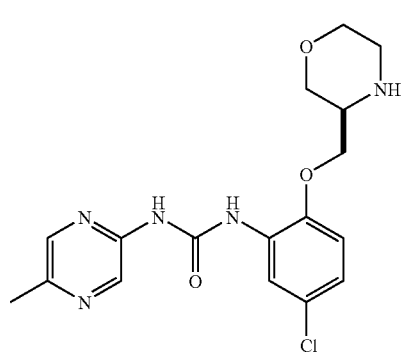

1-[5-Chloro-2-(R-morpholin-3-ylmethoxy)-phenyl]-3-(5-methyl-pyrazin-2-yl)-urea

Step 1: 3-Hydroxymethyl-5-morpholine-4-carboxylic acid tert-butyl ester. To a cooled (0° C. bath) solution of morpholine-3-R-4-dicarboxylic acid 4-tert-butyl ester (1.00 g, 4.32 mmol) in dry THF (40 mL) was added borane (4.76 mL of 1M solution in THF, 4.76 mmol) dropwise over 15 min under a nitrogen atmosphere. After stirring for 1 h, the bath was removed and stirring continued for an additional 3 h at ambient temperature. Acetic acid (14.3 mL of 1M aqueous solution, 14.3 mmol) then was added. After stirring for 1 h, the solution was neutralized by the addition of excess aqueous saturated sodium bicarbonate. Dichloromethane (20 mL) was added and the solution was stirred for 15 min, then the layers were separated. The aqueous layer was extracted with CH₂Cl₂ (3×20 mL), and the combined organic layers were dried (MgSO₄), and filtered. The filtered solution was concentrated to a white solid (0.46 g).

Step 2: 3-(4-Chloro-2-nitro-phenoxymethyl)-R-morpholine-4-carboxylic acid tert-butyl ester. To a cooled (−78° C. bath) stirred solution of 3-hydroxymethyl-S-morpholine-4-carboxylic acid tert-butyl ester (0.13 g, 0.60 mmol) and 5-chloro-2-fluoronitrobenzene (0.11 g, 0.66 mmol) in dry THF (40 mL) was added potassium bis(trimethylsilyl)amide (2.4 mL of 0.5M solution in THF, 1.2 mmol) dropwise over 15 min under a nitrogen atmosphere. After stirring an additional 15 min, aqueous saturated ammonium chloride (10 mL) was added and the bath removed to allow the solution to warm to ambient temperature. After stirring for 1 hour, water (15 mL) and $CH_2Cl_2$ (10 mL) were added and stirred for 5 min and the layers were separated. The aqueous layer was extracted with $CH_2Cl_2$ (2×10 mL) and the combined organic layers were dried ($MgSO_4$), and filtered. The filtered solution was concentrated to a yellow oil (0.26 g) that was purified by column chromatography eluting with hexanes/EtOAc (1:1) to afford a light yellow oil (0.195 g).

Step 3: 3-(2-Amino-4-chloro-phenoxymethyl)-R-morpholine-4-carboxylic acid tert-butyl ester. To a stirred solution of 3-(4-chloro-2-nitro-phenoxymethyl)-R-morpholine-4-carboxylic acid tert-butyl ester (0.17 g, 0.46 mmol) in MeOH (4 mL) was added $Pt_2O$ (0.020 g, 0.088 mmol). The flask was evacuated, then backfilled with $H_2$ for three iterations. After stirring for 4 h, the solution was filtered over a pad of Celite and the filtrate was concentrated to give the product as a yellow oil.

Step 4: 3-{4-Chloro-2-[3-(5-methyl-pyrazin-2-yl)-ureido]-phenoxymethyl}-R-morpholine-4-carboxylic acid tert-butyl ester. A solution of the yellow oil and (5-methyl-pyrazin-2-yl)-carbamic acid phenyl ester (0.13 g, 0.57 mmol) in dry DMF (2 mL) was prepared and TEA (0.074 mL, 0.53 mmol) was added. After stirring for 24 h, the reaction was concentrated under reduced pressure, then redissolved in water (10 mL) and EtOAc (10 mL). After stirring for 15 min, the layers were separated and the aqueous layer was extracted with EtOAc (2×10 mL) and combined organic layers were washed with brine (10 mL), then dried ($Na_2SO_4$) and filtered. The filtered solution was concentrated, then purified by column chromatography eluting with EtOAc/$CH_2Cl_2$ (1:1) to afford a yellow oil (0.8 g).

Step 5: 1-[5-Chloro-2-(R-morpholin-3-ylmethoxy)-phenyl]-3-(5-methyl-pyrazin-2-yl)-urea. To a stirred solution of 3-{4-chloro-2-[3-(5-methyl-pyrazin-2-yl)-ureido]-phenoxymethyl}-R-morpholine-4-carboxylic acid tert-butyl ester (0.8 g) in $CH_2Cl_2$ (6 mL) was added trifluoroacetic acid (3 mL). After stirring 5 h, the solution was treated with aqueous potassium carbonate solution (1M) until basic, then stirred for 30 min. The layers were separated and the aqueous layer was extracted with $CH_2Cl_2$ (3×10 mL). The combined organic layers were dried ($MgSO_4$), and filtered. The filtered solution was concentrated, then purified by column chromatography, eluting with MeOH/$CH_2Cl_2$ (1:9), to afford a pale yellow solid (0.0523 g). $^1$H-NMR (300 MHz, $d_6$-DMSO) δ 10.22 (s, 1H), 9.96 (br s, 1H), 8.74 (s, 1H), 8.28 (d, 1H), 8.18 (s, 1H), 7.04 (dd, 2H), 3.94 (m, 3H), 3.71 (br d, 1H), 3.43 (m, 1H), 3.23 (m, 2H), 3.34 (br m, 2H), 2.66 (br m, 1H), 2.43 (s, 3H). LRMS (es, positive) m/e 378.3 (M+1).

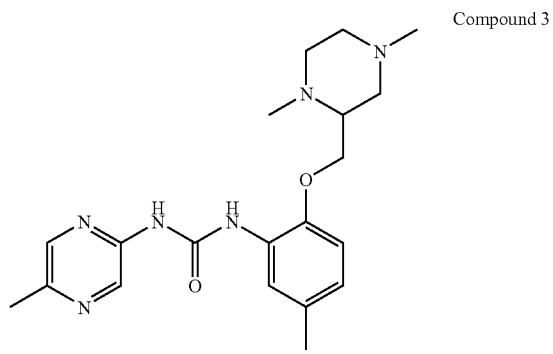

Compound 3

1-[2-(1,4-Dimethyl-piperazin-2-ylmethoxy)-5-methyl-phenyl]-3-(5-methyl-pyrazin-2-yl)-urea Step 1: 1,4-Dimethyl-2-(4-methyl-2-nitro-phenoxymethyl)-piperazine. 4-Methyl-2-nitro-phenol (0.95 g, 6.20 mmol), (1,4-dimethyl-piperazin-2-yl)-MeOH (0.98 g, 6.82 mmol), and triphenylphosphine (1.79 g, 6.82 mmol) were combined in THF, stirred for 5 min, then treated with DIAD (1.38 g, 6.82 mmol). The reaction was allowed to stir overnight. Concentration under vacuum afforded an orange oil which was dissolved in EtOAc and extracted with 2M aqueous HCl solution. The aqueous washes were combined, washed with EtOAc, and treated with solid NaOH until basic. The resulting aqueous mixture was extracted with EtOAc and the combined organic extracts were dried over $Na_2SO_4$, filtered and concentrated in vacuo to give a brown oil. Flash chromatography (1% MeOH in $CH_2Cl_2$) gave 1.0 g of the desired aryl ether.

Step 2: 2-(1,4-Dimethyl-piperazin-2-ylmethoxy)-5-methyl-phenylamine. 1,4-Dimethyl-2-(4-methyl-2-nitro-phenoxymethyl)-piperazine (1.02 g, 3.65 mmol) was dissolved in MeOH (75 mL) and treated with sat'd aqueous ammonium chloride solution until the mixture became turbid. Zinc (0.24 g, 3.65 mmol) was added. The resulting warm reaction mixture was allowed to stir for an additional 30 min at which time LCMS indicate that starting material had been consumed. The reaction was diluted with EtOAc and aqueous $Na_2CO_3$ and the layers were separated. The organic layer was washed with saturated NaCl solution and dried over solid anhydrous $Na_2SO_4$. The mixture was filtered and concentrated in vacuo to afford the desired aniline.

Step 3: 1-[2-(1,4-Dimethyl-piperazin-2-ylmethoxy)-5-methyl-phenyl]-3-(5-methyl-pyrazin-2-yl)-urea. 5-Methyl-pyrazine-2-carboxylic acid (691 mg, 5 mmol) was stirred in toluene (15 mL) and treated with TEA (765 mL, 5.5 mmol) followed by diphenylphosphoryl azide (1.0 mL, 5.0 mmol). The resulting solution was stirred for 30 min, then used directly.

A solution of 5-methyl-pyrazine-2-carbonyl azide (1.0 mmol) in toluene was heated at 90° C. for 10 min. The reaction flask was removed from the heating bath and the brown solution was treated with 2-(1,4-dimethyl-piperazin-2-ylmethoxy)-5-methyl-phenylamine (0.25 g, 1.0 mmol). The flask was returned to the heating bath and heated at 40° C. for 4 h. The mixture was allowed to cool, then filtered to give the product as a tan powder. $^1$H-NMR (400 MHz, $CDCl_3$) δ 10.90 (s, 1, H), 8.4 (s, 1, H), 8.2 (m, 3, H), 6.8 (m, 2, H), 4.2 (dd, 1, H), 3.9 (t, 1, H), 3.1 (d, 1, H), 2.8 (br d, 1, H), 2.6 (m, 2, H), 2.5 (s, 3, H), 2.4 (m, 1, H), 2.4 (s, 3, H), 2.3 (s, 3, H), 2.25 (m, 1, H), 2.2 (s, 3, H), 2.1 (m, 1, H). LRMS (esi, positive) m/e 385.30 (M+1).

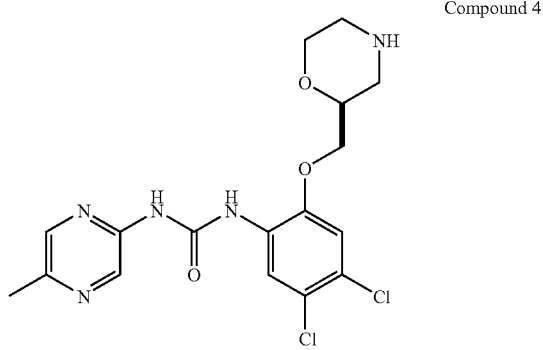

Compound 4

1-[4,5-Dichloro-2-(S-morpholin-2-ylmethoxy)-phenyl]-3-(5-methyl-pyrazin-2-yl)-urea Step 1: (S)-2-Hydroxymethyl-morpholine-4-carboxylic acid tert-butyl ester. In a 500 mL flask were combined (S)-benzyl glycidyl ether (15 g, 91.4 mmol), MeOH (10 mL), and 50% wt. NaOH (30 mL, 365 mmol). To this mixture was added 2-aminoethylsulfate (25.8 g, 183 mmol) in portions. This heterogeneous mixture was heated to 40° C. at which point the solution becomes homogenous. The temperature was maintained at 40° C. for 4 h. The reaction was cooled slightly and additional solid NaOH (14.6 g, 365 mmol) was added along with 50 mL toluene. The biphasic solution then was heated to 65° C. for 12 h. The reaction was cooled to room temperature, the layers were separated and the aqueous layer was extracted once with 75 mL of toluene. The combined organic layers were washed three times with 75 mL portions of 1M HCl. The pH of the combined aqueous layers was adjusted to pH 12 with aqueous NaOH solution and extracted four times with 70 mL portions of EtOAc. The combined organics were dried over $Na_2SO_4$ and concentrated in vacuo to yield 10.084 g of the desired morpholine as an opaque oil.

The crude morpholine product was dissolved in $CH_2Cl_2$ (100 mL) and TEA (12.1 mL, 87.5 mmol) and di-tert-butyl dicarbonate (15.9 g, 73 mmol) was added accompanied by the generation of $CO_2$ gas. The reaction was stirred at room temperature for 18 h, then quenched with 35 mL sat'd aqueous $NaHCO_3$ solution. An additional 50 mL water was added and the layers were separated. The organic layer was dried over anhydrous $Na_2SO_4$, concentrated in vacuo and purified by flash chromatography (20% EtOAc/hexane) to give the desired N-Boc-O-benzyl morpholine as a pale yellow oil (5.536 g).

The purified diprotected morpholine was dissolved in 50 L absolute EtOH and $Pd(OH)_2$ (1.26 g, 20% wt, 1.8 mmol) was added. A hydrogen balloon was attached and the flask was evacuated using an aspirator and backfilled with $H_2$ three times. The reaction was stirred under $H_2$ for 30 h. The mixture was filtered over celite, rinsing the celite pad thoroughly with EtOH. The filtered solution was concentrated down under vacuum to yield of the desired N-boc-morpholine alcohol as a pale white solid (3.918 g).

Step 2: 4,5-Dichloro-2-nitro-phenol. A 250 mL roundbottom flask charged with 3,4-dichlorophenol (3.053 g, 18.7 mmol) in 50 mL $CH_2Cl_2$ was cooled to 0° C. in an ice bath. To the stirred solution was added concentrated $H_2SO_4$ (1.56 mL, 28.1 mmol). The solution became turbid. To this mixture was added concentrated $HNO_3$ (1.2 mL, 18.7 mmol), dropwise and carefully to maintain a temperature below 5° C. The reaction was stirred for 30 min at 0° C., then cooled with an ice bath and quenched with 150 mL $H_2O$. The layers were separated and the aqueous layer was extracted once with 35 mL $CH_2Cl_2$. The combined organics were dried over anhydrous $Na_2SO_4$, concentrated under vacuum and purified using flash chromatography (10% EtOAc/hexanes as eluent) to yield the desired nitrophenol as a bright yellow solid (1.793 g).

Step 3: 1-[4,5-Dichloro-2-(S-morpholin-2-ylmethoxy)-phenyl]-3-(5-methyl-pyrazin-2-yl)-urea. Prepared according to the procedure for Compound 1, Steps 4 and 5, using 4,5-dichloro-2-nitro-phenol and (S)-2-benzyloxymethyl-morpholine-4-carboxylic acid tert-butyl ester. $^1$H-NMR (300 MHz, $d_6$-DMSO) δ 10.42 (s, 1H), 10.29 (s, 1H), 8.93 (s, 1H), 8.42 (s, 1H), 8.21 (s, 1H), 7.32 (s, 1H), 4.18-3.41 (m, 5H), 3.03-2.66 (m, 4H), 2.38 (s, 3H) LRMS (ES, positive) m/e 412.2 (M+1).

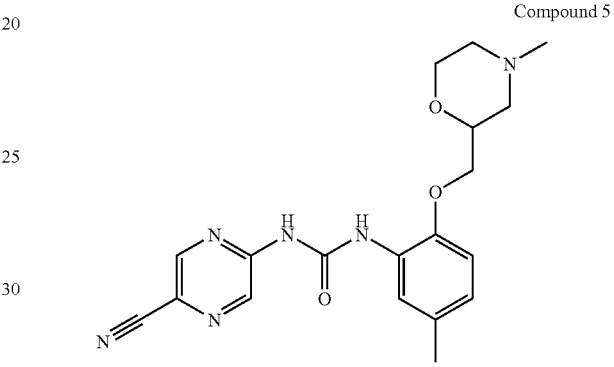

Compound 5

1-(5-Cyano-pyrazin-2-yl)-3-[5-methyl-2-(4-methyl-morpholin-2-ylmethoxy)-phenyl]-urea Step 1: 5-Bromo-pyrazin-2-ylamine. A solution of pyrazin-2-ylamine (6.66 g, 70 mmol) in $CH_2Cl_2$ (200 mL) was cooled to 0° C., treated with N-bromosuccinamide (12.5 g, 70 mmol) and allowed to warm to room temperature. The resulting reaction mixture was stirred overnight, then diluted with additional $CH_2Cl_2$ (200 mL) and washed with 10% aqueous $Na_2CO_3$ solution. The layers were separated, and the organic layer washed with sat'd aqueous NaCl solution, then dried over anhydrous $MgSO_4$ filtered, and concentrated under reduced pressure. The residue was taken up in EtOAc (50 mL) and the product was precipitated by the addition of hexane (300 mL). The precipitate was dried under vacuum to yield 5.57 g of a tan solid.

Step 2: 5-Amino-pyrazine-2-carbonitrile. 5-Bromo-pyrazin-2-ylamine was combined with copper (I) iodide (1.3 g, 6.9 mmol), potassium cyanide (0.44 g, 6.8 mmol), tetrakis (triphenylphosphine)palladium(0) (0.95 g, 0.83 mmol), and 18-crown-6 (0.058 g, 0.22 mmol) in DMF (15 mL). The resulting mixture was stirred for 40 min, then heated at reflux (155° C.) for 2 h. The reaction was cooled to room temperature, then allowed to stand overnight. The precipitate was separated by filtration and the filtrate was concentrated to dryness in vacuo. The orange-colored residue was taken up in EtOAc and hexanes and an initial precipitate was formed, then separated by filtration. Upon standing, additional precipitate formed in the mother liquor and was collected by filtration. The solids were combined to yield 0.10 g of a bright orange solid.

Step 3: 2-{2-[3-(5-Cyano-pyrazin-2-yl)-ureido]-4-methyl-phenoxymethyl}-morpholine-4-carboxylic acid tert-butyl ester. 2-(2-Amino-4-methyl-phenoxymethyl)-morpholine-4-carboxylic acid tert-butyl ester (0.087 g, 0.270 mmol) was prepared from 2-amino-4-methyl-phenol according to methods of Compound 3, Steps 1 and 2 using 2-hydroxymethyl-morpholine-4-carboxylic acid tert-butyl ester (prepared according to the procedure for Compound 2, Step 1 using the corresponding acid) and 4-methyl-2-nitro-phenol. It was combined with triphosgene (0.029 g, 0.10 mmol), toluene (2 mL) and Hunig's base (0.15 mL, 0.86 mmol), and stirred at room temperature for 25 min. The suspension then was transferred through a cannula to a cold solution (−78° C.) containing 5-amino-pyrazine-2-carbonitrile (0.032 g, 0.27 mmol), and lithium bis(trimethylsilyl)amide (0.27 mmol) in THF (1 mL), which had been stirring at −78° C. for 30 min. The reaction was allowed to warm, then was stirred for 16 h at room temperature. A precipitate formed and was collected by filtration to yield the desired product (0.043 g).

Step 4: 1-(5-Cyano-pyrazin-2-yl)-3-[5-methyl-2-(morpholin-2-ylmethoxy)-phenyl]-urea. A slurry of 2-{2-[3-(5-cyano-pyrazin-2-yl)-ureido]-4-methyl-phenoxymethyl}-morpholine-4-carboxylic acid tert-butyl ester (0.043 g, 0.0918 mmol) in THF (2 mL) was treated with HCl in dioxane (4M, 0.11 mL) and stirred for 20 h. Additional HCl in dioxane (4M, 0.25 mL) was added and the reaction was heated to 50° C. for 18 h. The reaction was cooled and concentrated. The resulting solid was suspended in ether, and the suspension filtered and air dried to afford the desired product as the HCl salt (0.042 g).

Step 5: 1-(5-Cyano-pyrazin-2-yl)-3-[5-methyl-2-(4-methyl-morpholin-2-ylmethoxy)-phenyl]-urea. A solution of 1-(5-cyano-pyrazin-2-yl)-3-[5-methyl-2-(morpholin-2-ylmethoxy)-phenyl]-urea hydrochloride salt (0.0104 g, 0.129 mmol) in MeOH (1 mL) was cooled to 0° C. and treated with an aqueous solution of formaldehyde (0.12 mmol) followed by sodium triacetoxy borohydride (0.06 g, 0.292 mmol). The reaction was stirred for 12 h, then concentrated in vacuo. The residue was chromatographed on silica (2% MeOH in $CH_2Cl_2$) to give the product as a white solid (0.014 g). $^1$H-NMR (400 MHz, $d_6$-DMSO) δ 10.90 (s, 1, H), 10 (br s, 1, H), 8.9 (s, 1, H), 8.8 (s, 1, H), 8 (s, 1, H), 6.9 (m, 1, H), 6.8 μm, 1, H), 3.9 (m, 4, H), 3.6 (t, 1, H), 2.9 (d, 1, H), 2.7 (d, 1, H), 2.2 (s, 3, H), 2.1 (s, 3, H), 2 (t, 1, H), 1.8 (t, 1, H). LRMS (esi, positive) m/e 383.40 (M+1).

Compound 6

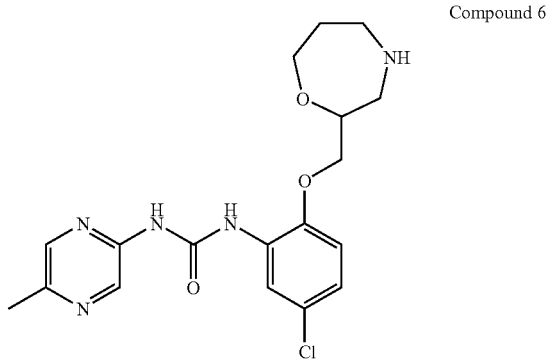

1-[5-Chloro-2-([1,4]oxazepan-2-ylmethoxy)-phenyl]-3-(5-methyl-pyrazin-2-yl)-urea Step 1: 3-Benzyl-2-chloromethyl-[1,3]oxazepane. A solution of 3-benzylamino-propan-1-ol (14 g, 88.0 mmol) and epichlorohydrin (81.4 g, 880 mmol) was heated to 40° C. After stirring for 3 h the reaction was cooled and excess epichlorohydrin was removed by evaporation in vacuo. Sulfuric acid (10 mL) was added slowly, then the reaction flask was placed in a preheated oil bath at 150° C. Stirring proceeded for 1 h, then the reaction was allowed to cool to room temperature and quenched with the addition of ice. The mixture was adjusted to a basic pH with 10% aqueous $Na_2CO_3$ solution and extracted with EtOAc (3×300 mL). The combined organic layers were dried over anhydrous $MgSO_4$, filtered, and dried under reduced pressure. The resulting residue was purified by flash chromatography (70:28:2 hexanes/$CH_2Cl_2$/2M $NH_4OH$ aq) to afford 5 g of a light yellow oil.

Step 2: 2-(4-Chloro-2-nitro-phenoxymethyl)-[1,3]oxazepane-3-carboxylic acid tert-butyl ester. To a stirred solution of 4-bromo-2-nitro-phenol (1.39 g, 8.0 mmol) in DMSO (30 mL) was added potassium carbonate (2.76 g, 20.0 mmol) followed by 3-benzyl-2-chloromethyl-[1,3]oxazepane. The reaction was stirred at 60° C. for 12 h then allowed to cool to room temperature and diluted with EtOAc (200 mL) and 10% aqueous $Na_2CO_3$ solution (200 mL). The layers were separated and the organic layer was washed with brine, dried over anhydrous $MgSO_4$ and concentrated in vacuo. The crude product was purified by flash chromatography (70:30 hexanes/EtOAc) to give 480 mg of a light orange oil.

The oil was taken up in $CH_2Cl_2$ (5 mL) and cooled in an ice bath. The alpha chloro ethyl chloroformate (0.18 mL, 1.65 mmol) was added. The reaction was stirred for 2 h, then 2N aqueous HCl solution was added. Stirring was continued for 10 min, then the mixture was concentrated to dryness. The resulting residue was taken up in MeOH and refluxed for 2 h. The reaction was concentrated under reduced pressure and the residue was taken up in 2N aqueous HCl solution (75 mL) and washed with EtOAc (2×50 mL). The pH of the aqueous layer was adjusted to a pH of 11 by the addition of solid NaOH. The resulting basic solution was extracted with EtOAc (2×50 mL) and the combined organic layers were washed with brine and dried over $MgSO_4$. Filtration and concentration in vacuo afforded 240 mg of product as a light yellow oil.

The oil was dissolved in $CH_2Cl_2$ (3 mL), then treated with TEA (0.116 mL, 0.831 mmol) and di-tert-butyl dicarbonate (0.181 g, 0.831 mmol). The reaction was allowed to stir at room temperature for 1 h then diluted with additional $CH_2Cl_2$ (100 mL) and washed with 10% aqueous $Na_2CO_3$ solution (100 mL). The organic layer was dried over $MgSO_4$, filtered and concentrated under reduced pressure. Purification was achieved using flash chromatography (7:3 hexane/EtOAc) to give 252 mg of the product as of a white foam.

Step 3: 2-(2-Amino-4-chloro-phenoxymethyl)-[1,3]oxazepane-3-carboxylic acid tert-butyl ester. Prepared from 2-(4-chloro-2-nitro-phenoxymethyl)-[1,3]oxazepane-3-carboxylic acid tert-butyl ester (0.252 g, 0.65 mmol) according to the procedure for Compound 3, Step 2 to give 150 mg of the product as a clear oil.

Step 4: 1-[5-Chloro-2-([1,4]oxazepan-2-ylmethoxy)-phenyl]-3-(5-methyl-pyrazin-2-yl)-urea. Prepared from 2-(2-amino-4-chloro-phenoxymethyl)-[1,3]oxazepane-3-carboxylic acid tert-butyl ester using according to the procedure for Compound 2, Step 4 and Compound 5, Step 4, to give 0.175 g of product. $^1$H-NMR (400 MHz, $CDCl_3$), δ 8.65 (br s, 1, H), 8.3 (s, 1, H), 8.25 (s, 1, H), 6.98 (dd, 1, H), 6.8 (d, 1, H), 4.08 (m, 3, H), 3.8 (m, 1, H), 3.35 (s, 1, H), 3.25 (d, 1, H), 3 (m, 3, H), 2.5 (s, 3, H), 1.98 (m, 2, H). LRMS (esi, positive) m/e 391.90 (M+1).

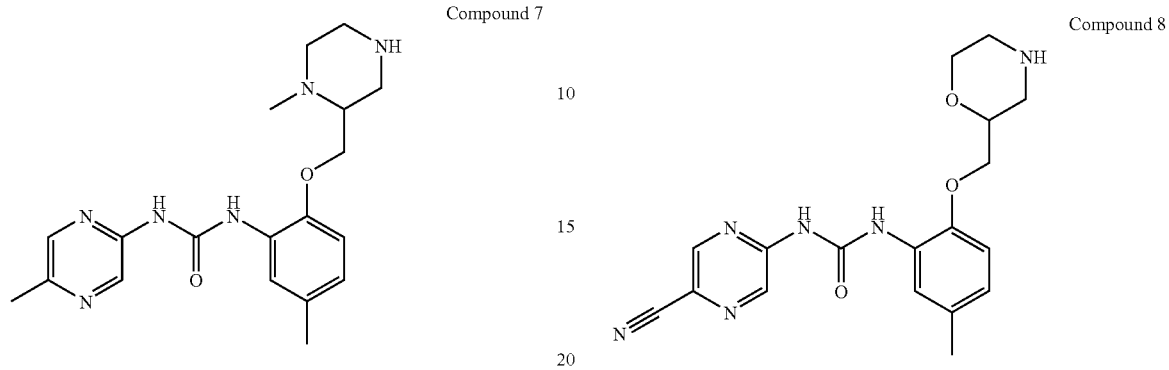

Compound 7

1-[5-Methyl-2-(1-methyl-piperazin-2-ylmethoxy)-phenyl]-3-(5-methyl-pyrazin-2-yl)-urea Step 1: 3-Hydroxymethyl-4-methyl-piperazine-1-carboxylic acid tert-butyl ester. Piperazine-2-carboxylic acid (20 g, 154 mmol) in a slurry with 200 mL of 1:1 $H_2O$/dioxane was cooled in an ice bath and treated with solid NaOH (11 g) followed by a solution of di-tert-butyl dicarbonate (21.6 g, 99 mmole) in dioxane added dropwise from an addition funnel. The reaction pH was adjusted to pH>10 as needed during the course of the reaction. The resulting mixture was allowed to stir for 3 h, then diluted with water until homogeneous and acidified with concentrated aqueous HCl until the pH was between 2 and 3. The solution was washed with ether then the pH was adjusted with NaOH until pH was 6.5 to 7. The solution was allowed to stand several days and the resulting precipitate was collected by filtration to give piperazine-1,3-dicarboxylic acid 1-tert-butyl ester as a white solid (9.7 g).

A slurry of piperazine-1,3-dicarboxylic acid 1-tert-butyl ester (4.62 g, 20.0 mmol) in $CH_3OH$ (100 mL) was treated with aqueous formaldehyde (40 mmol) and formic acid (70 mmol), then heated at 65° C. for several hours. Upon completion by HPLC, the reaction was allowed to cool and was concentrated in vacuo.

The residue was taken up in THF and cooled in an ice bath, then treated with a solution of lithium aluminum hydride in THF (19.0 mmol). After 1 h, the reaction was allowed to warm to room temperature and stirred for an additional 30 min. The reaction then was cooled in an ice bath and quenched with $H_2O$ (0.75 mL) and 15% aqueous NaOH solution (0.75 mL), and $H_2O$ again (3×0.75 mL). The salts were removed by filtration and the filtrate concentrated under vacuum to give the crude product. Chromatography over silica gel (2.5% MeOH in $CH_2Cl_2$) gave the product as a yellow oil (0.70 g).

Step 2: 1-[5-Methyl-2-(1-methyl-piperazin-2-ylmethoxy)-phenyl]-3-(5-methyl-pyrazin-2-yl)-urea. Prepared according to the procedure for Compound 3 using 3-hydroxymethyl-4-methyl-piperazine-1-carboxylic acid tert-butyl ester, and the procedure for Compound 5, Step 4. $^1$H-NMR (400 MHz, $d_6$-DMSO) δ 10.24 (br s, 1, H), 10.1 (s, 1, H), 9.7 (br s, 1, H), 9.42 (s, 1, H), 9.12 (s, 1, H), 8.2 (s, 1, H), 8.08 (s, 1, H), 6.91 (d, 1, H), 6.82 (d, 1, H), 4.6 (d, 1, H), 4.4 (m, 1, H), 4.1 (m, 1, H), 3.6 (m, 6, H), 3 (s, 3, H), 2.4 (s, 3, H), 2.2 (s, 3, H). LRMS (esi, positive) m/e 371.40 (M+1).

Compound 8

1-(5-Cyano-pyrazin-2-yl)-3-[5-methyl-2-(morpholin-2-ylmethoxy)-phenyl]-urea

Prepared according to the procedures for Compound 5, Steps 1 through 4, using 4-methyl-2-nitro-phenol. $^1$H-NMR (400 MHz, $CD_3OD$), δ 8.80 (s, 1, H), 8.7 (s, 1, H), 7.9 (s, 1, H), 6.8 (m, 2, H), 4.2 (m, 4, H), 3.8 (m, 1, H), 3.6 (m, 1, H), 3.5 (m, 1, H), 3.2 (m, 2, H), 2.3 (s, 3, H). LRMS (esi, positive) m/e 369.30 (M+1).

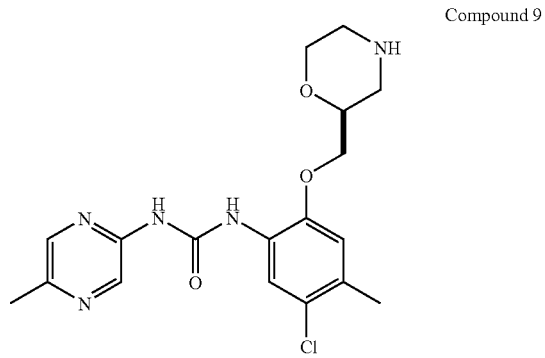

Compound 9

1-[5-Chloro-4-methyl-2-(S-morpholin-2-yl-methoxy)-phenyl]-3-(5-methyl-pyrazin-2-yl)-urea Prepared according to the procedure for Compound 1, Steps 4 and 5 using 2-hydroxymethyl-S-morpholine-4-carboxylic acid tert-butyl ester, prepared using the procedure for Compound 4, Step 1 and 4-chloro-5-methyl-2-nitro-phenol, prepared according to the procedure for Compound 4, Step 2. $^1$H-NMR (300 MHz, $d_6$-DMSO) δ 10.32 (s, 1H), 10.21 (s, 1H), 8.75 (s, 1H), 8.29-8.10 (m, 2H), 7.06 (d, 1H), 7.18 (d, 1H), 4.12-3.42 (m, 5H), 3.29-2.63 (m, 4H), 2.48 (s, 3H), 2.25 (s, 3H). LRMS (ES, positive) m/e 392.2 (M+1).

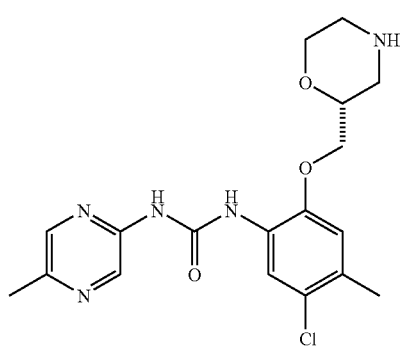

Compound 10

1-[5-Chloro-4-methyl-2-(R-morpholin-2-yl-methoxy)-phenyl]-3-(5-methyl-pyrazin-2-yl)-urea Prepared according to the procedure for Compound 1, Steps 4 and 5 using 2-hydroxymethyl-R-morpholine-4-carboxylic, prepared from (R)-benzyl glycidyl ether acid tert-butyl ester, using the procedure for Compound 4, Step 1, and 4-chloro-5-methyl-2-nitro-phenol, prepared according to the procedure for Compound 4, Step 2. $^1$H-NMR (300 MHz, $d_6$-DMSO) δ 10.32 (s, 1H), 10.21 (s, 1H), 8.75 (s, 1H), 8.29-8.10 (m, 2H), 7.06 (d, 1H), 7.18 (d, 1H), 4.12-3.42 (m, 5H), 3.29-2.63 (m, 4H), 2.48 (s, 3H), 2.25 (s, 3H). LRMS (ES, positive) m/e 392.3 (M+1).

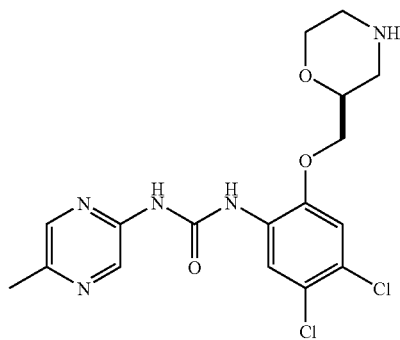

Compound 11

1-[4,5-Dichloro-2-(R-morpholin-2-ylmethoxy)-phenyl]-3-(5-methyl-pyrazin-2-yl)-urea Prepared according to the procedure for Compound 1, Steps 4 and 5 using 2-hydroxymethyl-S-morpholine-4-carboxylic acid tert-butyl ester and 4,5-dichloro-2-nitro-phenol, prepared according to the procedure for Compound 4, Step 2. $^1$H-NMR (300 MHz, $d_6$-DMSO) δ 10.42 (s, 1H), 10.29 (s, 1H), 8.93 (s, 1H), 8.42 (s, 1H), 8.21 (s, 1H), 7.32 (s, 1H), 4.18-3.41 (m, 5H), 3.03-2.66 (m, 4H), 2.38 (s, 3H). LRMS (ES, positive) m/e 412.2 (M+1).

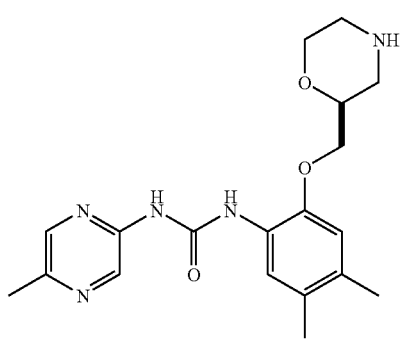

Compound 12

1-[4,5-Dimethyl-2-(morpholin-2-ylmethoxy)-phenyl]-3-(5-methyl-pyrazin-2-yl)-urea Prepared according to the procedures for Compound 1, Steps 4 and 5 using 2-hydroxymethyl-S-morpholine-4-carboxylic acid tert-butyl ester and 4,5-dimethyl-2-nitro-phenol, prepared according to the procedure for Compound 4, Step 2. $^1$H-NMR (300 MHz, $d_6$-DMSO) δ 10.02 (s, 1H), 9.89 (br s, 1H), 8.85 (br s, 1H), 8.27 (s, 1H), 8.91 (s, 1H), 6.84 (s, 1H), 4.18-3.97 (m, 3H), 3.69 (t, 1H), 3.43-3.26 (m, 2H), 2.97 (t, 2H), 2.33 (s, 3H), 2.18 (s, 2H), 2.12 (s, 3H). LRMS (ES, positive) m/e 372.3 (M+1).

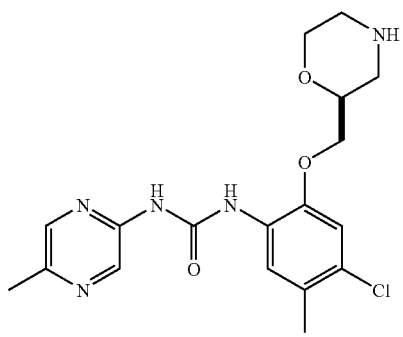

Compound 13

1-[4-Chloro-5-methyl-2-(S-morpholin-2-yl-methoxy)-phenyl]-3-(5-methyl-pyrazin-2-yl)-urea Prepared according to the procedures for Compound 1, Steps 4 and 5 using 2-hydroxymethyl-S-morpholine-4-carboxylic acid tert-butyl ester and 5-chloro-4-methyl-2-nitro-phenol, prepared according to the procedure for Compound 4, Step 2. $^1$H-NMR (300 MHz, $d_6$-DMSO) δ 10.26 (s, 1H), 8.82 (s, 1H), 8.19 (s, 1H), 8.17 (s, 1H), 7.10 (s, 1H), 4.21-3.96 (m, 2H), 3.90-3.86 (m, 2H), 3.54 (dt, 1H), 2.98 (d, 1H), 2.84 (t, 2H), 2.36 (s, 3H), 2.21 (s, 3H). LRMS (ES, positive) m/e 392.1 (M+1).

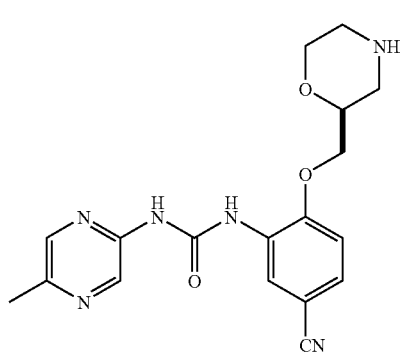

Compound 14

1-[5-Cyano-2-(S-morpholin-2-ylmethoxy)-phenyl]-3-(5-methyl-pyrazin-2-yl)-urea

Prepared according to the procedure for Compound 1, Steps 4 and 5 using 2-hydroxymethyl-S-morpholine-4-carboxylic acid tert-butyl ester and 4-hydroxy-3-nitro-benzonitrile, prepared according to the procedure for Compound 4, Step 2. $^1$H-NMR (300 MHz, $d_6$-DMSO) δ 10.43 (br s, 1H), 10.30 (s, 1H), 8.62 (br s, 1H), 8.53 (s, 1H), 8.21 (s, 1H), 7.48 (d, 1H), 7.33 (d, 1H), 4.20-4.11 (m, 2H), 3.94-3.73 (m, 2H), 3.51 (dt, 1H), 3.00 (d, 1H), 2.77-2.61 (m, 2H). LRMS (ES, positive) m/e 369.2 (M+1).

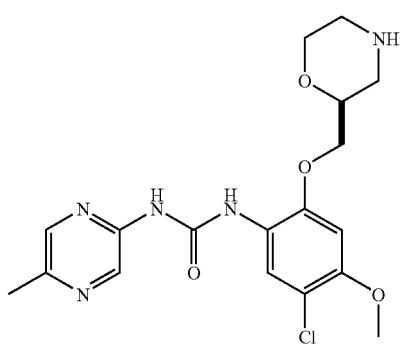

Compound 16

1-[5-Chloro-4-methoxy-2-(S-morpholin-2-ylmethoxy)-phenyl]-3-(5-methyl-pyrazin-2-yl)-urea Prepared according to the procedures for Compound 1, Steps 4 and 5 using 2-hydroxymethyl-S-morpholine-4-carboxylic acid tert-butyl ester and 4-chloro-5-methoxy-2-nitrophenol, prepared according to the procedure for Compound 4, Step 2. $^1$H-NMR (300 MHz, $d_6$-DMSO) δ 10.11 (s, 1H), 10.05 (br s, 1H), 8.64 (s, 1H), 8.19 (s, 2H), 6.91 (s, 1H), 4.29 (s, 2H), 4.16 (m, 1H), 4.09 (d, 1H), 3.87 (s, 3H), 3.75 (t, 1H), 3.44-3.17 (m, 2H), 3.01 (t, 2H), 2.39 (s, 3H). LRMS (ES, positive) m/e 408.0 (M+1).

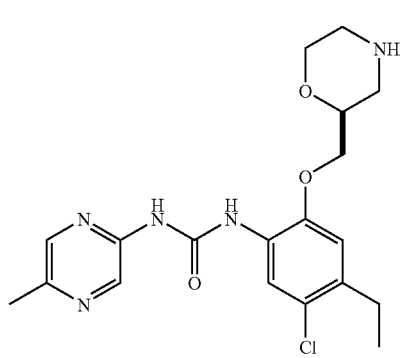

Compound 15

1-[5-Chloro-4-ethyl-2-(S-morpholin-2-ylmethoxy)-phenyl]-3-(5-methyl-pyrazin-2-yl)-urea Prepared according to the procedure for Compound 1, Steps 4 and 5 using 2-hydroxymethyl-S-morpholine-4-carboxylic acid tert-butyl ester and 4-chloro-5-ethyl-2-nitrophenol, prepared according to the procedure for Compound 4, Step 2. $^1$H-NMR (300 MHz, $d_6$-DMSO) δ 10.33 (s, 1H), 10.19 (s, 1H), 8.66 (s, 1H), 8.33-8.01 (m, 3H), 7.05 (d, 1H), 4.29-3.39 (m, 5H), 3.29-2.91 (m, 2H), 2.89-2.70 (m, 2H), 2.58 (q, 2H), 2.49 (s, 3H), 1.17 (t, 3H). LRMS (ES, positive) m/e 406.1 (M+1).

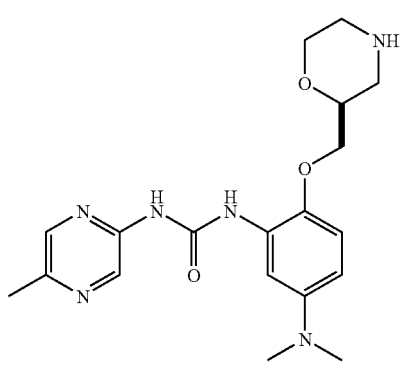

Compound 17

1-[5-Dimethylamino-2-(S-morpholin-2-ylmethoxy)-phenyl]-3-(5-methyl-pyrazin-2-yl)-urea Prepared according to the procedure for Compound 1, Steps 4 and 5 using 2-hydroxymethyl-S-morpholine-4-carboxylic acid tert-butyl ester and 4-dimethylamino-2-nitrophenol, prepared according to the procedure for Compound 4, Step 2. $^1$H-NMR (300 MHz, $d_6$-DMSO) δ 10.11 (s, 1H), 10.05 (br s, 1H), 8.69 (s, 1H), 8.19 (s, 1H), 7.75 (s, 1H), 6.90 (d, 1H), 6.34 (dd, 1H), 4.05-3.81 (m, 4H), 3.56 (t, 1H), 3.14 (d, 1H), 2.93 (d, 1H), 2.80 (s, 6H), 2.76-2.63 (m, 2H), 2.41 (s, 3H). LRMS (ES, positive) m/e 387.4 (M+1).

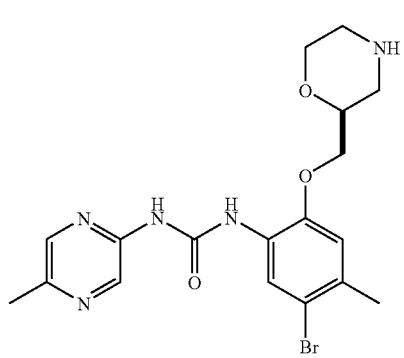

Compound 18

1-[5-Bromo-4-methyl-2-S-(morpholin-2-yl-methoxy)-phenyl]-3-(5-methyl-pyrazin-2-yl)-urea Prepared according to the procedure for Compound 4, using 4-bromo-5-methyl-2-nitro-phenol, prepared using the procedure for Compound 4, Step 2. $^1$H-NMR (300 MHz, $d_6$-DMSO) δ 10.31 (br s, 1H), 10.19 (s, 1H), 8.63 (s, 1H), 8.41 (s, 1H), 8.20 (s, 1H), 7.07 (s, 1H), 4.13-3.94 (m, 3H), 3.87-3.74 (m, 2H), δ 3.52 (td, 1H), 3.00 (d, 1H), 2.69 (t, 2H), 2.42 (s, 1H), 2.25 (s, 1H). LRMS (ES, positive) m/e 438.2.0 (M+1).

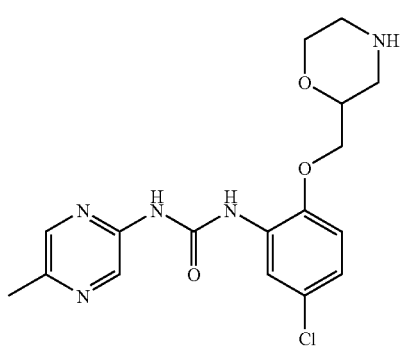

Compound 20

1-[5-Chloro-2-(morpholin-2-ylmethoxy)-phenyl]-3-(5-methyl-pyrazin-2-yl)-urea

Prepared according to the procedure for Compound 3 using 4-chloro-2-nitro-phenol and 2-hydroxymethyl-morpholine-4-carboxylic acid tert-butyl ester which was prepared from the corresponding acid according to the procedure for Compound 2, Step 1. $^1$H-NMR (400 MHz, $CD_3OD$), δ 8.70 (s, 1, H), 8.5 (s, 1, H), 8.4 (s, 1, H), 7.05 (m, 1, H), 4.2 (m, 4, H), 3.8 (t, 1, H), 3.5 (d, 1, H), 3.2 (m, 2, H), 2.6 (s, 3, H). LRMS (esi, positive) m/e 378.50 (M+1).

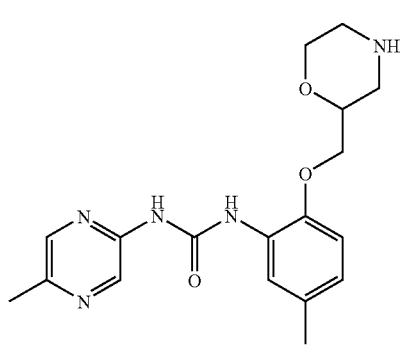

Compound 19

1-[5-Methyl-2-(morpholin-2-ylmethoxy)-phenyl]-3-(5-methyl-pyrazin-2-yl)-urea

Prepared according to the procedure for Compound 3 using 2-hydroxymethyl-morpholine-4-carboxylic acid tert-butyl ester which was prepared from the corresponding acid according to the procedure for Compound 2, Step 1. $^1$H-NMR (400 MHz, $CD_3OD$), δ 8.90 (s, 1, H), 8.6 (s, 1, H), 7.9 (s, 1, H), 6.9 (m, 2, H), 4.2 (m, 4, H), 3.8 (t, 1, H), 3.7 (s, 2, H), 3.5 (d, 1, H), 3.2 (m, 1, H), 2.6 (s, 3, H), 2.3 (s, 3, H). LRMS (esi, positive) m/e 358.20 (M+1).

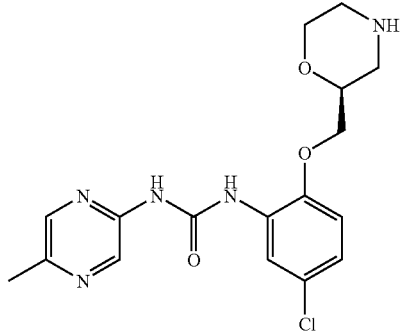

Compound 21

1-[5-Chloro-2-(S-morpholin-2-ylmethoxy)-phenyl]-3-(5-methyl-pyrazin-2-yl)-urea

Prepared according to the procedure for Compound 4 using 4-chloro-2-nitro-phenol. $^1$H-NMR (400 MHz, $d_6$-DMSO) δ 10.35 (s, 1, H), 9.4 (br s, 1, H), 8.55 (br s, 1, H), 8.25 (m, 2, H), 7.22 (m, 2, H), 4.2 (m, 3, H), 4 (d, 1, H), 3.8 (t, 1, H), 3.4 (d, 1, H), 3.2 (d, 1, H), 2.8 (m, 1, H), 2.45 (s, 3, H). LRMS (esi, positive) m/e 378.30 (M+1).

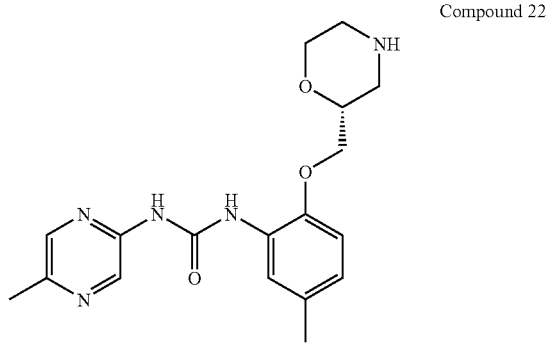

Compound 22

1-[5-Methyl-2-(S-morpholin-2-ylmethoxy)-phenyl]-
3-(5-methyl-pyrazin-2-yl)-urea

Prepared according to the procedure for Compound 4 using (R)-benzyl glycidyl ether and 4-methyl-2-nitro-phenol. $^1$H-NMR (400 MHz, $d_6$-DMSO) δ 10.20 (s, 1, H), 10.1 (br s, 1, H), 9.89 (br s, 1, H), 9.5 (br s, 1, H), 8.7 (s, 1, H), 8.3 (s, 1, H), 7.98 (s, 1, H), 6.9 (m, 1, H), 6.8 (m, 1, H), 4 (m, 3, H), 3.42 (m, 2, H), 3.19 (m, 2, H), 3 (m, 2, H), 2.43 (s, 3, H), 2.25 (s, 3, H). LRMS (esi, positive) m/e 358.30 (M+1).

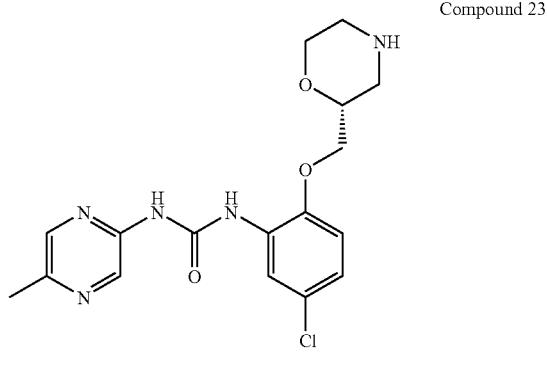

Compound 23

1-[5-Chloro-2-(R-morpholin-2-ylmethoxy)-phenyl]-
3-(5-methyl-pyrazin-2-yl)-urea

Prepared according to the procedure for Compound 4 using (R)-benzyl glycidyl ether and 4-chloro-2-nitro-phenol. $^1$H-NMR (400 MHz, $d_6$-DMSO) δ 10.45 (s, 1, H), 9.6 (br s, 1, H), 9.3 (br s, 1, H), 8.7 (br s, 1, H), 8.3 (s, 1, H), 7.19 (m, 2), 4.2 (m, 2, H), 4 (d, 1, H), 3.84 (t, 1, H), 3.41 (d, 1, H), 3.21 (d, 1, H), 3.02 (m, 2, H), 2.5 (s, 3, H) LRMS (esi, positive) m/e 378.30 (M+1).

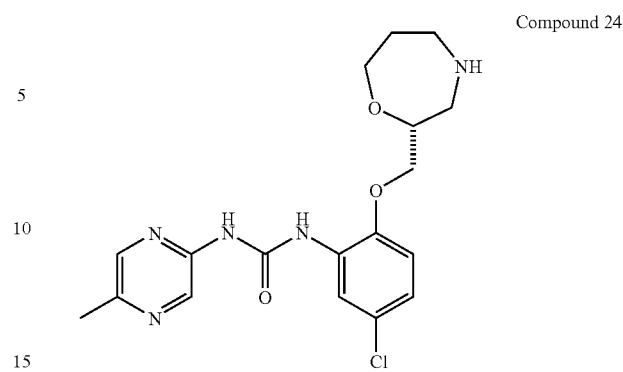

Compound 24

1-[5-Chloro-2-R-([1,4]oxazepan-2-ylmethoxy)-phenyl]-3-(5-methyl-pyrazin-2-yl)-urea Prepared according to the procedure for Compound 1 using (R)-2-hydroxymethyl-[1,4]oxazepane-4-carboxylic acid tert-butyl ester. $^1$H-NMR (300 MHz, $d_6$-DMSO) δ 10.83 (br s, 1H), 8.39 (dd, 1H), 8.18 (s, 1H), 8.04 (br s, 1H), 6.99 (dd, 1H), 6.82 (d, 1H), 4.25-3.98 (m, 2H), 3.90-3.76 (m, 1H), 3.38 (d, 1H), 3.13-3.06 (m, 2H), 3.00 (dd, 1H), 2.54 (s, 3H), 2.06-1.89 (m, 3H). LRMS (ES, positive) m/e 392.3 (M+1).

Compound 25

1-[5-Chloro-2-(1-methyl-piperazin-2-ylmethoxy)-phenyl]-3-(5-methyl-pyrazin-2-yl)-urea Prepared according to the procedure for Compound 7 using 4-chloro-2-nitro-phenol. $^1$H-NMR (400 MHz, $d_6$-DMSO) δ 10.35 (br s, 1, H), 10.2 (s, 1, H), 9.84 (br s, 1, H), 9.6 (s, 1, H), 8.31 (s, 1, H), 8.21 (s, 1, H), 7.08 (m, 2, H), 4.58 (d, 1, H), 4.42 (d, 1, H), 3.7 (m, 6, H), 3 (s, 3, H), 2.44 (s, 3, H). LRMS (esi, positive) m/e 391.40 (M+1).

Compound 26

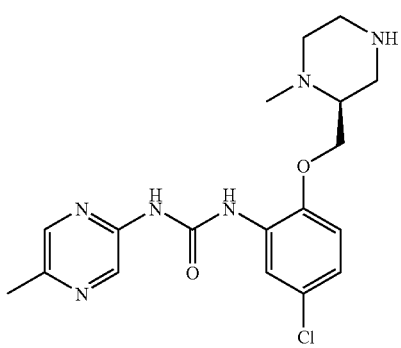

1-[5-Chloro-2-S-(1-methyl-piperazin-2-ylmethoxy)-phenyl]-3-(5-methyl-pyrazin-2-yl)-urea Prepared according to the procedure for Compound 7 using S-piperazine-2-carboxylic acid and 4-chloro-2-nitro-phenol. $^1$H-NMR (400 MHz, CD$_3$OD) δ 8.80 (s, 1, H), 8.28 (d, 2, H), 6.99 (s, 2, H), 4.17 (m, 3, H), 3.1 (d, 1, H), 2.92 (d, 2, H), 2.84 (t, 1, H), 2.5 (s, 3, H), 2.45 (m, 2, H), 2.42 (s, 3, H). LRMS (esi, positive) m/e 391.30 (M+1).

Compound 27

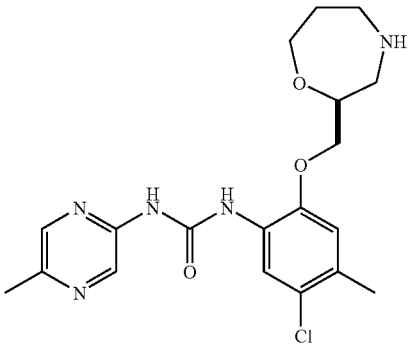

1-[5-Chloro-4-methyl-2-S-([1,4]-oxazepan-2-yl-methoxy)-phenyl]-3-(5-methyl-pyrazin-2-yl)-urea Prepared according to the procedure for Compound 1 using 4-chloro-5-methyl-2-nitro-phenol which was prepared according to the procedure for Compound 4, Step 2. $^1$H-NMR (300 MHz, d$_6$-DMSO) δ 10.2 (s, 1H), 8.62 (s, 1H), 8.27 (s, 1H), 8.24 (s, 1H), 7.32 (m, 1H), 7.18 (s, 1H), 4.09-3.91 (m, 3H), 3.90-3.79 (m, 1H), 3.77-3.62 (m, 1H), 3.14 (d, 1H), 2.85 (m, 1H), 2.73 (s, 2H), 2.39 (s, 3H), 2.27 (s, 1H), 1.82-1.67 (m, 2H). LRMS (ES, positive) m/e 406.2 (M+1).

Compound 28

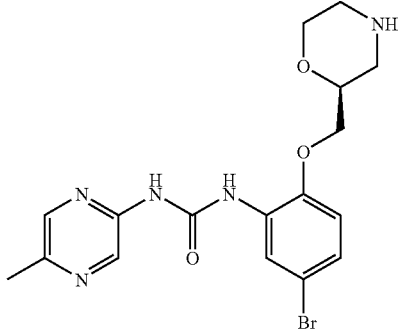

1-[5-Bromo-2-(S-morpholin-2-ylmethoxy)-phenyl]-3-(5-methyl-pyrazin-2-yl)-urea

Prepared according to the procedure for Compound 4 using 4-bromo-2-nitro-phenol. $^1$H-NMR (400 MHz, d$_6$-DMSO), δ 10.30 (s, 1, H), 8.63 (br s, 1, H), 8.43 (s, 1, H), 8.22 (s, 1, H), 7.15 (m, 1, H), 7.05 (d, 1, H), 4.08 (m, 3, H), 3.82 (m, 2, H), 3.47 (t, 1, H), 3.17 (s, 2, H), 3 (d, 1, H), 3.07 (s, 3, H), 2.68 (m, 2, H). LRMS (esi, positive) m/e 423.90 (M+1).

Compound 29

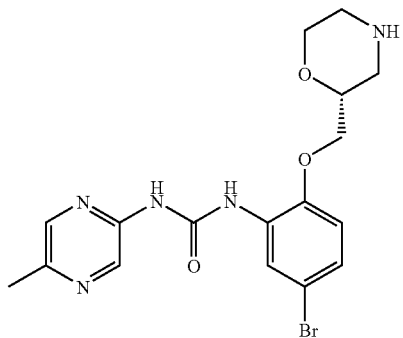

1-[5-Bromo-2-R-(R-morpholin-2-ylmethoxy)-phenyl]-3-(5-methyl-pyrazin-2-yl)-urea

Prepared according to the procedure for Compound 4 using (R)-benzyl glycidyl ether and 4-bromo-2-nitro-phenol. $^1$H-NMR (400 MHz, d$_6$-DMSO), δ 10.30 (br s, 1, H), 8.65 (br s, 1, H), 8.43 (s, 1, H), 8.25 (s, 1, H), 7.18 (dd, 1, H), 7.03 (d, 1, H), 4.03 (m, 2, H), 3.82 (m, 2, H), 3.52 (t, 2, H), 3.19 (d, 1, H), 3 (d, 1, H), 2.76 (m, 2, H), 2.43 (s, 3, H). LRMS (esi, positive) m/e 443.90 (M+1).

Compound 30

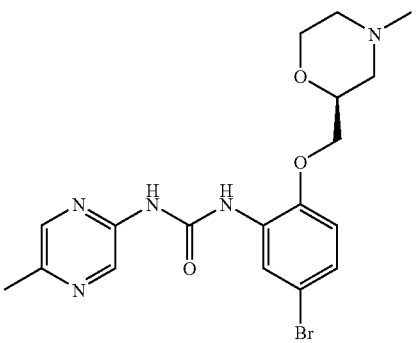

1-[5-Bromo-2-S-(4-methyl-morpholin-2-yl-methoxy)-phenyl]-3-(5-methyl-pyrazin-2-yl)-urea Prepared according to the procedure for Compound 4 using 4-bromo-2-nitro-phenol and the procedures for Compound 2, Step 4 and Compound 5, Steps 4 and 5. $^1$H-NMR (400 MHz, CDCl$_3$), δ 11.43 (br s, 1, H), 9.02 (s, 1, H), 8.6 (s, 1, H), 8.33 (s, 1, H), 8.2 (s, 1, H), 7.12 (d, 1, H), 6.76 (d, 1, H), 4 (m, 3, H), 3.8 (t, 1, H), 3.02 (d, 1, H), 2.73 (d, 1, H), 2.51 (s, 3, H), 2.3 (t, 1, H), 2.22 (s, 3, H), 2.08 (t, 1, H).

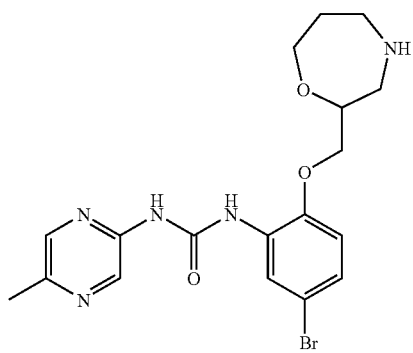

Compound 31

1-[5-Bromo-2-([1,4]oxazepan-2-ylmethoxy)-phenyl]-3-(5-methyl-pyrazin-2-yl)-urea

Prepared according to the procedure for Compound 6 using 4-bromo-2-nitro-phenol, which was prepared according to the procedure for Compound 4, Step 2. $^1$H-NMR (400 MHz, CDCl$_3$), δ 8.72 (br s, 1, H), 8.48 is, 1, H), 8.45 (s, 1, H), 7.11 (d, 1, H), 6.75 (d, 1, H), 4.02 (m, 3, H), 3.8 (m, 1, H), 3.21 (d, 1, H), 2.97 (m, 2, H), 2.51 (s, 3, H), 1.92 (br m, 2, H). LRMS (esi, positive) m/e 436.00 (M+1).

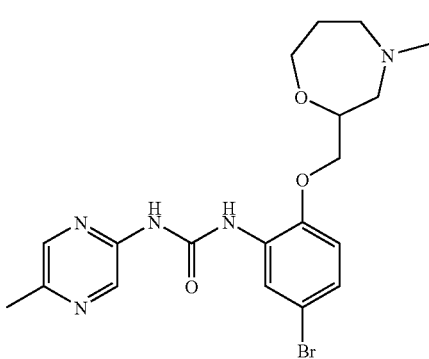

Compound 32

1-[5-Bromo-2-(4-methyl-[1,4]oxazepan-2-ylmethoxy)-phenyl]-3-(5-methyl-pyrazin-2-yl)-urea Prepared according to the procedure for Compound 6, using 4-bromo-2-nitro-phenol, and by the procedure for Compound 5, Step 5. $^1$H-NMR (400 MHz, CDCl$_3$), δ 8.25 (s, 1,H), 8.23 (s, 1, H), 7.1 (d, 1, H), 6.72 (d, 1, H), 4.19 (m, 1, H), 4 (m, 1, H), 3.95 (m, 2, H), 3.42 (br s, 1, H), 3.02 (d, 1, H), 2.84 (m, 1, H), 2.62 (t, 1, H), 2.5 (s, 3, H), 2.4 (s, 3, H), 2 (m, 2, H). LRMS (esi, positive) m/e 451.90 (M+1).

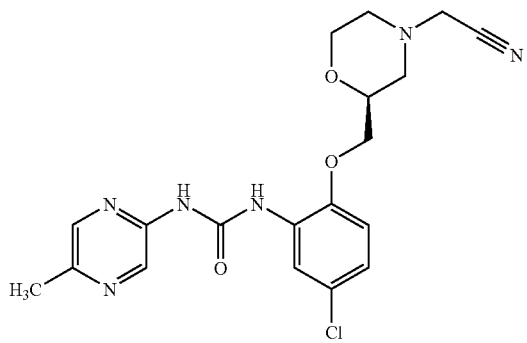

Compound 33

1-[5-Chloro-2-S-(4-cyanomethyl-morpholin-2-yl-methoxy)-phenyl]-3-(5-methyl-pyrazin-2-yl)-urea 1-[5-Chloro-2-(S-morpholin-2-ylmethoxy)-phenyl]-3-(5-methyl-pyrazin-2-yl)-urea (0.189 g, 0.5 mmol) was suspended in DMF (2 mL). Potassium carbonate (0.104 g, 0.75 mmol) and bromoacetonitrile (0.035 mL, 0.5 mmol) were added and the reaction mixture was heated to 80° C. for 8 h. The reaction mixture was allowed to cool to room temperature and quenched by addition of H$_2$O (10 mL). The resulting solid was collected by filtration and recrystallized from MeOH to give the product as a white powder (0.072 g). $^1$H-NMR (400 MHz, d$_6$-DMSO) δ 10.46 (br s, 1H), 10.26 (br s, 1H), 8.63 (br s, 1H), 8.31 (d, 1H), 8.17 (s, 1H), 7.10 (d, 1H), 7.03 (dd, 1H), 4.14 (dd, 1H), 4.09 (dd, 1H), 3.96-4.01 (m, 1H), 3.91-3.95 (m, 1H). 3.81 (d, 1H), 3.72 (d, 1H), 3.64 (td, 1H), 2.95 (br d, 1H), 2.72 (br d, 1H), 2.43 (s, 3H), 2.32 (td, 1H), 2.18 (t, 1H). LRMS (esi, positive) m/e 417 (M+1).

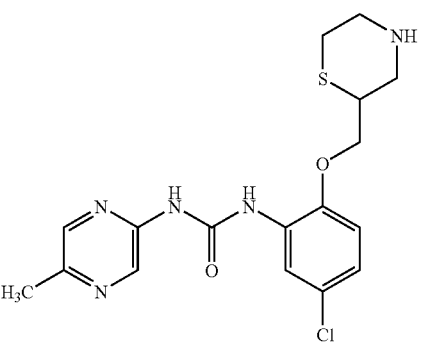

Compound 34

1-[5-Chloro-2-(thiomorpholin-2-ylmethoxy)-phenyl]-3-(5-methyl-pyrazin-2-yl)-urea Prepared according to the procedure for Compound 2, Step 2 (using 2-hydroxymethyl-thiomorpholine-4-carboxylic acid tert-butyl ester obtained from thiomorpholine-2,4-dicarboxylic acid 4-tert-butyl ester according to the procedure for Compound 2, Step 1), and the procedures for Compound 3, Step 2 and Compound 2, Steps 4 and 5. $^1$H-NMR (400 MHz, d$_6$-DMSO) δ 10.48 (br s, 1H), 10.27 (br s, 1H), 8.62 (br s, 1H), 8.31 (d, 1H), 8.21 (s, 1H), 7.12 (d, 1H), 7.03 (dd, 1H), 4.36 (t, 1H), 4.12 (dd, 1H), 3.24 (dd, 1H), 3.10-3.17 (m, 1H), 2.99 (dd, 1H), 2.94-2.98 (m, 1H), 2.89 (ddd, 1H), 2.71 (ddd, 1H), 2.46-2.48 (m, 1H), 2.44 (s, 3H). LRMS (esi, positive) m/e 394 (M+1).

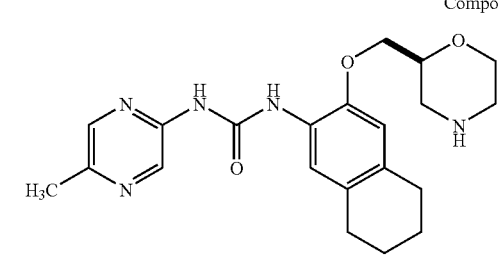

Compound 35

1-(5-Methyl-pyrazin-2-yl)-3-[3-S-(morpholin-2-ylmethoxy)-5,6,7,8-tetrahydro-naphthalen-2-yl]-urea Prepared according to the procedure for Compound 3, Step 1 (using (S)-2-hydroxymethyl-morpholine-4-carboxylic acid tert-butyl ester prepared from S-morpholine-2,4-dicarboxylic acid 4-tert-butyl ester according to the procedure for Compound 2, Step 1 and 3-nitro-5,6,7,8-tetrahydro-naphthalen-2-ol, prepared according to the procedure for Compound 4, Step 2, and the procedure for Compound 1, Step 5. $^1$H-NMR (400 MHz, d$_6$-DMSO) δ 10.09 (br, 1, H), 10.05 (s, 1, H), 8.60 (br s, 1, H), 8.17 (s, 1, H), 7.86 (s, 1, H), 6.68 (s, 1, H), 3.97 (m, 1, H), 3.89 (m, 1, H), 3.78 (m, 2, H), 3.31 (t, 1, H), 2.98 (d, 1, H), 2.63 (m, 6, H), 2.44 (m, 1, H), 2.41 (s, 3, H), 1.68 (m, 4, H).

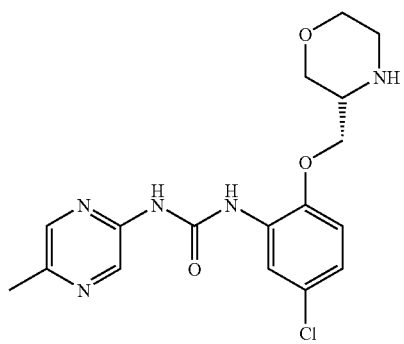

Compound 36

1-[5-Chloro-2-S-(morpholin-3-ylmethoxy)-phenyl]-3-(5-methyl-pyrazin-2-yl)-urea Prepared according to the procedure for Compound 2 using morpholine-3-S-4-dicarboxylic acid 4-tert-butyl ester. $^1$H-NMR (400 MHz, d$_6$-DMSO) δ 10.22 (s, 1, H), 9.96 (br, 1, H), 8.74 (s, 1, H), 8.29 (d, 1, H), 8.18 (s, 1, H), 7.04 (m, 2, H), 3.94 (m, 3, H) 3.70 (br d, 1, H), 3.42 (m, 1, H), 3.23 (m, 2, H), 2.83 (br s, 2, H), 2.43 (s, 3, H).

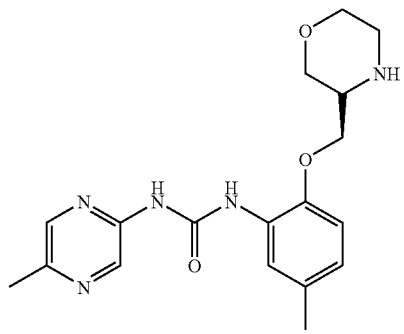

Compound 37

1-[5-Methyl-2-R-(morpholin-3-ylmethoxy)-phenyl]-3-(5-methyl-pyrazin-2-yl)-urea Prepared according to the procedure for Compound 2 using 4-methyl-2-nitro-phenol. $^1$H-NMR (400 MHz, d$_6$-DMSO) δ 10.08 (br s, 1, H), 9.76 (br, 1, H), 8.17 (s, 1, H), 8.03 (d, 1, H), 6.90 (d, 1, H), 6.80 (d, 1, H), 3.88 (m, 3, H), 3.70 (br d, 2, H), 3.41 (m, 1, H), 3.20 (m, 2, H), 2.82 (m, 2, H), 2.43 (s, 3, H), 2.24 (s, 3, H).

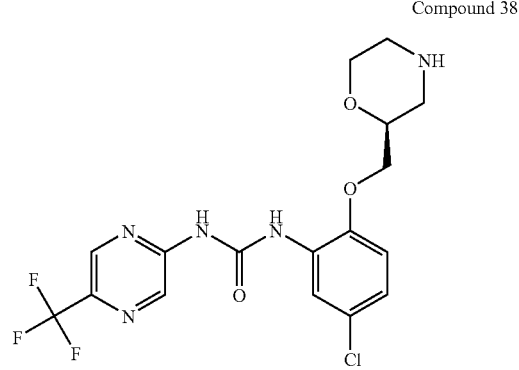

Compound 38

1-[5-Chloro-2-S-(morpholin-2-ylmethoxy)-phenyl]-3-(5-trifluoromethyl-pyrazin-2-yl)-urea Prepared according to the procedure for Compound 1, Steps 2 through 5, using 5-trifluoromethyl-pyrazin-2-ylamine prepared according to the method of Miesel U.S. Pat. No. 4,293,552 and (S)-2-hydroxymethyl-morpholine-4-carboxylic acid tert-butyl ester. $^1$H-NMR (d$_6$-DMSO) δ 10.85 (bs, 1H), 9.97 (bs, 1H), 9.11 (bs, 1H), 8.98 (bs, 1H), 8.73 (bs, 1H), 8.22 (bs, 1H), 7.08 (bs, 1H), 4.19-3.73 (m, 6H), 3.32-2.98 (m, 4H). LRMS (esi, positive) m/e 432 (M+1).

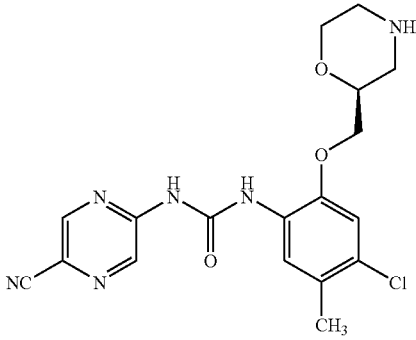

Compound 39

1-[4-Chloro-5-methyl-2-S-(morpholin-2-ylmethoxy)-phenyl]-3-(5-cyano-pyrazin-2-yl)-urea Prepared according to the procedures for Compound 5, Steps 1 through 4 using 5-chloro-4-methyl-2-nitro-phenol prepared from 3-chloro-4-methyl-phenol according to the procedure for Compound 4, Step 2. $^1$H-NMR (300 MHz, CDCl$_3$) δ 10.39 (br s, 1H), 9.05 (br s, 1H), 8.74 (s, 1H), 8.68 (s, 1H), 8.18 (s, 1H), 6.91 is, 1H), 4.04 (m, 4H), 3.78 (m, 1H), 3.19 (d, 1H), 2.97 (m, 2H), 2.78 (m, 1H), 2.36 (s, 3H). LCMS (esi, positive) m/z 403.16 (M+1).

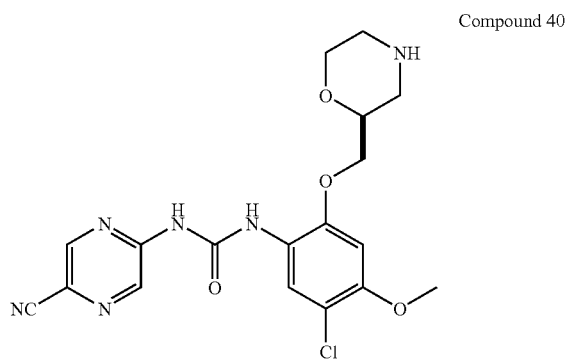

Compound 40

1-[5-Chloro-4-methoxy-2-(S-morpholin-2-yl-methoxy)-phenyl]-3-(5-cyano-pyrazin-2-yl)-urea Prepared according to the procedure for Compound 1, Step 2 (using 5-amino-pyrazine-2-carbonitrile prepared according to the procedures for Compound 5, Steps 1 and 2) and the procedures for Compound 1, Steps 4 and 5 (using 2-hydroxymethyl-5-morpholine-4-carboxylic acid tert-butyl ester and 4-chloro-5-methoxy-2-nitro-phenol, prepared according to the procedure for Compound 4, Step 2). $^1$H-NMR (300 MHz, $d_6$-DMSO) δ 10.82 (s, 1H), 9.93 (s, 1H), 8.95 (s, 1H), 8.81 (s, 1H), 8.14 (s, 1H), 6.93 (s, 1H), 4.25 (s, 2H), 4.13-3.98 (m, 2H), 3.83 (s, 3H), 3.61 (t, 1H), 3.41-3.19 (m, 2H), 3.17-2.91 (m, 2H). LRMS (ES, positive) m/e 419.1 (M+1).

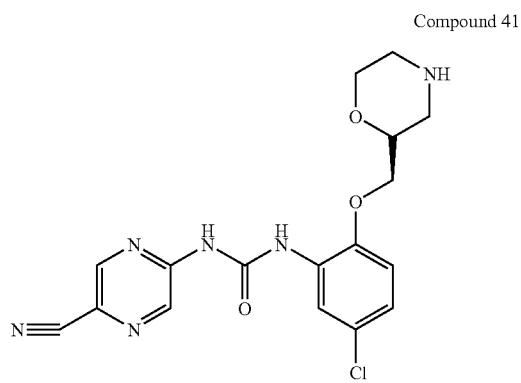

Compound 41

1-[5-Chloro-2-S-(morpholin-2-ylmethoxy)-phenyl]-3-(5-cyano-pyrazin-2-yl)-urea Prepared according to the procedure for Compound 1, Step 2 (using 5-amino-pyrazine-2-carbonitrile prepared according to the procedures for Compound 5, Steps 1 and 2) and the procedures for Compound 1, Steps 4 and 5 (using 2-hydroxymethyl-5-morpholine-4-carboxylic acid tert-butyl ester and 4-chloro-2-nitro-phenol). $^1$H-NMR ($d_6$-DMSO) δ 10.97 (bs, 1H), 10.02 (bs, 1H), 9.05 (bs, 1H), 8.95 (s, 1H), 8.85 (s, 1H), 8.2 (s, 1H), 7.10 (m, 1H), 3.96-4.24 (m, 4H), 3.68-3.78 (m, 2H), 3.3 (m, 2H), 3.0 (m, 2H). LRMS (esi, positive) m/e 388 (M+1).

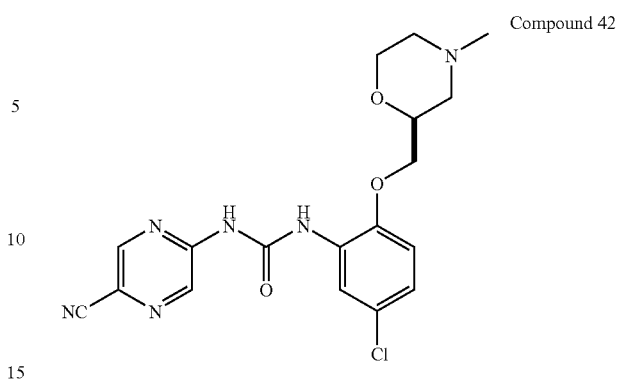

Compound 42

1-[5-Chloro-2-S-(4-methyl-morpholin-2-yl-methoxy)-phenyl]-3-(5-cyano-pyrazin-2-yl)-urea Step 1: 1-[5-Chloro-2-(morpholin-2-ylmethoxy)-phenyl]-3-(5-cyano-pyrazin-2-yl)-urea. Prepared according to the procedure for Compound 1, Step 2 (using 5-amino-pyrazine-2-carbonitrile prepared according to the procedures for Compound 5, Steps 1 and 2) and the procedures for Compound 1, Steps 4 and 5 (using 2-hydroxymethyl-5-morpholine-4-carboxylic acid tert-butyl ester and 4-chloro-2-nitro-phenol) to give 0.27 g of product.

Step 2: 1-[5-Chloro-2-(morpholin-2-ylmethoxy)-phenyl]-3-(5-cyano-pyrazin-2-yl)-urea (0.276 g, 0.73 mmol) was suspended in DMF (5 mL) and treated with potassium carbonate (0.15 g, 1.1 mmol) and methyl iodide (0.046 mL, 0.73 mmol). The mixture became homogeneous and was stirred at room temperature for 4 h. The reaction was quenched with the addition of water (20 mL) and extracted with a 3:1 mixture of $CHCl_3$:iPrOH (3×25 mL). The combined organic layers were concentrated-under reduced pressure and the residue was triturated with EtOAc. Filtration provided 0.214 g of the product as a white solid. $^1$H-NMR (300 MHz, $d_6$-DMSO) δ 11.01 (s, 1H), 10.16 (s, 1H), 8.86 (d, 2H), 8.27 (d, 1H), 8.17 (s, 1H), 7.18 (m, 2H), 4.25-4.06 (m, 2H), 3.95 (m, 1H), 3.83 (d, 1H), 3.61 (t, 1H), 2.89 (d, 1H), 2.65 (d, 1H), 2.18 (s, 3H), 2.02 (td, 1H), 1.83 (t, 1H). LRMS (ES, positive) m/e 403.0 (M+1).

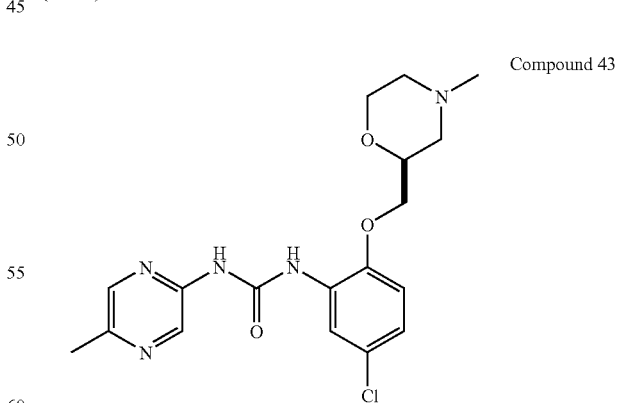

Compound 43

1-[5-Chloro-2-(S-4-methyl-morpholin-2-yl-methoxy)-phenyl]-3-(5-methyl-pyrazin-2-yl)-urea Prepared according to the procedure for Compound 42, Step 2 using 1-[5-chloro-2-(S-4-methyl-morpholin-2-ylmethoxy)-phenyl]-3-(5-methyl-pyrazin-2-yl)-urea.
$^1$H-NMR (300 MHz, $d_6$-DMSO) δ 10.54 (br s, 1H), 10.24 (s, 1H), 8.73 (s, 1H), 8.30 (s, 1H), 8.27 (s, 1H), 7.12-6.93 (m, 2H), 4.17-3.81 (m, 4H), 3.59 (t, 1H), 3.91 (d, 1H), 2.64 (d, 1H), 2.43 (s, 3H), 2.18 (s, 3H), 2.03 (td, 1H), 1.82 (t, 1H). LRMS (ES, positive) m/e 392.1 (M+1).

Therapeutic Methods

Compounds of the invention can be used to treat conditions involving aberrant cell proliferation. For example, the compounds can be used to potentiate the therapeutic effects of radiation and/or a chemotherapeutic agent used in the treatment of cancers and other cell proliferation indications involving eukaryotic cells, including those in humans and other animals. In general, the present compounds inhibit aberrantly proliferating cells, both cancerous and noncancerous. For example, compounds of the invention can be used to enhance treatment of tumors customarily treated with an antimetabolite, e.g., methotrexate, gemcitabine, or 5-fluorouracil (5-FU).

Use of compounds of the present invention can result in a partial or complete regression of aberrantly proliferating cells, i.e., the reduction or elimination of such cells from the cell population. For example, when the population of aberrantly proliferating cells is tumor cells, compounds of the invention can be used to retard the rate of tumor growth, decrease the number of tumors, and/or induce partial or complete tumor regression.

Compounds of the present invention can be used in vivo or ex vivo when no aberrant cell proliferation has been identified or when no aberrant cell proliferation is ongoing, but when aberrant cell proliferation is suspected or expected. Compounds of the present invention also can be used when aberrant cell proliferation has been previously treated in order to prevent or inhibit recurrence of the same.

One method of the present invention comprises administration of a therapeutically effective amount of a present Chk1 inhibitor, in combination with a chemotherapeutic agent, to an individual in need thereof. Alternatively, a method of the present invention comprises administration of a therapeutically effective amount of at least one present Chk1 inhibitor to an individual in need thereof, in combination with an antibody, e.g., herceptin, that has activity in inhibiting the proliferation of cancer cells.

Cancers, therefore, are susceptible to enhanced treatment by administration of a present Chk1 inhibitor in combination with a chemotherapeutic agent or an antibody. Cancers treatable by the present invention include carcinomas and sarcomas that are characterized by solid tumors, and cancers of the myeloid or lymphoid systems, including leukemias, lymphomas, and other cancers that typically lack a tumor mass, but are distributed in the vascular or lymphoreticular systems. These cancers include, for example, colorectal cancers, head and neck cancers, pancreatic cancers, breast cancers, gastric cancers, bladder cancers, vulvar cancers, leukemias, lymphomas, melanomas, renal cell carcinomas, ovarian cancers, brain cancers, osteosarcomas, and lung cancers.

Compounds of the present invention, therefore, are useful in cancers mediated by Chk1 activity. More particularly, Chk1 activity is associated with forms of cancer including, but not limited to, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute antilymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

A compound of the present invention also can be used to radiosensitize cells. Diseases treatable with radiation include, but are not limited to neoplastic diseases, benign and malignant tumors, and cancerous cells. Radiation treatment employs electromagnetic radiation such as gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Some cancer treatment protocols currently employ radiosensitizers activated by electromagnetic radiation, e.g., X-rays. Examples of X-ray-activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives thereof.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to the Chk1 inhibitor, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents or methods that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

Chemotherapeutic agents that can be used in combination with a compound of the present invention to treat a cancer include, but are not limited to, alkylating agents, antimetabolites, hormones and antagonists thereof, radioisotopes, antibodies, as well as natural products, and combinations thereof. For example, an inhibitor compound of the present invention can be administered with antibiotics, such as doxorubicin and other anthracycline analogs, nitrogen mustards, such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct antineoplastic modalities." Additional chemotherapeutic agents useful in the invention include hormones and antagonists thereof, radioisotopes, antibodies, natural products, and combinations thereof. Examples of chemotherapeutic agents useful in methods employing compounds of the present invention are listed in the following table.

TABLE 1

A) Alkylating agents
  i) Nitrogen mustards
     mechlorethamine
     cyclophosphamide
     ifosfamide
     melphalan
     chloroambucil
  ii) Nitrosoureas
     carmustine (BCNU)
     lomustine (CCNU)
     semustine (methyl-CCNU)
  iii) Ethylenimine/Methyl-melamine
     triethylenemelamine (TEM)
     triethylene thiophosphoramide (thiotepa)
     hexamethylmelamine (HMM, altretamine)
  iv) Alkyl sulfonates
     busulfan
  v) Triazines
     dacarbazine (DTIC)
B) Antimetabolites
  i) Folic Acid analogs
     methotrexate
     trimetrexate
     pemetrexed (multitargeted antifolate)
  ii) Pyrimidine analogs
     5-fluorouracil
     fluorodeoxyuridine
     gemcitabine
     cytosine arabinoside (AraC, cytarabine)
     5-azacytidine
     2,2'-difluorodeoxy-cytidine
  iii) Purine analogs
     6-mercaptopurine
     6-thioguanine
     azathioprine TABLE 1-continued 2'-deoxycoformycin (pentostatin)
     erythrohydroxynonyl-adenine (EHNA)
     fludarabine phosphate
     2-chlorodeoxyadenosine
     (cladribine, 2-CdA)
C) Type I Topoisomerase inhibitors
     camptothecin
     topotecan
     irinotecan
D) Biological response modifiers
     G-CSF
     GM-CSF
E) Differentiation agents
     retinoic acid derivatives
F) Hormones and antagonists
  i) Adrenocorticosteroids /antagonists
     prednisone and equivalents
     dexamethasone
     ainoglutethimide
  ii) Progestins
     hydroxyprogesterone caproate
     medroxyprogesterone acetate
     megestrol acetate
  iii) Estrogens
     diethylstilbestrol
     ethynyl estradiol and equivalents
  iv) Antiestrogen
     tamoxifen
  v) Androgens
     testosterone propionate
     fluoxymesterone and equivalents
  vi) Antiandrogens
     flutamide
     gonadotropin-releasing hormone analogs
     leuprolide
  vii) Nonsteroidal antiandrogens
     flutamide
G) Natural products
  i) Antimitotic drugs
  ii) Taxanes
     paclitaxel
     vinca alkaloids
     vinblastine (VLB)
     vincristine
     vinorelbine
     Taxotere ® (docetaxel)
     estramustine
     estramustine phosphate
  iii) Epipodophylotoxins
     etoposide
     teniposide
  iv) Antibiotics
     actimomycin D
     daunomycin (rubidomycin)
     doxorubicin (adriamycin)
     mitoxantroneidarubicin
     bleomycin
     splicamycin (mithramycin)
     mitomycin C
     dactinomycin
     aphidicolin
  v) Enzymes
     L-asparaginase
     L-arginase
H) Radiosensitizers
     metronidazole
     misonidazole
     desmethylmisonidazole
     pimonidazole
     etanidazole
     nimorazole
     RSU 1069
     EO9
     RB 6145
     SR4233
     nicotinamide
     5-bromodeoxyuridine
     5-iododeoxyuridine
     bromodeoxycytidine

TABLE 1-continued

I) Miscellaneous agents
  i) Platinum coordination complexes
    cisplatin
    carboplatin
    oxaliplatin
    anthracenedione
    mitoxantrone
  ii) Substituted urea
    hydroxyurea
  iii) Methylhydrazine derivatives
    N-methylhydrazine (MIH)
    procarbazine
  iv) Adrenocortical suppressant
    mitotane (o,p'-DDD)
    ainoglutethimide
J) Cytokines
    interferon (α, β, γ)
    interleukin-2
K) Photosensitizers
    hematoporphyrin derivatives
    Photofrin ®
    benzoporphyrin derivatives
    Npe6
    tin etioporphyrin (SnET2)
    pheoboride-a
    bacteriochlorophyll-a
    naphthalocyanines
    phthalocyanines
    zinc phthalocyanines
L) Radiation
    X-ray
    ultraviolet light
    gamma radiation
    visible light
    infrared radiation
    microwave radiation Examples of chemotherapeutic agents that are particularly useful in conjunction with radiosensitizers include, for example, camptothecin, carboplatin, cisplatin, daunorubicin, doxorubicin, interferon (alpha, beta, gamma), irinotecan, hydroxyurea, chlorambucil, 5-fluorouracil (5-FU), methotrexate, 2-chloroadenosine, fludarabine, azacytidine, gemcitabine, pemetrexed, interleukin 2, irinotecan, docetaxel, paclitaxel, topotecan, and therapeutically effective analogs and derivatives of the same.

In accordance with the present invention, compounds of the present invention are useful in combination with gemcitabine, alone or further with paclitaxel. Compounds of the present invention also are useful in combination with pemetrexed, alone or further with cisplatin, carboplatin, or other platins. A present Chk1 inhibitor also can be administered in combination with gemcitabine and pemetrexed.

A present Chk1 inhibitor administered in combination with gemcitabine can be useful in the treatment of, for example, pancreatic carcinoma, leiomyosarcoma of the uterus, bone sarcoma, metastatic nonsmall cell lung cancer, extremity and trunk soft tissue sarcoma, renal cell cancer, adenocarcinoma, and Hodgkin's disease. A present Chk1 inhibitor administered with pemetrexed can be useful in the treatment of mesothelioma.

Compounds of the present invention also can potentiate the efficacy of drugs used in the treatment of inflammatory diseases, conditions, or disorders characterized by aberrant cell proliferation. Examples of inflammatory diseases that can be treated with compounds of the present invention include, but are not limited to, rheumatoid arthritis (RA), psoriasis, vitiligo, Wegener's granulomatosis, systemic-onset juvenile chronic arthritis (JCA), and systemic lupus erythematosus (SLE). Treatment of arthritis, Wegener's granulornatosis, and SLE often involves the use of immunosuppressive therapies, such as ionizing radiation, methotrexate, and cyclophosphamide. Such treatments typically induce, either directly or indirectly, DNA damage. Inhibition of Chk1 activity within the offending immune cells render the cells more sensitive to control by these standard treatments. Psoriasis and vitiligo commonly are treated with ultraviolet radiation (UV) in combination with a psoralen. The compounds of the present invention enhance the killing effect of UV and a psoralen, and increase the therapeutic index of this treatment regimen. In general, compounds of the present invention potentiate control of inflammatory disease cells when used in combination with immunosuppressive drugs.

The compound of the present invention also can be used in methods of treating other noncancerous conditions characterized by aberrantly proliferating cells. Such conditions include, but are not limited to, atherosclerosis, restenosis, vasculitis, nephritis, retinopathy, renal disease, proliferative skin disorders, psoriasis, keloid scarring, actinic keratosis, Stevens-Johnson Syndrome, osteoporosis, hyperproliferative diseases of the eye including epithelial down growth, proliferative vitreoretinopathy (PVR), diabetic retropathy, Hemangio-proliferative diseases, ichthyosis, and papillomas.

One preferred method of administering a Chk1 inhibitor of the present invention is described in Keegan et al., PCT application No. PCT/US2004/30806, filed Sep. 17, 2004, which is based on U.S. Provisional Application Ser. No. 60/503,925, filed Sep. 17, 2003, the entire disclosure of which is incorporated by reference. Such methods for inhibiting aberrant cell proliferation involve scheduling administration of a Chk1 activator (e.g., a chemotherapeutic agent) and a Chk1 inhibitor according to the present invention. In this method, at least one Chk1 activator is administered at a dose and for a time sufficient to induce substantial synchronization of cell cycle arrest in proliferating cells. Upon achieving substantial phase synchronization, at least one Chk1 inhibitor is administered to abrogate the cell cycle arrest and induce therapeutic cell death. The method is useful with any Chk1 activator, and finds application in treating or preventing cancerous and noncancerous conditions involving aberrant cell proliferation.

A population of aberrantly proliferating cells can be contacted with one, or more than one, Chk1 inhibitor of the invention. If more than one Chk1 inhibitor is used, the Chk1 inhibitors can be contacted with the cells using the same or different methods (e.g., simultaneously or sequentially, for the same or different durations, or by the same or different moldalities) as determined by the skilled artisan, e.g., an attending-physician (in the case of human patients) or a laboratory experimentalist (in the case of an in vitro or ex vivo procedure).

A population of aberrantly proliferating-cells also can be contacted with one or more Chk1 activator. If more than one Chk1 activator is used, the Chk1 activators can be contacted with the cells using the same or different methods, generally as described in the context of Chk1 inhibitors above.

Compounds of the present invention can be applied to cell populations ex vivo. For example, the present compounds can be used ex vivo to obtain information concerning the optimal schedule and/or dosing for administering a Chk1 inhibitor for a given indication, cell type, patient, and/or other treatment parameter. This information can be used for experimental purposes or in a clinic to determine protocols for in vivo treatment. Other ex vivo uses for compounds of the present invention will be apparent to persons skilled in the art.

As appreciated by persons skilled in the art, additional active or ancillary agents may be used in the methods described herein. As also appreciated by persons skilled in the art, reference herein to treatment extends to prophylaxis, as well as to treatment of established diseases or symptoms.

The amount of a compound of the invention required for use in treatment varies with the nature of the condition being treated, and with the age and the condition of the patient, and is ultimately determined by the attendant physician or veterinarian. In general, however, doses administered for adult human treatment typically are in the range of 0.001 mg/kg to about 100 mg/kg per day. The dose can be administered in a single dose, or as multiple doses administered at appropriate intervals, for example as two, three, four or more subdoses per day. In practice, the physician determines the dosing regimen suitable for an individual patient, and the dosage varies with the age, weight, and response of the particular patient. The above dosages are exemplary of the average case, but individual instances exist wherein higher or lower dosages are merited, and such are within the scope of the present invention.

Contact of the cell population with a present Chk1 inhibitor, at any dose, is for a time sufficient to achieve substantial abrogation of the cell cycle checkpoint. Typically, though not necessarily, such times include up to about 72 hours to about 96 hours, depending upon various factors. In some embodiments, it is desirable or necessary to administer Chk1 inhibitor over a period of up to about several weeks or more, as determined by the attending physician or technician. Thus, a present Chk1 inhibitor typically can be administered for up to about 1 hour, up to about 2 hours, up to about 3 hours, up to about 4 hours, up to about 6 hours, up to about 12 hours, up to about 18 hours, up to about 24 hours, up to about 48 hours, or up to about 72 hours. Persons skilled in the art appreciate that the ranges of time expressed herein are merely exemplary and that ranges and subranges within and outside those expressed also are within the scope of the invention.

Chk1 inhibitors of the present invention can be administered over a plurality of doses. For example, the Chk1 inhibitor can be given at a frequency of: four doses delivered as one dose per day at four-day intervals (q4d×4); four doses delivered as one dose per day at three-day intervals (q3d×4); one dose delivered per day at five-day intervals (qd×5), one dose per week for three weeks (qwk3); five daily doses, with two days rest, and another five daily doses (5/2/5); or, any dose regimen determined to be appropriate for the circumstance.

EXAMPLES

Example 1

Determination of $IC_{50}$ Values of Chk1 Inhibitors

Human Chk1 cDNA was identified and cloned as described previously in International Application Publication No. WO 99/11795, filed Sep. 4, 1998. A FLAG® tag was inserted in frame with the amino terminus of the full-length Chk1. The 5' primer contains an EcoRI site, a Kozak sequence, and also encodes a FLAG® tag for affinity purification using the M2 Antibody (Sigma, St. Louis, Mo.). The 3' primer contains a SalI site. The PCR-amplified fragment was cloned into pCI-Neo as an EcoRI-SalI fragment (Invitrogen, Carlsbad, Calif.), then subcloned as an EcoRI-NotI fragment into pFastBacI (Gibco-BRL, Bethesda, Md.). Recombinant baculovirus was prepared as described in the Gibco-BRL Bac-to-Bac manual and used to infect Sf-9 cells grown in CCM3 medium (Hy-Clone Laboratories, Logan, Utah) for expression of FLAG®-tagged Chk1 protein.

FLAG®-tagged Chk1 was purified from frozen pellets of baculovirus-infected SF9 cells. Frozen cell pellets were mixed with an equal volume of 2× lysis buffer containing 100 mM Tris-HCl pH 7.5, 200 mM NaCl, 50 mM B-glycerophosphate, 25 mM NaF, 4 mM $MgCl_2$, 0.5 mM EGTA, 0.2% TWEEN®-20, 2 mM sodium vanadate, 2 mM DTT, and a cocktail of protease inhibitors (Complete mini, Boehringer Mannheim 2000 catalog #1836170). Cells then were dounced 20 times with the loose pestle of a dounce homogenizer and centrifuged at 48,400×g for 1 hour. The M2 affinity was prewashed with 10 column volumes of 50 mM glycine pH 3.5 followed by 20 mM Tris pH 7.5, 150 mM NaCl alternating three times and ending with a Tris NaCl wash. The column then was washed with 25 column volumes of 20 mM Tris pH 7.5, 150 mM NaCl, 0.1% TWEEN®-20, 1 mM EGTA, 1 mM EDTA and 1× complete mini protease tablets. The cleared lysate then was bound to M2 affinity resin in batch at 4° C. for 4 h. The mixture of resin and lysate then was poured into a column and the flow through collected. The resin was washed with 10 column volumes of 20 mM Tris pH 7.5, 150 mM NaCl, and 3 mM N-octyl glucoside. FLAG®-tagged Chk1 then was eluted from the column with 6 column volumes of cold 20 mM Tris pH 7.5, 150 mM NaCl, 3 mM N-octyl glucoside containing 0.5 mg/mL FLAG® peptide (Sigma, 2000 Catalog #F-3290). Three fractions were collected an analyzed for the presence of FLAG-tagged Chk1.

The assay for Chk1 kinase activity that includes 100 ng purified FLAG®-Chk1 (150 pmol of ATP/min), 20 μm Cdc25C peptide (H-leu-tyr-arg-ser-pro-ser-met-pro-glu-asn-leu-asn-arg-arg-arg-arg-OH) (SEQ ID NO: 1), 4 μm ATP, 2 μCi [$^{32}$P]γ-ATP, 20 mM Hepes pH 7.2, 5 mM $MgCl_2$, 0.1% NP40, and 1 mM DTT. Reactions were initiated by the addition of ATP-containing reaction mix and carried out at room temperature for 10 min. Reactions were stopped by the addition of phosphoric acid (150 mM final concentration) and transferred to phosphocellulose discs. The phosphocellulose discs were washed five times with 150 mM phosphoric acid and air-dried. Scintillation fluid was added and discs were counted in a Wallac scintillation counter. The assay was incubated in the presence of a broad range of concentrations of Chk1 inhibitor compound and an $IC_{50}$ value for the compound was calculated. All compounds of the invention subjected to the assay exhibited $IC_{50}$ values in the assay of less than about 200 nM.

Example 2

Selectivity

Chk1 inhibitors of the present invention were tested for selectivity, with Chk1 as the comparison enzyme and the following protein kinases as comparator enzymes: Cdc2, Chk2, CTAK, EphA1, EphA2, Erk1, FGFR1, FGFR4, IR, JNK1, c-Kit, p38alpha, p38beta, p38delta, Ros, Rse, Rsk2, TrkA, TrkB, protein kinase A, protein kinase C, pp 60v-src, protein kinase B/Akt-1, p38MapK, p70S6K, calcium calmodulin-dependent kinase II, and ab1 tyrosine kinase.

The $IC_{50}$ value of a compound versus Chk1 was measured as described above. The $IC_{50}$ value of the compound against comparator enzymes was measured using the SelectSmart™ (MDS Pharma Servies, Bothell, Wash., USA) proprietary technology platform with either a modified ELISA procedure or fluorescence polarization. All inhibitors tested showed at least a 20-fold selectivity for Chk1 over the tested comparator enzymes.

Alternatively, assays for determining $IC_{50}$ for each of these kinases have been previously described in the literature, including U.S. Patent Publication No. 2002-016521 A1, and PCT/US95/00912, filed Jan. 23, 1995, both of which are incorporated by reference here.

Example 3

Cell-Based Assay for Determination of $EC_{TFS}$ Values of Chk1 Inhibitors

Cell-based potency of Chk1 inhibitors according to the invention was assessed by measuring the ability of the compound to sensitize HT29 human carcinoma cell line to gemcitabine. An average $EC_{TFS}$ value was derived following multiple experiments. Thus, a Chk1 inhibitor according to the invention was synthesized by methods described herein. The compound was dissolved in 100% dimethyl sulfoxide (DMSO) at a stock concentration of 10 mM and stored at $-70°$ C. HT29 cells were obtained from the ATCC and maintained in growth medium consisting of RPMI containing 10% fetal calf serum (FCS), pen/strep, glutamine and other supplements. Gemcitabine hydrochloride was obtained from Qventas and dissolved in phosphate buffered saline (PBS) at 50 mM and stored at $-20°$ C. $^3$H-thymidine was obtained from Perkin-Elmer.

HT29 cells were plated onto 96 well cell culture plates (Corning) at a density of $1.3 \times 10^3$ per well and allowed to adhere overnight. The following day, the gemcitabine was initially diluted 125-fold, followed by 5-fold dilutions in 1.2 ml Titer Tubes™ (BioRad) in growth medium. The final dilution series concentrations were: 11, 20, 4, 0.8, 0.16, 0.032, $6.4 \times 10^{-3}$, $1.28 \times 10^{-4}$, and $5.12 \times 10^{-5}$ nM. The diluted gemcitabine then was added to the cells for 2 hours. The gemcitabine then was washed out and the diluted Chk1 inhibitor of the invention was added to the cells for 24 hours. Following an initial 1000-fold dilution in growth medium, a 10 µM (DMSO stock) Chk1 inhibitor according to the invention was serially diluted 3-fold in 1.2 ml Titer Tubes™, yielding a final dilution series of: 2.5, 0.83, 0.28, 0.09, and 0.03 µM. Seventy-two hours later, the cells in each well were labeled with 1 µMCi $^3$H-thymidine for 12 hours, then frozen at $-70°$ C. The plates then were thawed and harvested onto 96 well filter plates (Millipore) using a Cell Mate™ plate harvester (Perkin Elmer). Microscint™ 20 (Perkin Elmer) then 30 µL was added and the plates were counted on a Top Count plate reader (Perkin Elmer). The data was normalized to cells treated with the Chk1 inhibitor according to the invention alone; then plotted on a log/log graph of gemcitabine concentration (µM) vs. relative cell growth (100% equaling 1.0). The increased fold sensitization at 90% growth inhibition was derived for each concentration of Chk1 inhibitor used, which then was plotted on a graph of Chk1 inhibitor concentration vs. fold sensitization. The $EC_{TFS}$ value then was calculated.

Chk1 inhibitors of the present invention that were subjected to the assay have measured $EC_{TFS}$ values of less than about 1000 nM.

Example 4

Chk1 Inhibitors of the Present Invention Enhance Killing of Cells by Cancer Treatments To demonstrate that the inhibition of Chk1 by a compound of the present invention sensitizes targeted cells to the killing effect of DNA-damaging agents, cells can be incubated in the presence of a present Chk1 inhibitor and exposed to either irradiation or a chemical DNA-damaging agent. Cells plated at a density of 1000-2000 per well in 96-well microtitre plates are grown in RMPI 1640 containing 10% FBS, 100 U/mL penicillin and 100 µg/mL streptomycin for 18 h at 37° C. in a humidified incubator with 5% CO2. Cells tested can include any cells or cell lines of interest, such as HeLa, ACHN, 786-0, HCT116, HCT15, SW620, HT29, Colo205, SK-MEL-5, SK-MEL-28, A549, H322, OVCAR-3, SK-OV-3, MDA-MB-231, MCF-7, PC-3, HL-60, K562, Bx-PC3, Mia-PaCa2, H810, H226, H2126, and MOLT4. All cell line designations refer to the following human cell lines:

| | |
|---|---|
| HeLa | cervical adenocarcinoma |
| ACHN | renal adenocarcinoma |
| 786-0 | renal adenocarcinoma |
| HCT116 | colon carcinoma |
| SW620 | colon carcinoma, lymph node metastasis |
| HT-29 | colonrectal adenocarcinoma |
| Colo205 | colon adenocarcinoma |
| SK-MEL-5 | melanoma |
| SK-MEL-28 | malignant melanoma |
| A549 | lung carcinoma |
| H322 | broncholoalveolar carcinoma |
| OVCAR-3 | ovarian adenocarcinoma |
| SK-OV-3 | ovarian adenocarcinoma |
| MDA-MB-231 | breast adenocarcinoma |
| MCF-7 | breast adenocarcinoma |
| PC-3 | prostate adenocarcinoma, from metastasis to bone |
| HL-60 | acute promyelocytic leukemia |
| K562 | chronic myelogenous leukemia |
| MOLT4 | acute lymphoblastic leukemia; T lymphoblast |

Cells are treated with media containing chemotherapeutic drugs alone or chemotherapeutic drugs and a Chk1 inhibitor. Cells are incubated for approximately 5 days before growth is measured by determination of levels of 3H-thymidine uptake. Chemotherapeutic drugs include etoposide, doxorubicin, cisplatin, chlorambucil, 5-fluorouracil (5-FU). The drug concentration necessary to inhibit cell growth to 90% of untreated control cells is defined as the $GI_{90}$.

Compounds of the present invention can be tested with additional antimetabolites, including methotrexate, hydroxyurea, 2-chloroadenosine, fludarabine, azacytidine, and gemcitibine to assess therein ability to enhance killing of the agents. Compounds of the present invention can be compared to one another by assessing enhanced killing of HT29 colorectal carcinoma in combination with gemcitibine.

In addition, the ability of the Chk1 inhibitors of the invention to enhance killing by radiation can be tested.

Example 5

Sensitive Assay to Measure Chk1 Inhibitor Activity in Animal Models

The following sensitive assay was developed to measure Chk1 inhibitor activity in rodent tumor models. In particular, the assay can be used, inter alia, to measure the ability of a Chk1 inhibitor to block Chk1 function in the tumor model, and to allow for assessment of conditions that facilitate access of the Chk1 inhibitor to the molecular target.

The ability of selective Chk1 inhibitors to abrogate a chemotherapy-induced checkpoint is measured using a quantitative immunofluourescent assay that measures mitotic index by monitoring histone H3 phosphorylation on serine 10 (H3-P), a mitosis-specific event (Ajiro et al., *J Biol Chem.*, 271: 13197-201, 1996; Goto et al., *J Biol Chem.*, 274:25543-9, 1999). The assay protocol is as follows. Tumors from rodents treated or untreated with Chk1 activator (in the present study, chemotherapy agent) and/or Chk1 inhibitor, are excised and paraffin embedded. The tumors are cut into 6 micron thick slices and mounted on glass slides. The paraffin is removed from the slides by 3 minute successive treatments with xylene, 100% ethanol, 95% ethanol, 70% ethanol and deionized water. The slides then are heated to 95° C. in 10 mM sodium citrate for 10 min followed by a 20 minute cooling step. The slides are blocked for 30 min with Block buffer (20% normal human serum and 2% bovine serum albumin in phosphate buffered saline containing 0.05% Triton X-100 (PBST)). The antiphospho histone H3 antibody (Upstate Biotech, Cat. #06-570) is diluted 1:200 in the Block buffer and incubated with the slides for one hour. The slides are washed 3 times 5 min in PBST. The secondary antibody, donkey antirabbit rhodamine (Jackson, cat #711-295-152) is added for 30 min. The slides then are washed twice in PBST and 75 µM of 0.1 µM/ml DAPI (Sigma) in phosphate buffered saline (PBS) is added and allowed to stain for 30 min. The slides then are washed two more times in PBST and mounted with Vectashield (Vector, cat #H-1400). Slides are viewed using fluorescence microscopy. The percentage of cells stained with H3-P antibody relative to total (DAPI stained) cells are quantified using Metamorph software (Universal Imaging Corporation, Version 4.6).

Example 6

Selective Chk1 Inhibitors Abrogate DNA Damage-Induced G2 and S Phase Checkpoints Previous studies demonstrated that selective Chk1 inhibitors substantially abrogate the DNA damage-induced G2/M and S phase checkpoints. In the former, DNA damage is induced by ionizing radiation (IR), whose target phase is the G2 phase. In the latter, DNA damage is induced by chemotherapeutic agents whose target phase is the S phase. See published U.S. Patent Application Publication 2003/0069284 and references cited therein.

Briefly, Chk1 inhibitor abrogation of IR-induced G2 DNA damage checkpoint is assayed by mitotic index experiments. Approximately $1 \times 10^6$ HeLa cells are irradiated with 800 rads and incubated for 7 h at 37° C. Because these cells are functionally p53 negative, they arrest exclusively in G2. Nocodazole then is added to a concentration of 0.5 µg/mL and incubated for 15 h at 37° C. (The addition of nocodazole is designed to trap cells that progressed through the G2 arrest in mitosis thus preventing them from further progressing into G1 and allowing for quantification of M phase cells.) A selective Chk1 inhibitor is added for 8 h, and the cells are harvested by centrifugation, washed once with PBS, then resuspended in 2.5 mL 75 mM KCl and centrifuged again. The cells then are fixed in 3 mL of freshly prepared cold, acetic acid:MeOH (1:3) and incubated on 0.5 ice for 20 min. Cells are pelleted, the fix solution is aspirated and the cells are resuspended in 0.5 mL of PBS. Mitotic spreads are prepared by pipeting 100 µL of the fixed cells onto a glass microscope slide and flooding the sample with 1 ml of fix solution. Slides then are air dried, stained with Wrights stain (Sigma, St. Louis, Mo.) for 1 minute, followed by one wash in water and one wash in 50% MeOH. The presence of condensed chromosomes and lack of nuclear envelope identified mitotic cells. Chk1 inhibitors result in an increase in the number of mitotic cells in the presence of irradiation, thereby demonstrating abrogation of the IR-induced G2 arrest. This checkpoint abrogation results in an enhancement in the activity of CyclinB/cdc2, which is required for progression of cells into mitosis. Cells treated with IR followed by Chk1 inhibitor thus progress into mitosis with damaged DNA. These experiments confirm the hypothesis that Chk1 is involved in the IR-induced G2.

Example 7

Chk1 Inhibitor is Taken Up by Tumor Cells in the Presence of Chk1 Activator in a Xenograft Tumor Model In a xenograft tumor model, nude mice are engrafted with HT29 colon carcinoma tumors on the flank and allowed to grow to 200 mm³. Mice then are treated with either vehicle, 300 mg/kg Chk1 inhibitor, 20 mg/kg gemcitabine or coadministered with 300 mg/kg Chk1 inhibitor and 20 mg/kg gemcitabine two times, three days apart on Days 1 and 4. Treatment of tumor-bearing mice by coadministration of Chk1 inhibitor and gemcitabine results in a four-day growth delay in tumors compared to gemcitabine alone.

To assess the diffusion of Chk1 inhibitors into tumor tissue, plasma and tissue levels of Chk1 inhibitor are measured. Using an Alzet pump, 500 mg/kg Chk1 inhibitor is administered to HT29 tumor-bearing mice in a continuous delivery system over a 24 hour period. Plasma samples are taken, then tumors, kidney, liver, spleen, and lung are harvested. Time points are collected at 1, 2, 4, 8, and 24 h. Tissues are extracted and levels of Chk1 inhibitor are quantified. This experiment demonstrates that a Chk1 inhibitor penetrated into normal and tumor tissue, reaches a level of about 15 µM in tumor tissue, and peaks in spleen tissue at 8 h at about 20 µM. Thus, Chk1 inhibitors were readily taken up by the proliferating cells and are useful, in conjunction with Chk1 activating chemotherapeutic agents, as therapies for the treatment of proliferative diseases.

Example 8

Dose Response of Tumors Treated with Chk1 Inhibitors and Gemcitabine

To determine an efficacious dose of Chk1 inhibitor following gemcitabine treatment and whether the dose-dependent checkpoint abrogation correlated with antitumor activity, a dose response experiment is performed.

Nude mice are engrafted with HT29 tumor cells and tumors allowed to develop for 10 days. The tumors at the start were approximately 100 mm³. Animals were treated with gemcitabine at the MTD (160 mg/kg) followed by Chk1 inhibitor at 50 mg/kg, 200 mg/kg, or 400 mg/kg. Gemcitabine pretreatment time is 32 h in this experiment as determined by a cell-based assay that indicated this timepoint as optimal for this type of tumor. Analysis of tumor volume in each treatment regimen indicated that treatment of HT29 tumor bearing mice with the described therapy slows tumor growth greater than gemcitabine alone, with either 200 mg/kg or 400 mg/kg Chk1 inhibitor plus gemcitabine again showing dose-dependent effects of the Chk1 inhibitor.

Example 9

Assay to Determine Whether an Agent is a Chk1 Activator

To determine whether an agent is a Chk1 activator, the phosphorylation state of Chk1 can be measured using phospho-specific antibodies to specific phosphorylation sites on Chk1. Serines 317 and 345 have been shown to be phosphorylated after treatment of cells with ionizing radiation, ultraviolet radiation, hydroxyurea, N-methyl-N'-nitro-N-nitrosoguanidine (MNNG), temozolamide and gemcitabine. Liu et al., *Genes Dev.* 14:1448-1459, 2000; Zhao et al., *Mol. Cell Biol.* 21:4129-4139, 2001; Lopez-Girona et al., *Proc. Natl. Acad. Sci. U.S.A.* 98:11289-11294, 2001; Guo et al., *Genes Dev.* 14:2745-2756, 2000; Gatei et al., *J. Biol. Chem.* 278:14806-14811, 2003; Ng et al., *J Biol Chem.* 279 (10): 8808-19, 2004; Wang et al., *Natl Acad Sci USA.* 100(26): 15387-92, 2003; Stojic et al., *Genes Dev.* 18(11):1331-44, 2004. These serine sites are phosphorylated by upstream checkpoint kinases, Atm and Atr. Liu et al., *Genes Dev.* 14:1448-1459, 2000; Zhao et al. *Mol. Cell Biol.*, 21:4129-4139, 2001).

The phosphorylation of these sites in response to a candidate Chk1 activator can be monitored by Western blot or immunohistochemistry of tumor cells. For example, the following procedure can be used to demonstrate that gemcitabine results in Chk1 activation at serine 345 and 317. HT29 cells are treated with 20 µM gemcitabine for two h. The gemcitabine is washed out of the cell growth media and cells are incubated for 22 additional h. Protein lysates are prepared and separated by an SDS-polyacrylamide gel electrophoresis. Proteins are transferred to PVDF membranes and probed with antisera (Cell Signalling) specific for either phosphorylated serine 317 or 345 (Cell Signalling). Western blots show that gemcitabine treatment of HT29 colon carcinoma cells results in the phosphorylation of both serines 317 and 345.

Example 10

Assay to Monitor Chk1 Activity in Response to a Chk1 Inhibitor

It has been found that phosphorylation of Chk1 at serine 296 is stimulated by treatment of tumor cells with gemcitabine, and that phosphorylation at this site is inhibited by Chk1 inhibitors. Phosphorylation at this site is not inhibited by wortmannin, which inhibits Atm and Atr. Therefore, the phosphorylation of serine 296 is distinct from phosphorylation at serines 317 and 345. In addition, it has been found that this site is phosphorylated in purified Chk1 preparations, suggesting that the purified enzyme is able to phosphorylate itself or other Chk1 molecules at serine 296. Taken together, these data suggest that phosphorylation at serine 296 is performed by Chk1 itself. Therefore, this approach can be used to monitor Chk1 activity in tumors in response to Chk1 activators. Further, this approach can be used to measure inhibition of Chk1 activation by Chk1 inhibitors.

Thus, HT 29 cells are treated with 20 µM gemcitabine for two h. The gemcitabine is washed out of the cell growth media and cells are incubated for 22 additional h. Protein lysates are prepared and separated by an SDS-polyacrylamide gel electrophoresis. Proteins are transferred to polyvinylidene fluoride (PVDF) membranes and probed with antisera (Cell Signalling) specific for phosphorlyated serine 296 (Cell Signalling). Western blot shows that gemcitabine treatment of HT29 colon carcinoma cells results in the phosphorylation of serine 296. Further, HT29 cells treated with selective Chk1 inhibitors for 15 min show no serine 296 phosphorylation. These data suggest that serine 296 phosphorylation is performed by the Chk1 kinase.

Example 11

Animal Tumor Models

To test the ability of the Chk1 inhibitors of the invention to enhance the killing of tumors by DNA damaging agents in mice, xenograft tumor models using colon tumor cell lines are established. 5-fluorouracil (5-FU) or gemcitabine can be used as DNA damaging agents. HT29 and Colo205 (human colon carcinoma) and H460 and Calu-6 (nonsmall cell carcinoma) cells can be used to propagate xenograft tumors in 6-8 week old female thymic Balb/c (nu/nu) mice. Mice are maintained in a laminar airflow cabinet under pathogen-free conditions and fed sterile food and water ad libitum. Cell lines are grown to subconfluence in RPMI 1640 media supplemented with 10% FBS, 100 U/mL penicillin, 100 µg/mL streptomycin, and 1.5 mM L-glutamine in a 5% $CO_2$ humidified environment. Single cell suspensions are prepared in CMF-PBS, and cell concentration adjusted to $1 \times 10^8$ cells/mL. Mice are inoculated subcutaneously (s.c.) on the right flank or right leg with a total of $1 \times 10^7$ cells (100 µL).

Mice are randomized (5-15 mice/group) into four treatment groups and used when tumors reach a volume of 75-100 $cm^3$ (usually 7-11 days post-inoculation). Tumors are measured with vernier calipers and tumor volumes are estimated using the empirically derived formula: tumor volume $(cm^3)$= tumor length (cm)×tumor width (cm)×tumor depth (cm)/3.3. Treatment consists of i) 100 µL intraperitoneal (i.p) injection of gemcitabine at 160 mg/kg. A delay in tumor growth is observed in the mice treated with gemcitabine. Treatment of mice with both 160 mg/kg gemcitabine in combination with oral administration of Chk1 inhibitors is expected to reduce tumor volumes and prolong life. Tumor size is monitored every other day for the duration of the experiment.

Obviously, many modifications and variations of the invention as hereinbefore set forth can be made without departing from the spirit and scope thereof, and, therefore, only such limitations should be imposed as are indicated by the appended claims.

What is claimed is:

1. A compound which is 1-[5-bromo-4-methyl-2-S-(morpholin-2-ylmethoxy)-phenyl]-3-(5-methyl-pyrazin-2-yl)-urea or a pharmaceutically acceptable salt thereof.

2. A pharmaceutical composition comprising a compound which is 1-[5-bromo-4-methyl-2-S-(morpholin-2-ylmethoxy)-phenyl]-3-(5-methyl-pyrazin-2-yl)-urea or a pharmaceutically acceptable salt thereof, in combination with one or more pharmaceutically acceptable diluents or carriers.

3. A method of treating a colorectal cancer, a head and neck cancer, a pancreatic cancer, a breast cancer, a gastric cancer, a bladder cancer, a vulvar cancer, a leukemia, a lymphoma, a melanoma, a renal cell carcinoma, an ovarian cancer, a brain cancer, an osteosarcoma, or a lung cancer which comprises administering to a patient in need thereof a therapeutically effective amount of a compound which is 1-[5-bromo-4-methyl-2-S-(morpholin-2-ylmethoxy)-phenyl]-3-(5-methyl-pyrazin-2-yl)-urea or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,093,244 B2 | Page 1 of 1 |
| APPLICATION NO. | : 11/908416 | |
| DATED | : January 10, 2012 | |
| INVENTOR(S) | : Diaz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 711 days.

Signed and Sealed this

Seventeenth Day of April, 2012

David J. Kappos
*Director of the United States Patent and Trademark Office*